US007393682B1

(12) United States Patent
Lee et al.

(10) Patent No.: US 7,393,682 B1
(45) Date of Patent: *Jul. 1, 2008

(54) POLYNUCLEOTIDES ENCODING PROMYOSTATIN POLYPEPTIDES

(75) Inventors: Se-Jin Lee, Baltimore, MD (US); Alexandra C. McPherron, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 1063 days.

This patent is subject to a terminal disclaimer.

(21) Appl. No.: 09/708,693

(22) Filed: Nov. 7, 2000

Related U.S. Application Data

(63) Continuation of application No. 09/628,112, filed on Jul. 27, 2000, which is a continuation-in-part of application No. 09/124,180, filed on Jul. 28, 1998, now abandoned, which is a continuation-in-part of application No. 09/019,070, filed on Feb. 5, 1998, now abandoned, which is a continuation-in-part of application No. 08/862,445, filed on May 23, 1997, now abandoned, which is a continuation-in-part of application No. 08/847,910, filed on Apr. 28, 1997, now abandoned, which is a continuation-in-part of application No. 08/795,071, filed on Feb. 5, 1997, now Pat. No. 5,994,618, which is a continuation-in-part of application No. 08/525,596, filed as application No. PCT/US94/03019 on Mar. 18, 1994, now Pat. No. 5,827,733, said application No. 09/124,180 is a continuation-in-part of application No. 08/033,923, filed on Mar. 19, 1993, now abandoned.

(51) Int. Cl.
*C12N 5/00* (2006.01)
*C12N 15/00* (2006.01)
*C12N 1/20* (2006.01)
*C12N 1/14* (2006.01)
*C07H 21/04* (2006.01)

(52) U.S. Cl. .................. 435/325; 435/69.1; 435/252.3; 435/254.11; 435/320.1; 536/23.5

(58) Field of Classification Search ................ 435/69.1; 530/350; 536/23.5
See application file for complete search history.

(56) References Cited

U.S. PATENT DOCUMENTS

| | | | |
|---|---|---|---|
| 5,616,561 A | 4/1997 | Barcellos-Hoff | |
| 5,827,733 A | 10/1998 | Lee et al. | |
| 5,885,794 A | 3/1999 | Mathews et al. | |
| 5,994,618 A | 11/1999 | Lee et al. | |
| 6,004,937 A | 12/1999 | Wood et al. | |
| 6,369,201 B1 * | 4/2002 | Barker et al. | 530/387.1 |

FOREIGN PATENT DOCUMENTS

| WO | WO 91/08291 | 6/1991 |
|---|---|---|
| WO | WO 94/21681 | 9/1994 |
| WO | WO 96/01845 | 1/1996 |
| WO | WO 98/33887 | 8/1998 |
| WO | 99/02667 A1 | 1/1999 |
| WO | WO99/06559 | 2/1999 |
| WO | 99/40181 A1 | 8/1999 |
| WO | 99/42573 A1 | 8/1999 |
| WO | WO99/56768 | 11/1999 |

OTHER PUBLICATIONS

McPherron et al.: "Regulation of skeletal muscle mass in mice by a new TGF-β superfamily member." Nature, (May 1, 1997) 387 (6628) 83-90., XP002085797.

Love, et al., "Transgenic Birds by DNA Microinjection", Bio/Technology, Jan. 1994, vol. 12, No. 1, pp. 60-63.

Slack, J.M.W., "Growth Control: Action Mouse", Current Biology, Aug. 1, 1997, vol. 7, No. 8, pp. R467-R469.

International Search Report, PCT/US99/02511, Mailed May 13, 1999, 2 pages.

Berk et al., "Mice Lacking the *ski* Proto-Oncogene Have Defects in Neurulation, Craniofacial Patterning, and Skeletal Development," *Genes & Development* 11:2029-2039 (1997).

Böttinger et al., "The Recombinant Proregion of Transforming Growth Factor β1 (Latency-Associated Peptide) Inhibits Active Transforming Growth Factor β1 in Transgenic Mice," *Proc. Natl. Acad. Sci* 93:5877-5882 (1996).

Gamer et al., "A Novel BMP Expressed in Developing Mouse Limb, Spinal Cord, and Tail Bud Is a Potent Mesoderm Inducer in *Xenopus* Embryos," *Developmental Biology* 208: 222-232 (1999).

Gentry and Nash, "The Pro Domain of Pre-Pro-Transforming Growth Factor β1 When Independently Expressed is a Functional Binding Protein for the Mature Growth Factor," *Biochemistry* 29:6851-6857 (1990).

Gonzalez-Cadavid et al., "Organization of the Luman Myostatin Gene and Expression in Healthy Men and HIV-Infected Men with Muscle Wasting," *Proc.Natl.Acad.Sci.* 95:14938-14943 (1998).

Lee and McPherron, "Myostatin and the Control of Skeletal Muscle Mass," *Curr. Opin. Gent. Dev.* 9:604-607 (1999).

(Continued)

*Primary Examiner*—Marianne P Allen
(74) *Attorney, Agent, or Firm*—DLA Piper US LLP

(57) ABSTRACT

The present invention provides isolated polynucleotides encoding promyostatin polypeptides or a peptide portion thereof, polynucleotides complementary thereto, and oligonucleotides that can specifically hybridize to such polynucleotides. The present invention also provides an isolated polynucleotide encoding a mature myostatin peptide.

5 Claims, 3 Drawing Sheets

OTHER PUBLICATIONS

Luo et al., "The Ski Oncoprotein Interacts with the Smad Proteins to Repress TGFβ Signaling," *Genes & Dev.* 13:2196-2206 (1999).

McPherron et al., "Regulation of Anterior/Posterior Patterning of the Axial Skeleton by Growth/Differentiation Factor 11," *Nature Genetics* 22:260-264 (1999).

Miyazono et al., "Latent High Molecular Weight Complex of Transforming Growth Factor β1," *J. Bio. Chem.* 263 (13):6407-6415 (1988).

Munger et al., "Latent Transforming Growth Factor-β: Structural Features and Mechanisms of Activation," *Kidney Intl.* 51:1376-1382 (1997).

Nakamura et al., "Activin-Binding Protein from Rat Ovary is Follistatin," *Science* 247:836-838 (1990).

Oh and Li, "The Signaling Pathway Mediated by the Type IIB Activin Receptor Controls Axial Patterning and Lateral Asymmetry in the Mouse," *Genes & Dev.* 11:1812-1826 (1997).

Sutrave et al., "Ski can Cause Selective Growth of Skeletal Muscle in Transgenic Mice," *Genes & Dev.* 4:1462-1472 (1990).

Constam and Robertson, "Regulation of Bone Morphogenetic Protein Activity by Pro Domains and Proprotein Convertases," J. Cell. Biol., vol. 144, No. 1, Jan. 1999, pp. 139-149.

* cited by examiner

```
                 10                  20                 30
     M M Q K L Q M Y V Y I Y L F M L I A A G P V D L N E G S E R   murine
     M H F T Q - - - V L I S L S V L I A C G P V G Y G D I T A H   zebrafish
     - - - - - - - - - - - - - - - - - - - - - - - - - - - - - -   salmon1
     - - - - - - - - - - - - - - - - - - - - - - - - - - - - - -   salmon2

40                  50                 60
 31  E E - - N V E K E G L C N A C A W R Q N T R Y S R I E A I   murine
 28  Q Q P S T A T E E S E L C S T C E F R Q H S K L M R L H A I   zebrafish
  1  - - - - - - - - - - - - - - - - - - - - - - - - - - - - - -   salmon1
  1  - - - - - - - - - - - - - - - - - - - - - - - - - - - - - -   salmon2

70                  80                 90
 58  K I Q I L S K L R L E T A P N I S K D A I R Q L L P R A P P   murine
 58  K S Q I L S K L R L K Q A P N I S R D V V K Q L L P K A P P   zebrafish
  1  - - - - - - - - - - - - - - - - - - - - - - - - - - - - - -   salmon1
  1  - - - - - - - - - - - - - - - - - - - - - - - - - - - - - -   salmon2

100                 110                120
 88  L R E L I D Q Y D V Q R D D S S D G S L E D D D Y H A T T E   murine
 88  L Q Q L L D Q Y D V L G D D S K D G A V E E D D E H A T T E   zebrafish
  1  - - - - - - - - - - - - - - - - - - - - - - - - - - - - - -   salmon1
  1  - - - - - - - - - - - - - - - - - - - - - - - - - - - - - -   salmon2

130                 140                150
118  T I I T M P T E S D F L M Q A D G K P K C C F F K F S S K I   murine
118  T I M T M A T E P D P I V Q V D R K P K C C F F S F S P K I   zebrafish
  1  - - - - - - - - - - - - - - - - - - - - - - - - - - - - - -   salmon1
  1  - - - - - - - - - - - - - - - - - - - - - - - - - - - - - -   salmon2

160                 170                180
148  Q Y N K V V K A Q L W I Y L R P V K T P T T V F V Q I L R L   murine
148  Q A N R I V R A Q L W V H L R P A E E A T T V F L Q I S R L   zebrafish
  1  - - - - - - - - - - - - - - - - - - - - - - - - - - - - - -   salmon1
  1  - - - - - - - - - - - - - - - - - - - - - - - - - - - - - -   salmon2

190                 200                210
178  I K P M K D G T R Y T G I R S L K L D M S P G T G I W Q S I   murine
178  M - P V K D G G R H R - I R S L K I D V N A G V T S W Q S I   zebrafish
  1  - - - - - - - - - - - - - - - - - - - - - - - - - - - - - -   salmon1
  1  - - - - - - - - - - - - - - - - - - - - - - - - - - - - - -   salmon2

220                 230                240
208  D V K T V L Q N W L K Q P E S N L G I E I K A L D E N G H D   murine
206  D V K Q V L T V W L K Q P E T N R G I E I N A Y D A K G N D   zebrafish
  1  - - - - - - - - - - - Q P E T N W G I E I N A F D S K G N D   salmon1
  1  - - - - - - - - - - - - - - - - - - - - - - - - - - - - - -   salmon2
```

Fig. 2 (cont)

```
                    250              260              270
238    L A V T F P G P G E D G L N P F L E V K V T D T P K R S R R   murine
236    L A V T S T E T G E D G L L P F M E V K I S E G P K R I R R   zebrafish
 20    L A V T S A E A G E - G L Q P F M E V T I S E G P K R S R R   salmon1
  1    - - V T S T E A G E - G L Q P F M E V K I S E G P K R S R R   salmon2

280              290              300
268    D F G L D C D E H S T E S R C C R Y P L T V D F E A F G W D   murine
266    D S G L D C D E N S S E S R C C R Y P L T V D F E D F G W D   zebrafish
 49    D S G L D C D E N S P E S R C C R Y P L T V D F E D F G W D   salmon1
 28    D S G L D C D E N S P E S R C C R Y P L T V D F E D F G W D   salmon2

310              320              330
298    W I I A P K R Y K A N Y C S G E C E F V F L Q K Y P H T H L   murine
296    W I I A P K R Y K A N Y C S G E C D Y M Y L Q K Y P H T H L   zebrafish
 79    W I I A P K R Y K A N Y C S G E C E Y M H L Q K Y P H T H L   salmon1
 58    W I I A P K R Y K A N Y C S G E C E Y M H L Q K Y P H T H L   salmon2

340              350              360
328    V H Q A N P R G S A G P C C T P T K M S P I N M L Y F N G K   murine
326    V N K A S P R G T A G P C C T P T K M S P I N M L Y F N G K   zebrafish
109    V N K A N P R G T A G P C C T P T K M S P I N M L Y F N R K   salmon1
 88    V N K A N P R G T A G P C C T P T K M S P I N M L Y F N R K   salmon2

370
358    E Q I I Y G K I P A M V V D R C G C S   murine
356    E Q I I Y G K I P S M V V D R C G C S   zebrafish
139    E Q I I Y G K I P S M V V D R C G C S   salmon1
118    E Q I I Y G K I P S M V V D R C G C S   salmon2
```

SEQUENCE LISTING

<160> NUMBER OF SEQ ID NOS: 29

<210> SEQ ID NO 1
<211> LENGTH: 2743
<212> TYPE: DNA
<213> ORGANISM: Homo sapiens
<220> FEATURE:

```
<221> NAME/KEY: CDS
<222> LOCATION: (59)..(1183)

<400> SEQUENCE: 1
```

| | | | | | | | | | | | | | | | | |
|---|---|---|---|---|---|---|---|---|---|---|---|---|---|---|---|---|
| aagaaaagta aaaggaagaa acaagaacaa gaaaaaagat tatattgatt ttaaaatc | | | | | | | | | | | | | | | | 58 |
| atg | caa | aaa | ctg | caa | ctc | tgt | gtt | tat | att | tac | ctg | ttt | atg | ctg | att | 106 |
| Met | Gln | Lys | Leu | Gln | Leu | Cys | Val | Tyr | Ile | Tyr | Leu | Phe | Met | Leu | Ile | |
| 1 | | | | 5 | | | | | 10 | | | | | 15 | | |
| gtt | gct | ggt | cca | gtg | gat | cta | aat | gag | aac | agt | gag | caa | aaa | gaa | aat | 154 |
| Val | Ala | Gly | Pro | Val | Asp | Leu | Asn | Glu | Asn | Ser | Glu | Gln | Lys | Glu | Asn | |
| | | | 20 | | | | | 25 | | | | | 30 | | | |
| gtg | gaa | aaa | gag | ggg | ctg | tgt | aat | gca | tgt | act | tgg | aga | caa | aac | act | 202 |
| Val | Glu | Lys | Glu | Gly | Leu | Cys | Asn | Ala | Cys | Thr | Trp | Arg | Gln | Asn | Thr | |
| | | 35 | | | | | 40 | | | | | 45 | | | | |
| aaa | tct | tca | aga | ata | gaa | gcc | att | aag | ata | caa | atc | ctc | agt | aaa | ctt | 250 |
| Lys | Ser | Ser | Arg | Ile | Glu | Ala | Ile | Lys | Ile | Gln | Ile | Leu | Ser | Lys | Leu | |
| | 50 | | | | | 55 | | | | | 60 | | | | | |
| cgt | ctg | gaa | aca | gct | cct | aac | atc | agc | aaa | gat | gtt | ata | aga | caa | ctt | 298 |
| Arg | Leu | Glu | Thr | Ala | Pro | Asn | Ile | Ser | Lys | Asp | Val | Ile | Arg | Gln | Leu | |
| 65 | | | | | 70 | | | | | 75 | | | | | 80 | |
| tta | ccc | aaa | gct | cct | cca | ctc | cgg | gaa | ctg | att | gat | cag | tat | gat | gtc | 346 |
| Leu | Pro | Lys | Ala | Pro | Pro | Leu | Arg | Glu | Leu | Ile | Asp | Gln | Tyr | Asp | Val | |
| | | | | 85 | | | | | 90 | | | | | 95 | | |
| cag | agg | gat | gac | agc | agc | gat | ggc | tct | ttg | gaa | gat | gac | gat | tat | cac | 394 |
| Gln | Arg | Asp | Asp | Ser | Ser | Asp | Gly | Ser | Leu | Glu | Asp | Asp | Asp | Tyr | His | |
| | | | 100 | | | | | 105 | | | | | 110 | | | |
| gct | aca | acg | gaa | aca | atc | att | acc | atg | cct | aca | gag | tct | gat | ttt | cta | 442 |
| Ala | Thr | Thr | Glu | Thr | Ile | Ile | Thr | Met | Pro | Thr | Glu | Ser | Asp | Phe | Leu | |
| | | 115 | | | | | 120 | | | | | 125 | | | | |
| atg | caa | gtg | gat | gga | aaa | ccc | aaa | tgt | tgc | ttc | ttt | aaa | ttt | agc | tct | 490 |
| Met | Gln | Val | Asp | Gly | Lys | Pro | Lys | Cys | Cys | Phe | Phe | Lys | Phe | Ser | Ser | |
| | 130 | | | | | 135 | | | | | 140 | | | | | |
| aaa | ata | caa | tac | aat | aaa | gta | gta | aag | gcc | caa | cta | tgg | ata | tat | ttg | 538 |
| Lys | Ile | Gln | Tyr | Asn | Lys | Val | Val | Lys | Ala | Gln | Leu | Trp | Ile | Tyr | Leu | |
| 145 | | | | | 150 | | | | | 155 | | | | | 160 | |
| aga | ccc | gtc | gag | act | cct | aca | aca | gtg | ttt | gtg | caa | atc | ctg | aga | ctc | 586 |
| Arg | Pro | Val | Glu | Thr | Pro | Thr | Thr | Val | Phe | Val | Gln | Ile | Leu | Arg | Leu | |
| | | | | 165 | | | | | 170 | | | | | 175 | | |
| atc | aaa | cct | atg | aaa | gac | ggt | aca | agg | tat | act | gga | atc | cga | tct | ctg | 634 |
| Ile | Lys | Pro | Met | Lys | Asp | Gly | Thr | Arg | Tyr | Thr | Gly | Ile | Arg | Ser | Leu | |
| | | | 180 | | | | | 185 | | | | | 190 | | | |
| aaa | ctt | gac | atg | aac | cca | ggc | act | ggt | att | tgg | cag | agc | att | gat | gtg | 682 |
| Lys | Leu | Asp | Met | Asn | Pro | Gly | Thr | Gly | Ile | Trp | Gln | Ser | Ile | Asp | Val | |
| | | 195 | | | | | 200 | | | | | 205 | | | | |
| aag | aca | gtg | ttg | caa | aat | tgg | ctc | aaa | caa | cct | gaa | tcc | aac | tta | ggc | 730 |
| Lys | Thr | Val | Leu | Gln | Asn | Trp | Leu | Lys | Gln | Pro | Glu | Ser | Asn | Leu | Gly | |
| | 210 | | | | | 215 | | | | | 220 | | | | | |
| att | gaa | ata | aaa | gct | tta | gat | gag | aat | ggt | cat | gat | ctt | gct | gta | acc | 778 |
| Ile | Glu | Ile | Lys | Ala | Leu | Asp | Glu | Asn | Gly | His | Asp | Leu | Ala | Val | Thr | |
| 225 | | | | | 230 | | | | | 235 | | | | | 240 | |
| ttc | cca | gga | cca | gga | gaa | gat | ggg | ctg | aat | ccg | ttt | tta | gag | gtc | aag | 826 |
| Phe | Pro | Gly | Pro | Gly | Glu | Asp | Gly | Leu | Asn | Pro | Phe | Leu | Glu | Val | Lys | |
| | | | | 245 | | | | | 250 | | | | | 255 | | |
| gta | aca | gac | aca | cca | aaa | aga | tcc | aga | agg | gat | ttt | ggt | ctt | gac | tgt | 874 |
| Val | Thr | Asp | Thr | Pro | Lys | Arg | Ser | Arg | Arg | Asp | Phe | Gly | Leu | Asp | Cys | |
| | | | 260 | | | | | 265 | | | | | 270 | | | |
| gat | gag | cac | tca | aca | gaa | tca | cga | tgc | tgt | cgt | tac | cct | cta | act | gtg | 922 |
| Asp | Glu | His | Ser | Thr | Glu | Ser | Arg | Cys | Cys | Arg | Tyr | Pro | Leu | Thr | Val | |
| | | 275 | | | | | 280 | | | | | 285 | | | | |

```
gat ttt gaa gct ttt gga tgg gat tgg att atc gct cct aaa aga tat         970
Asp Phe Glu Ala Phe Gly Trp Asp Trp Ile Ile Ala Pro Lys Arg Tyr
    290                 295                 300 aag gcc aat tac tgc tct gga gag tgt gaa ttt gta ttt tta caa aaa        1018
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca        1066
Tyr Pro His Thr His Leu Val His Gln Ala Asn Pro Arg Gly Ser Ala
                325                 330                 335 ggc cct tgc tgt act ccc aca aag atg tct cca att aat atg cta tat        1114
Gly Pro Cys Cys Thr Pro Thr Lys Met Ser Pro Ile Asn Met Leu Tyr
            340                 345                 350 ttt aat ggc aaa gaa caa ata ata tat ggg aaa att cca gcg atg gta        1162
Phe Asn Gly Lys Glu Gln Ile Ile Tyr Gly Lys Ile Pro Ala Met Val
        355                 360                 365 gta gac cgc tgt ggg tgc tca tgagatttat attaagcgtt cataacttcc           1213
Val Asp Arg Cys Gly Cys Ser
    370                 375 taaaacatgg aaggttttcc cctcaacaat tttgaagctg tgaaattaag taccacaggc      1273
tataggccta gagtatgcta cagtcactta agcataagct acagtatgta aactaaaagg      1333
gggaatatat gcaatggttg gcatttaacc atccaaacaa atcatacaag aaagttttat      1393 gattccaga gttttgagc tagaaggaga tcaaattaca tttatgttcc tatatattac        1453
aacatcggcg aggaaatgaa agcgattctc cttgagttct gatgaattaa aggagtatgc      1513
tttaaagtct atttctttaa agttttgttt aatatttaca gaaaaatcca catacagtat      1573
tggtaaaatg caggattgtt ataccatc attcgaatca tccttaaaca cttgaattta        1633
tattgtatgg tagtatactt ggtaagataa aattccacaa aaatagggat ggtgcagcat      1693
atgcaatttc cattcctatt ataattgaca cagtacatta acaatccatg ccaacggtgc      1753
taatacgata ggctgaatgt ctgaggctac caggtttatc ataaaaaaa cattcagtaa       1813 aatagtaagt ttctcttttc ttcaggtgca ttttcctaca cctccaaatg aggaatggat      1873
tttctttaat gtaagaagaa tcattttct agaggttggc tttcaattct gtagcatact       1933
tggagaaact gcattatctt aaaaggcagt caaatggtgt tgttttat caaaatgtca        1993 aaataacata cttggagaag tatgtaattt tgtctttgga aaattacaac actgcctttg      2053
caacactgca gtttttatgg taaaataata gaaatgatcg actctatcaa tattgtataa      2113
aaagactgaa acaatgcatt tatataatat gtatacaata ttgttttgta aataagtgtc      2173 tccttttta tttactttgg tatattttta cactaaggac atttcaaatt aagtactaag       2233
gcacaaagac atgtcatgca tcacagaaaa gcaactactt atatttcaga gcaaattagc      2293
agattaaata gtggtcttaa aactccatat gttaatgatt agatggttat attacaatca      2353
ttttatattt ttttacatga ttaacattca cttatggatt catgatggct gtataaagtg      2413
aatttgaaat ttcaatggtt tactgtcatt gtgtttaaat ctcaacgttc cattatttta     2473
atacttgcaa aaacattact aagtatacca aaataattga ctctattatc tgaaatgaag      2533
aataaactga tgctatctca acaataactg ttacttttat tttataattt gataatgaat      2593
atatttctgc atttatttac ttctgttttg taaattggga ttttgttaat caaatttatt      2653
gtactatgac taaatgaaat tatttcttac atctaatttg tagaaacagt ataagttata     2713
ttaaagtgtt ttcacatttt tttgaaagac                                       2743

<210> SEQ ID NO 2
<211> LENGTH: 375
```

```
<212> TYPE: PRT
<213> ORGANISM: Homo sapiens

<400> SEQUENCE: 2

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65              70                  75                  80

Leu Pro Lys Ala Pro Pro Leu Arg Glu Leu Ile Asp Gln Tyr Asp Val
            85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
370                 375

<210> SEQ ID NO 3
```

```
<211> LENGTH: 2676
<212> TYPE: DNA
<213> ORGANISM: Mus musculus
<220> FEATURE:
<221> NAME/KEY: CDS
<222> LOCATION: (104)..(1231)

<400> SEQUENCE: 3
gtctctcgga cggtacatgc actaatattt cacttggcat tactcaaaag caaaagaag      60 aaataagaac aagggaaaaa aaaagattgt gctgattttt aaa atg atg caa aaa      115
                                              Met Met Gln Lys
                                                1 ctg caa atg tat gtt tat att tac ctg ttc atg ctg att gct gct ggc      163
Leu Gln Met Tyr Val Tyr Ile Tyr Leu Phe Met Leu Ile Ala Ala Gly
 5              10                  15                  20 cca gtg gat cta aat gag ggc agt gag aga gaa gaa aat gtg gaa aaa      211
Pro Val Asp Leu Asn Glu Gly Ser Glu Arg Glu Glu Asn Val Glu Lys
             25                  30                  35 gag ggg ctg tgt aat gca tgt gcg tgg aga caa aac acg agg tac tcc      259
Glu Gly Leu Cys Asn Ala Cys Ala Trp Arg Gln Asn Thr Arg Tyr Ser
         40                  45                  50 aga ata gaa gcc ata aaa att caa atc ctc agt aag ctg cgc ctg gaa      307
Arg Ile Glu Ala Ile Lys Ile Gln Ile Leu Ser Lys Leu Arg Leu Glu
     55                  60                  65 aca gct cct aac atc agc aaa gat gct ata aga caa ctt ctg cca aga      355
Thr Ala Pro Asn Ile Ser Lys Asp Ala Ile Arg Gln Leu Leu Pro Arg
 70                  75                  80 gcg cct cca ctc cgg gaa ctg atc gat cag tac gac gtc cag agg gat      403
Ala Pro Pro Leu Arg Glu Leu Ile Asp Gln Tyr Asp Val Gln Arg Asp
 85                  90                  95                 100 gac agc agt gat ggc tct ttg gaa gat gac gat tat cac gct acc acg      451
Asp Ser Ser Asp Gly Ser Leu Glu Asp Asp Asp Tyr His Ala Thr Thr
                105                 110                 115 gaa aca atc att acc atg cct aca gag tct gac ttt cta atg caa gcg      499
Glu Thr Ile Ile Thr Met Pro Thr Glu Ser Asp Phe Leu Met Gln Ala
            120                 125                 130 gat ggc aag ccc aaa tgt tgc ttt ttt aaa ttt agc tct aaa ata cag      547
Asp Gly Lys Pro Lys Cys Cys Phe Phe Lys Phe Ser Ser Lys Ile Gln
        135                 140                 145 tac aac aaa gta gta aaa gcc caa ctg tgg ata tat ctc aga ccc gtc      595
Tyr Asn Lys Val Val Lys Ala Gln Leu Trp Ile Tyr Leu Arg Pro Val
    150                 155                 160 aag act cct aca aca gtg ttt gtg caa atc ctg aga ctc atc aaa ccc      643
Lys Thr Pro Thr Thr Val Phe Val Gln Ile Leu Arg Leu Ile Lys Pro
165                 170                 175                 180 atg aaa gac ggt aca agg tat act gga atc cga tct ctg aaa ctt gac      691
Met Lys Asp Gly Thr Arg Tyr Thr Gly Ile Arg Ser Leu Lys Leu Asp
                185                 190                 195 atg agc cca ggc act ggt att tgg cag agt att gat gtg aag aca gtg      739
Met Ser Pro Gly Thr Gly Ile Trp Gln Ser Ile Asp Val Lys Thr Val
            200                 205                 210 ttg caa aat tgg ctc aaa cag cct gaa tcc aac tta ggc att gaa atc      787
Leu Gln Asn Trp Leu Lys Gln Pro Glu Ser Asn Leu Gly Ile Glu Ile
        215                 220                 225 aaa gct ttg gat gag aat ggc cat gat ctt gct gta acc ttc cca gga      835
Lys Ala Leu Asp Glu Asn Gly His Asp Leu Ala Val Thr Phe Pro Gly
    230                 235                 240 cca gga gaa gat ggg ctg aat ccc ttt tta gaa gtc aag gtg aca gac      883
Pro Gly Glu Asp Gly Leu Asn Pro Phe Leu Glu Val Lys Val Thr Asp
245                 250                 255                 260
```

```
aca ccc aag agg tcc cgg aga gac ttt ggg ctt gac tgc gat gag cac      931
Thr Pro Lys Arg Ser Arg Arg Asp Phe Gly Leu Asp Cys Asp Glu His
            265                 270                 275 tcc acg gaa tcc cgg tgc tgc cgc tac ccc ctc acg gtc gat ttt gaa      979
Ser Thr Glu Ser Arg Cys Cys Arg Tyr Pro Leu Thr Val Asp Phe Glu
        280                 285                 290 gcc ttt gga tgg gac tgg att atc gca ccc aaa aga tat aag gcc aat     1027
Ala Phe Gly Trp Asp Trp Ile Ile Ala Pro Lys Arg Tyr Lys Ala Asn
                295                 300                 305 tac tgc tca gga gag tgt gaa ttt gtg ttt tta caa aaa tat ccg cat     1075
Tyr Cys Ser Gly Glu Cys Glu Phe Val Phe Leu Gln Lys Tyr Pro His
            310                 315                 320 act cat ctt gtg cac caa gca aac ccc aga ggc tca gca ggc cct tgc     1123
Thr His Leu Val His Gln Ala Asn Pro Arg Gly Ser Ala Gly Pro Cys
325                 330                 335                 340 tgc act ccg aca aaa atg tct ccc att aat atg cta tat ttt aat ggc     1171
Cys Thr Pro Thr Lys Met Ser Pro Ile Asn Met Leu Tyr Phe Asn Gly
                345                 350                 355 aaa gaa caa ata ata tat ggg aaa att cca gcc atg gta gta gac cgc     1219
Lys Glu Gln Ile Ile Tyr Gly Lys Ile Pro Ala Met Val Val Asp Arg
            360                 365                 370 tgt ggg tgc tca tgagctttgc attaggttag aaacttccca agtcatggaa         1271
Cys Gly Cys Ser
            375 ggtcttcccc tcaatttcga aactgtgaat tcaagcacca caggctgtag gccttgagta   1331 tgctctagta acgtaagcac aagctacagt gtatgaacta aaagagagaa tagatgcaat   1391 ggttggcatt caaccaccaa aataaaccat actataggat gttgtatgat ttccagagtt   1451 tttgaaatag atggagatca aattacattt atgtccatat atgtatatta caactacaat   1511 ctaggcaagg aagtgagagc acatcttgtg gtctgctgag ttaggagggt atgattaaaa   1571 ggtaaagtct tatttcctaa cagtttcact taatatttac agaagaatct atatgtagcc   1631 tttgtaaagt gtaggattgt tatcatttaa aaacatcatg tacacttata tttgtattgt   1691 atacttggta agataaaatt ccacaaagta ggaatggggc ctcacataca cattgccatt   1751 cctattataa ttggacaatc caccacggtg ctaatgcagt gctgaatggc tcctactgga   1811 cctctcgata gaacactcta caaagtacga gtctctctct cccttccagg tgcatctcca   1871 cacacacagc actaagtgtt caatgcattt tctttaagga aagaagaatc ttttttttcta  1931 gaggtcaact ttcagtcaac tctagcacag cgggagtgac tgctgcatct taaaaggcag   1991 ccaaacagta ttcatttttt aatctaaatt tcaaaatcac tgtctgcctt tatcacatgg   2051 caattttgtg gtaaaataat ggaaatgact ggttctatca atattgtata aaagactctg   2111 aaacaattac atttatataa tatgtataca atattgtttt gtaaataagt gtctcctttt   2171 atatttactt tggtatattt ttacactaat gaaatttcaa atcattaaag tacaaagaca   2231 tgtcatgtat cacaaaaaag gtgactgctt ctatttcaga gtgaattagc agattcaata   2291 gtggtcttaa aactctgtat gttaagatta gaaggttata ttacaatcaa tttatgtatt   2351 ttttacatta tcaacttatg gtttcatggt ggctgtatct atgaatgtgg ctcccagtca   2411 aatttcaatg ccccaccatt ttaaaaatta caagcattac taaacatacc aacatgtatc   2471 taaagaaata caaatatggt atctcaataa cagctacttt tttattttat aatttgacaa   2531 tgaatacatt tcttttattt acttcagttt tataaattgg aactttgttt atcaaatgta   2591 ttgtactcat agctaaatga aattattttct tacataaaaa tgtgtagaaa ctataaatta   2651 aagtgttttc acatttttga aaggc                                          2676
```

<210> SEQ ID NO 4
<211> LENGTH: 376
<212> TYPE: PRT
<213> ORGANISM: Mus musculus

<400> SEQUENCE: 4

```
Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
                20                  25                  30

Asn Val Glu Lys Glu Gly Leu Cys Asn Ala Cys Ala Trp Arg Gln Asn
            35                  40                  45

Thr Arg Tyr Ser Arg Ile Glu Ala Ile Lys Ile Gln Ile Leu Ser Lys
        50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
```

<210> SEQ ID NO 5
<211> LENGTH: 1131
<212> TYPE: DNA
<213> ORGANISM: Rattus norvegicus
<220> FEATURE:
<221> NAME/KEY: CDS
<222> LOCATION: (1)..(1128)

<400> SEQUENCE: 5

| | | | | | | | | | | | | | | | | |
|---|---|---|---|---|---|---|---|---|---|---|---|---|---|---|---|---|
| atg | att | caa | aaa | ccg | caa | atg | tat | gtt | tat | att | tac | ctg | ttt | gtg | ctg | 48 |
| Met | Ile | Gln | Lys | Pro | Gln | Met | Tyr | Val | Tyr | Ile | Tyr | Leu | Phe | Val | Leu | |
| 1 | | | | 5 | | | | | 10 | | | | | 15 | | |
| att | gct | gct | ggc | cca | gtg | gat | cta | aat | gag | gac | agt | gag | aga | gag | gcg | 96 |
| Ile | Ala | Ala | Gly | Pro | Val | Asp | Leu | Asn | Glu | Asp | Ser | Glu | Arg | Glu | Ala | |
| | | | 20 | | | | | 25 | | | | | 30 | | | |
| aat | gtg | gaa | aaa | gag | ggg | ctg | tgt | aat | gcg | tgt | gcg | tgg | aga | caa | aac | 144 |
| Asn | Val | Glu | Lys | Glu | Gly | Leu | Cys | Asn | Ala | Cys | Ala | Trp | Arg | Gln | Asn | |
| | | 35 | | | | | 40 | | | | | 45 | | | | |
| aca | agg | tac | tcc | aga | ata | gaa | gcc | ata | aaa | att | caa | atc | ctc | agt | aaa | 192 |
| Thr | Arg | Tyr | Ser | Arg | Ile | Glu | Ala | Ile | Lys | Ile | Gln | Ile | Leu | Ser | Lys | |
| | 50 | | | | | 55 | | | | | 60 | | | | | |
| ctc | cgc | ctg | gaa | aca | gcg | cct | aac | atc | agc | aaa | gat | gct | ata | aga | caa | 240 |
| Leu | Arg | Leu | Glu | Thr | Ala | Pro | Asn | Ile | Ser | Lys | Asp | Ala | Ile | Arg | Gln | |
| 65 | | | | | 70 | | | | | 75 | | | | | 80 | |
| ctt | ctg | ccc | aga | gcg | cct | cca | ctc | cgg | gaa | ctg | atc | gat | cag | tac | gac | 288 |
| Leu | Leu | Pro | Arg | Ala | Pro | Pro | Leu | Arg | Glu | Leu | Ile | Asp | Gln | Tyr | Asp | |
| | | | | 85 | | | | | 90 | | | | | 95 | | |
| gtc | cag | agg | gat | gac | agc | agt | gac | ggc | tct | ttg | gaa | gat | gac | gat | tat | 336 |
| Val | Gln | Arg | Asp | Asp | Ser | Ser | Asp | Gly | Ser | Leu | Glu | Asp | Asp | Asp | Tyr | |
| | | | | | | 100 | | | | | 105 | | | | | 110 |
| cac | gct | acc | acg | gaa | aca | atc | att | acc | atg | cct | acc | gag | tct | gac | ttt | 384 |
| His | Ala | Thr | Thr | Glu | Thr | Ile | Ile | Thr | Met | Pro | Thr | Glu | Ser | Asp | Phe | |
| | | | 115 | | | | | 120 | | | | | 125 | | | |
| cta | atg | caa | gcg | gat | gga | aag | ccc | aaa | tgt | tgc | ttt | ttt | aaa | ttt | agc | 432 |
| Leu | Met | Gln | Ala | Asp | Gly | Lys | Pro | Lys | Cys | Cys | Phe | Phe | Lys | Phe | Ser | |
| | 130 | | | | | 135 | | | | | 140 | | | | | |
| tct | aaa | ata | cag | tac | aac | aaa | gtg | gta | aag | gcc | cag | ctg | tgg | ata | tat | 480 |
| Ser | Lys | Ile | Gln | Tyr | Asn | Lys | Val | Val | Lys | Ala | Gln | Leu | Trp | Ile | Tyr | |
| 145 | | | | | 150 | | | | | 155 | | | | | 160 | |
| ctg | aga | gcc | gtc | aag | act | cct | aca | aca | gtg | ttt | gtg | caa | atc | ctg | aga | 528 |
| Leu | Arg | Ala | Val | Lys | Thr | Pro | Thr | Thr | Val | Phe | Val | Gln | Ile | Leu | Arg | |
| | | | | 165 | | | | | 170 | | | | | 175 | | |
| ctc | atc | aaa | ccc | atg | aaa | gac | ggt | aca | agg | tat | acc | gga | atc | cga | tct | 576 |
| Leu | Ile | Lys | Pro | Met | Lys | Asp | Gly | Thr | Arg | Tyr | Thr | Gly | Ile | Arg | Ser | |
| | | | 180 | | | | | 185 | | | | | 190 | | | |
| ctg | aaa | ctt | gac | atg | agc | cca | ggc | act | ggt | att | tgg | cag | agt | att | gat | 624 |
| Leu | Lys | Leu | Asp | Met | Ser | Pro | Gly | Thr | Gly | Ile | Trp | Gln | Ser | Ile | Asp | |
| | | 195 | | | | | 200 | | | | | 205 | | | | |
| gtg | aag | aca | gtg | ttg | caa | aat | tgg | ctc | aaa | cag | cct | gaa | tcc | aac | tta | 672 |
| Val | Lys | Thr | Val | Leu | Gln | Asn | Trp | Leu | Lys | Gln | Pro | Glu | Ser | Asn | Leu | |
| | 210 | | | | | 215 | | | | | 220 | | | | | |
| ggc | att | gaa | atc | aaa | gct | ttg | gat | gag | aat | ggg | cat | gat | ctt | gct | gta | 720 |
| Gly | Ile | Glu | Ile | Lys | Ala | Leu | Asp | Glu | Asn | Gly | His | Asp | Leu | Ala | Val | |
| 225 | | | | | 230 | | | | | 235 | | | | | 240 | |
| acc | ttc | cca | gga | cca | gga | gaa | gat | ggg | ctg | aat | ccc | ttt | tta | gaa | gtc | 768 |
| Thr | Phe | Pro | Gly | Pro | Gly | Glu | Asp | Gly | Leu | Asn | Pro | Phe | Leu | Glu | Val | |
| | | | | 245 | | | | | 250 | | | | | 255 | | |
| aaa | gta | aca | gac | aca | ccc | aag | agg | tcc | cgg | aga | gac | ttt | ggg | ctt | gac | 816 |
| Lys | Val | Thr | Asp | Thr | Pro | Lys | Arg | Ser | Arg | Arg | Asp | Phe | Gly | Leu | Asp | |

```
                 260                 265                 270
tgc gat gaa cac tcc acg gaa tcg cgg tgc tgt cgc tac ccc ctc acg      864
Cys Asp Glu His Ser Thr Glu Ser Arg Cys Cys Arg Tyr Pro Leu Thr
        275                 280                 285 gtc gat ttc gaa gcc ttt gga tgg gac tgg att att gca ccc aaa aga      912
Val Asp Phe Glu Ala Phe Gly Trp Asp Trp Ile Ile Ala Pro Lys Arg
290                 295                 300 tat aag gct aat tac tgc tct gga gag tgt gaa ttt gtg ttc tta caa      960
Tyr Lys Ala Asn Tyr Cys Ser Gly Glu Cys Glu Phe Val Phe Leu Gln
305                 310                 315                 320 aaa tat ccg cat act cat ctt gtg cac caa gca aac ccc aga ggc tcg     1008
Lys Tyr Pro His Thr His Leu Val His Gln Ala Asn Pro Arg Gly Ser
                325                 330                 335 gca ggc cct tgc tgc acg cca aca aaa atg tct ccc att aat atg cta     1056
Ala Gly Pro Cys Cys Thr Pro Thr Lys Met Ser Pro Ile Asn Met Leu
            340                 345                 350 tat ttt aat ggc aaa gaa caa ata ata tat ggg aaa att cca gcc atg     1104
Tyr Phe Asn Gly Lys Glu Gln Ile Ile Tyr Gly Lys Ile Pro Ala Met
                355                 360                 365 gta gta gac cgg tgt ggg tgc tcg tga                                  1131
Val Val Asp Arg Cys Gly Cys Ser
    370                 375

<210> SEQ ID NO 6
<211> LENGTH: 376
<212> TYPE: PRT
<213> ORGANISM: Rattus norvegicus

<400> SEQUENCE: 6

Met Ile Gln Lys Pro Gln Met Tyr Val Tyr Ile Tyr Leu Phe Val Leu
1               5                   10                  15

Ile Ala Ala Gly Pro Val Asp Leu Asn Glu Asp Ser Glu Arg Glu Ala
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220
```

-continued

```
Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
            245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
            275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
            355                 360                 365

Val Val Asp Arg Cys Gly Cys Ser
    370                 375

<210> SEQ ID NO 7
<211> LENGTH: 1128
<212> TYPE: DNA
<213> ORGANISM: Gallus gallus
<220> FEATURE:
<221> NAME/KEY: CDS
<222> LOCATION: (1)..(1125)

<400> SEQUENCE: 7 atg caa aag ctg gca gtc tat gtt tat att tac ctg ttc atg cag atc      48
Met Gln Lys Leu Ala Val Tyr Val Tyr Ile Tyr Leu Phe Met Gln Ile
1               5                   10                  15 gcg gtt gat ccg gtg gct ctg gat ggc agt agt cag ccc aca gag aac      96
Ala Val Asp Pro Val Ala Leu Asp Gly Ser Ser Gln Pro Thr Glu Asn
            20                  25                  30 gct gaa aaa gac gga ctg tgc aat gct tgt acg tgg aga cag aat aca     144
Ala Glu Lys Asp Gly Leu Cys Asn Ala Cys Thr Trp Arg Gln Asn Thr
        35                  40                  45 aaa tcc tcc aga ata gaa gcc ata aaa att caa atc ctc agc aaa ctg     192
Lys Ser Ser Arg Ile Glu Ala Ile Lys Ile Gln Ile Leu Ser Lys Leu
    50                  55                  60 cgc ctg gaa caa gca cct aac att agc agg gac gtt att aag cag ctt     240
Arg Leu Glu Gln Ala Pro Asn Ile Ser Arg Asp Val Ile Lys Gln Leu
65                  70                  75                  80 tta ccc aaa gct cct cca ctg cag gaa ctg att gat cag tat gat gtc     288
Leu Pro Lys Ala Pro Pro Leu Gln Glu Leu Ile Asp Gln Tyr Asp Val
                85                  90                  95 cag agg gac gac agt agc gat ggc tct ttg gaa gac gat gac tat cat     336
Gln Arg Asp Asp Ser Ser Asp Gly Ser Leu Glu Asp Asp Asp Tyr His
            100                 105                 110 gcc aca acc gag acg att atc aca atg cct acg gag tct gat ttt ctt     384
Ala Thr Thr Glu Thr Ile Ile Thr Met Pro Thr Glu Ser Asp Phe Leu
        115                 120                 125 gta caa atg gag gga aaa cca aaa tgt tgc ttc ttt aag ttt agc tct     432
Val Gln Met Glu Gly Lys Pro Lys Cys Cys Phe Phe Lys Phe Ser Ser
130                 135                 140 aaa ata caa tat aac aaa gta gta aag gca caa tta tgg ata tac ttg     480
```

-continued

```
Lys Ile Gln Tyr Asn Lys Val Lys Ala Gln Leu Trp Ile Tyr Leu
145                 150                 155                 160 agg caa gtc caa aaa cct aca acg gtg ttt gtg cag atc ctg aga ctc         528
Arg Gln Val Gln Lys Pro Thr Thr Val Phe Val Gln Ile Leu Arg Leu
                165                 170                 175 att aag ccc atg aaa gac ggt aca aga tat act gga att cga tct ttg         576
Ile Lys Pro Met Lys Asp Gly Thr Arg Tyr Thr Gly Ile Arg Ser Leu
            180                 185                 190 aaa ctt gac atg aac cca ggc act ggt atc tgg cag agt att gat gtg         624
Lys Leu Asp Met Asn Pro Gly Thr Gly Ile Trp Gln Ser Ile Asp Val
        195                 200                 205 aag aca gtg ctg caa aat tgg ctc aaa cag cct gaa tcc aat tta ggc         672
Lys Thr Val Leu Gln Asn Trp Leu Lys Gln Pro Glu Ser Asn Leu Gly
    210                 215                 220 atc gaa ata aaa gct ttt gat gag act gga cga gat ctt gct gtc aca         720
Ile Glu Ile Lys Ala Phe Asp Glu Thr Gly Arg Asp Leu Ala Val Thr
225                 230                 235                 240 ttc cca gga cca gga gaa gat gga ttg aac cca ttt tta gag gtc aga         768
Phe Pro Gly Pro Gly Glu Asp Gly Leu Asn Pro Phe Leu Glu Val Arg
                245                 250                 255 gtt aca gac aca ccg aaa cgg tcc cgc aga gat ttt ggc ctt gac tgt         816
Val Thr Asp Thr Pro Lys Arg Ser Arg Arg Asp Phe Gly Leu Asp Cys
            260                 265                 270 gat gag cac tca acg gaa tcc cga tgt tgt cgc tac ccg ctg aca gtg         864
Asp Glu His Ser Thr Glu Ser Arg Cys Cys Arg Tyr Pro Leu Thr Val
        275                 280                 285 gat ttc gaa gct ttt gga tgg gac tgg att ata gca cct aaa aga tac         912
Asp Phe Glu Ala Phe Gly Trp Asp Trp Ile Ile Ala Pro Lys Arg Tyr
    290                 295                 300 aaa gcc aat tac tgc tcc gga gaa tgc gaa ttt gtg ttt cta cag aaa         960
Lys Ala Asn Tyr Cys Ser Gly Glu Cys Glu Phe Val Phe Leu Gln Lys
305                 310                 315                 320 tac ccg cac act cac ctg gta cac caa gca aat ccc aga ggc tca gca        1008
Tyr Pro His Thr His Leu Val His Gln Ala Asn Pro Arg Gly Ser Ala
                325                 330                 335 ggc cct tgc tgc aca ccc acc aag atg tcc cct ata aac atg ctg tat        1056
Gly Pro Cys Cys Thr Pro Thr Lys Met Ser Pro Ile Asn Met Leu Tyr
            340                 345                 350 ttc aat gga aaa gaa caa ata ata tat gga aag ata cca gcc atg gtt        1104
Phe Asn Gly Lys Glu Gln Ile Ile Tyr Gly Lys Ile Pro Ala Met Val
        355                 360                 365 gta gat cgt tgc ggg tgc tca tga                                        1128
Val Asp Arg Cys Gly Cys Ser
    370                 375
```

<210> SEQ ID NO 8
<211> LENGTH: 375
<212> TYPE: PRT
<213> ORGANISM: Gallus gallus

<400> SEQUENCE: 8

```
Met Gln Lys Leu Ala Val Tyr Val Tyr Ile Tyr Leu Phe Met Gln Ile
1               5                   10                  15

Ala Val Asp Pro Val Ala Leu Asp Gly Ser Ser Gln Pro Thr Glu Asn
            20                  25                  30

Ala Glu Lys Asp Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60
```

-continued

```
Arg Leu Glu Gln Ala Pro Asn Ile Ser Arg Asp Val Ile Lys Gln Leu
 65                  70                  75                  80

Leu Pro Lys Ala Pro Pro Leu Gln Glu Leu Ile Asp Gln Tyr Asp Val
                 85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Val Gln Met Glu Gly Lys Pro Lys Cys Cys Phe Phe Lys Phe Ser Ser
        130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210                 215                 220

Ile Glu Ile Lys Ala Phe Asp Glu Thr Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
        370                 375
```

```
<210> SEQ ID NO 9
<211> LENGTH: 1128
<212> TYPE: DNA
<213> ORGANISM: Baboon
<220> FEATURE:
<221> NAME/KEY: CDS
<222> LOCATION: (1)..(1125)

<400> SEQUENCE: 9 atg caa aaa ctg caa ctc tgt gtt tat att tac ctg ttt atg ctg att    48
Met Gln Lys Leu Gln Leu Cys Val Tyr Ile Tyr Leu Phe Met Leu Ile
  1               5                  10                  15 gtt gct ggt cca gtg gat cta aat gag aac agt gag caa aaa gaa aat    96
Val Ala Gly Pro Val Asp Leu Asn Glu Asn Ser Glu Gln Lys Glu Asn
             20                  25                  30
```

```
gtg gaa aaa gag ggg ctg tgt aat gca tgt act tgg aga caa aac act      144
Val Glu Lys Glu Gly Leu Cys Asn Ala Cys Thr Trp Arg Gln Asn Thr
         35                  40                  45 aaa tct tca aga ata gaa gcc att aaa ata caa atc ctc agt aaa ctt      192
Lys Ser Ser Arg Ile Glu Ala Ile Lys Ile Gln Ile Leu Ser Lys Leu
 50                  55                  60 cgt ctg gaa aca gct cct aac atc agc aaa gat gct ata aga caa ctt      240
Arg Leu Glu Thr Ala Pro Asn Ile Ser Lys Asp Ala Ile Arg Gln Leu
 65                  70                  75                  80 tta ccc aaa gcg cct cca ctc cgg gaa ctg att gat cag tat gat gtc      288
Leu Pro Lys Ala Pro Pro Leu Arg Glu Leu Ile Asp Gln Tyr Asp Val
                 85                  90                  95 cag agg gat gac agc agc gat ggc tct ttg gaa gat gac gat tat cac      336
Gln Arg Asp Asp Ser Ser Asp Gly Ser Leu Glu Asp Asp Asp Tyr His
             100                 105                 110 gct aca acg gaa aca atc att acc atg cct aca gag tct gat ttt tta      384
Ala Thr Thr Glu Thr Ile Ile Thr Met Pro Thr Glu Ser Asp Phe Leu
         115                 120                 125 atg caa gtg gat gga aaa ccc aaa tgt tgc ttc ttt aaa ttt agc tct      432
Met Gln Val Asp Gly Lys Pro Lys Cys Cys Phe Phe Lys Phe Ser Ser
130                 135                 140 aaa ata caa tac aat aaa gtg gta aag gcc caa cta tgg ata tat ttg      480
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc      528
Arg Pro Val Glu Thr Pro Thr Thr Val Phe Val Gln Ile Leu Arg Leu
                 165                 170                 175 atc aaa cct atg aaa gac ggt aca agg tat act gga atc cga tct ctg      576
Ile Lys Pro Met Lys Asp Gly Thr Arg Tyr Thr Gly Ile Arg Ser Leu
             180                 185                 190 aaa ctt gac atg aac cca ggc act ggt att tgg cag agc att gat gtg      624
Lys Leu Asp Met Asn Pro Gly Thr Gly Ile Trp Gln Ser Ile Asp Val
         195                 200                 205 aag aca gtg ttg caa aat tgg ctc aaa caa cct gaa tcc aac tta ggc      672
Lys Thr Val Leu Gln Asn Trp Leu Lys Gln Pro Glu Ser Asn Leu Gly
210                 215                 220 att gaa ata aaa gct tta gat gag aat ggt cat gat ctt gct gta acc      720
Ile Glu Ile Lys Ala Leu Asp Glu Asn Gly His Asp Leu Ala Val Thr
225                 230                 235                 240 ttc cca gga cca gga gaa gat ggg ctg aat ccc ttt tta gag gtc aag      768
Phe Pro Gly Pro Gly Glu Asp Gly Leu Asn Pro Phe Leu Glu Val Lys
                 245                 250                 255 gta aca gac aca ccc aaa aga tcc aga agg gat ttt ggt ctt gac tgt      816
Val Thr Asp Thr Pro Lys Arg Ser Arg Arg Asp Phe Gly Leu Asp Cys
             260                 265                 270 gat gag cac tca aca gaa tcg cga tgc tgt cgt tac cct cta act gtg      864
Asp Glu His Ser Thr Glu Ser Arg Cys Cys Arg Tyr Pro Leu Thr Val
         275                 280                 285 gat ttt gaa gct ctt gga tgg gat tgg att atc gct cct aaa aga tat      912
Asp Phe Glu Ala Leu Gly Trp Asp Trp Ile Ile Ala Pro Lys Arg Tyr
     290                 295                 300 aag gcc aat tac tgc tct gga gag tgt gaa ttt gta ttt tta caa aaa      960
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca     1008
Tyr Pro His Thr His Leu Val His Gln Ala Asn Pro Arg Gly Ser Ala
                 325                 330                 335 ggc cct tgc tgt act ccc aca aag atg tct cca att aat atg cta tat     1056
Gly Pro Cys Cys Thr Pro Thr Lys Met Ser Pro Ile Asn Met Leu Tyr
             340                 345                 350
```

```
ttt aat ggc aaa gaa caa ata ata tat ggg aaa att cca gcc atg gta     1104
Phe Asn Gly Lys Glu Gln Ile Ile Tyr Gly Lys Ile Pro Ala Met Val
        355                 360                 365 gta gac cgc tgc ggg tgc tca tga                                     1128
Val Asp Arg Cys Gly Cys Ser
370                 375
```

<210> SEQ ID NO 10
<211> LENGTH: 375
<212> TYPE: PRT
<213> ORGANISM: Baboon

<400> SEQUENCE: 10

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Leu Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335
```

```
Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
    370                 375

<210> SEQ ID NO 11
<211> LENGTH: 1128
<212> TYPE: DNA
<213> ORGANISM: Bovine
<220> FEATURE:
<221> NAME/KEY: CDS
<222> LOCATION: (1)..(1125)

<400> SEQUENCE: 11 atg caa aaa ctg caa atc tct gtt tat att tac cta ttt atg ctg att    48
Met Gln Lys Leu Gln Ile Ser Val Tyr Ile Tyr Leu Phe Met Leu Ile
1               5                   10                  15 gtt gct ggc cca gtg gat ctg aat gag aac agc gag cag aag gaa aat    96
Val Ala Gly Pro Val Asp Leu Asn Glu Asn Ser Glu Gln Lys Glu Asn
                20                  25                  30 gtg gaa aaa gag ggg ctg tgt aat gca tgt ttg tgg agg gaa aac act   144
Val Glu Lys Glu Gly Leu Cys Asn Ala Cys Leu Trp Arg Glu Asn Thr
            35                  40                  45 aca tcg tca aga cta gaa gcc ata aaa atc caa atc ctc agt aaa ctt   192
Thr Ser Ser Arg Leu Glu Ala Ile Lys Ile Gln Ile Leu Ser Lys Leu
        50                  55                  60 cgc ctg gaa aca gct cct aac atc agc aaa gat gct atc aga caa ctt   240
Arg Leu Glu Thr Ala Pro Asn Ile Ser Lys Asp Ala Ile Arg Gln Leu
65                  70                  75                  80 ttg ccc aag gct cct cca ctc ctg gaa ctg att gat cag ttc gat gtc   288
Leu Pro Lys Ala Pro Pro Leu Leu Glu Leu Ile Asp Gln Phe Asp Val
                85                  90                  95 cag aga gat gcc agc agt gac ggc tcc ttg gaa gac gat gac tac cac   336
Gln Arg Asp Ala Ser Ser Asp Gly Ser Leu Glu Asp Asp Asp Tyr His
                100                 105                 110 gcc agg acg gaa acg gtc att acc atg ccc acg gag tct gat ctt cta   384
Ala Arg Thr Glu Thr Val Ile Thr Met Pro Thr Glu Ser Asp Leu Leu
            115                 120                 125 acg caa gtg gaa gga aaa ccc aaa tgt tgc ttc ttt aaa ttt agc tct   432
Thr Gln Val Glu Gly Lys Pro Lys Cys Cys Phe Phe Lys Phe Ser Ser
        130                 135                 140 aag ata caa tac aat aaa cta gta aag gcc caa ctg tgg ata tat ctg   480
Lys Ile Gln Tyr Asn Lys Leu Val Lys Ala Gln Leu Trp Ile Tyr Leu
145                 150                 155                 160 agg cct gtc aag act cct gcg aca gtg ttt gtg caa atc ctg aga ctc   528
Arg Pro Val Lys Thr Pro Ala Thr Val Phe Val Gln Ile Leu Arg Leu
                165                 170                 175 atc aaa ccc atg aaa gac ggt aca agg tat act gga atc cga tct ctg   576
Ile Lys Pro Met Lys Asp Gly Thr Arg Tyr Thr Gly Ile Arg Ser Leu
                180                 185                 190 aaa ctt gac atg aac cca ggc act ggt att tgg cag agc att gat gtg   624
Lys Leu Asp Met Asn Pro Gly Thr Gly Ile Trp Gln Ser Ile Asp Val
            195                 200                 205 aag aca gtg ttg cag aac tgg ctc aaa caa cct gaa tcc aac tta ggc   672
Lys Thr Val Leu Gln Asn Trp Leu Lys Gln Pro Glu Ser Asn Leu Gly
        210                 215                 220 att gaa atc aaa gct tta gat gag aat ggc cat gat ctt gct gta acc   720
Ile Glu Ile Lys Ala Leu Asp Glu Asn Gly His Asp Leu Ala Val Thr
```

```
                                                                                         768
ttc cca gaa cca gga gaa gat gga ctg act ccc ttt tta gaa gtc aag
Phe Pro Glu Pro Gly Glu Asp Gly Leu Thr Pro Phe Leu Glu Val Lys
                245                 250                 255

816
gta aca gac aca cca aaa aga tct agg aga gat ttt ggg ctt gat tgt
Val Thr Asp Thr Pro Lys Arg Ser Arg Arg Asp Phe Gly Leu Asp Cys
            260                 265                 270

864
gat gaa cac tcc aca gaa tct cga tgc tgt cgt tac cct cta act gtg
Asp Glu His Ser Thr Glu Ser Arg Cys Cys Arg Tyr Pro Leu Thr Val
        275                 280                 285

912
gat ttt gaa gct ttt gga tgg gat tgg att att gca cct aaa aga tat
Asp Phe Glu Ala Phe Gly Trp Asp Trp Ile Ile Ala Pro Lys Arg Tyr
    290                 295                 300

960
aag gcc aat tac tgc tct gga gaa tgt gaa ttt gta ttt ttg caa aag
Lys Ala Asn Tyr Cys Ser Gly Glu Cys Glu Phe Val Phe Leu Gln Lys
305                 310                 315                 320

1008
tat cct cat acc cat ctt gtg cac caa gca aac ccc aga ggt tca gcc
Tyr Pro His Thr His Leu Val His Gln Ala Asn Pro Arg Gly Ser Ala
                325                 330                 335

1056
ggc ccc tgc tgt act cct aca aag atg tct cca att aat atg cta tat
Gly Pro Cys Cys Thr Pro Thr Lys Met Ser Pro Ile Asn Met Leu Tyr
            340                 345                 350

1104
ttt aat ggc gaa gga caa ata ata tac ggg aag att cca gcc atg gta
Phe Asn Gly Glu Gly Gln Ile Ile Tyr Gly Lys Ile Pro Ala Met Val
        355                 360                 365

1128
gta gat cgc tgt ggg tgt tca tga
Val Asp Arg Cys Gly Cys Ser
    370                 375

<210> SEQ ID NO 12
<211> LENGTH: 375
<212> TYPE: PRT
<213> ORGANISM: Bovine

<400> SEQUENCE: 12

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175
```

```
Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Glu Gly Gln Ile Ile Tyr Gly Lys Ile Pro Ala Met Val
        355                 360                 365

Val Asp Arg Cys Gly Cys Ser
    370                 375

<210> SEQ ID NO 13
<211> LENGTH: 1128
<212> TYPE: DNA
<213> ORGANISM: Porcine
<220> FEATURE:
<221> NAME/KEY: CDS
<222> LOCATION: (1)..(1125)

<400> SEQUENCE: 13 atg caa aaa ctg caa atc tat gtt tat att tac ctg ttt atg ctg att    48
Met Gln Lys Leu Gln Ile Tyr Val Tyr Ile Tyr Leu Phe Met Leu Ile
1               5                   10                  15 gtt gct ggt ccc gtg gat ctg aat gag aac agc gag caa aag gaa aat    96
Val Ala Gly Pro Val Asp Leu Asn Glu Asn Ser Glu Gln Lys Glu Asn
                20                  25                  30 gtg gaa aaa gag ggg ctg tgt aat gca tgt atg tgg aga caa aac act   144
Val Glu Lys Glu Gly Leu Cys Asn Ala Cys Met Trp Arg Gln Asn Thr
            35                  40                  45 aaa tct tca aga cta gaa gcc ata aaa att caa atc ctc agt aaa ctt   192
Lys Ser Ser Arg Leu Glu Ala Ile Lys Ile Gln Ile Leu Ser Lys Leu
        50                  55                  60 cgc ctg gaa aca gct cct aac att agc aaa gat gct ata aga caa ctt   240
Arg Leu Glu Thr Ala Pro Asn Ile Ser Lys Asp Ala Ile Arg Gln Leu
65                  70                  75                  80 ttg ccc aaa gct cct cca ctc cgg gaa ctg att gat cag tac gat gtc   288
Leu Pro Lys Ala Pro Pro Leu Arg Glu Leu Ile Asp Gln Tyr Asp Val
                85                  90                  95 cag aga gat gac agc agt gat ggc tcc ttg gaa gat gat gat tat cac   336
Gln Arg Asp Asp Ser Ser Asp Gly Ser Leu Glu Asp Asp Asp Tyr His
                100                 105                 110 gct acg acg gaa acg atc att acc atg cct aca gag tct gat ctt cta   384
```

```
                Ala Thr Thr Glu Thr Ile Ile Thr Met Pro Thr Glu Ser Asp Leu Leu
                                115                 120                 125 atg caa gtg gaa gga aaa ccc aaa tgc tgc ttc ttt aaa ttt agc tct             432
Met Gln Val Glu Gly Lys Pro Lys Cys Cys Phe Phe Lys Phe Ser Ser
130                 135                 140 aaa ata caa tac aat aaa gta gta aag gcc caa ctg tgg ata tat ctg             480
Lys Ile Gln Tyr Asn Lys Val Val Lys Ala Gln Leu Trp Ile Tyr Leu
145                 150                 155                 160 aga ccc gtc aag act cct aca aca gtg ttt gtg caa atc ctg aga ctc             528
Arg Pro Val Lys Thr Pro Thr Thr Val Phe Val Gln Ile Leu Arg Leu
                165                 170                 175 atc aaa ccc atg aaa gac ggt aca agg tat act gga atc cga tct ctg             576
Ile Lys Pro Met Lys Asp Gly Thr Arg Tyr Thr Gly Ile Arg Ser Leu
                180                 185                 190 aaa ctt gac atg aac cca ggc act ggt att tgg cag agc att gat gtg             624
Lys Leu Asp Met Asn Pro Gly Thr Gly Ile Trp Gln Ser Ile Asp Val
                195                 200                 205 aag aca gtg ttg caa aat tgg ctc aaa caa cct gaa tcc aac tta ggc             672
Lys Thr Val Leu Gln Asn Trp Leu Lys Gln Pro Glu Ser Asn Leu Gly
210                 215                 220 att gaa atc aaa gct tta gat gag aat ggt cat gat ctt gct gta acc             720
Ile Glu Ile Lys Ala Leu Asp Glu Asn Gly His Asp Leu Ala Val Thr
225                 230                 235                 240 ttc cca gga cca gga gaa gat ggg ctg aat ccc ttt tta gaa gtc aag             768
Phe Pro Gly Pro Gly Glu Asp Gly Leu Asn Pro Phe Leu Glu Val Lys
                245                 250                 255 gta aca gac aca cca aaa aga tcc agg aga gat ttt gga ctc gac tgt             816
Val Thr Asp Thr Pro Lys Arg Ser Arg Arg Asp Phe Gly Leu Asp Cys
                260                 265                 270 gat gag cac tca aca gaa tct cga tgc tgt cgt tac cct cta act gtg             864
Asp Glu His Ser Thr Glu Ser Arg Cys Cys Arg Tyr Pro Leu Thr Val
                275                 280                 285 gat ttt gaa gct ttt gga tgg gac tgg att att gca ccc aaa aga tat             912
Asp Phe Glu Ala Phe Gly Trp Asp Trp Ile Ile Ala Pro Lys Arg Tyr
                290                 295                 300 aag gcc aat tac tgc tct gga gag tgt gaa ttt gta ttt tta caa aaa             960
Lys Ala Asn Tyr Cys Ser Gly Glu Cys Glu Phe Val Phe Leu Gln Lys
305                 310                 315                 320 tac cct cac act cat ctt gtg cac caa gca aac ccc aga ggt tca gca            1008
Tyr Pro His Thr His Leu Val His Gln Ala Asn Pro Arg Gly Ser Ala
                325                 330                 335 ggc ccc tgc tgt act ccc aca aag atg tct cca atc aat atg cta tat            1056
Gly Pro Cys Cys Thr Pro Thr Lys Met Ser Pro Ile Asn Met Leu Tyr
                340                 345                 350 ttt aat ggc aaa gaa caa ata ata tat ggg aaa att cca gcc atg gta            1104
Phe Asn Gly Lys Glu Gln Ile Ile Tyr Gly Lys Ile Pro Ala Met Val
                355                 360                 365 gta gat cgc tgt ggg tgc tca tga                                            1128
Val Asp Arg Cys Gly Cys Ser
                370                 375

<210> SEQ ID NO 14
<211> LENGTH: 375
<212> TYPE: PRT
<213> ORGANISM: Porcine

<400> SEQUENCE: 14

Met Gln Lys Leu Gln Ile Tyr Val Tyr Ile Tyr Leu Phe Met Leu Ile
1               5                   10                  15

Val Ala Gly Pro Val Asp Leu Asn Glu Asn Ser Glu Gln Lys Glu Asn
```

```
                    20                  25                  30
Val Glu Lys Glu Gly Leu Cys Asn Ala Cys Met Trp Arg Gln Asn Thr
             35                  40                  45

Lys Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Tyr His
             100                 105                 110

Ala Thr Thr Glu Thr Ile Ile Thr Met Pro Thr Glu Ser Asp Leu Leu
             115                 120                 125

Met Gln Val Glu Gly Lys Pro Lys Cys Cys Phe Phe Lys Phe Ser Ser
             130                 135                 140

Lys Ile Gln Tyr Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                 165                 170                 175

Ile Lys Pro Met Lys Asp Gly Thr Arg Tyr Thr Gly Ile Arg Ser Leu
             180                 185                 190

Lys Leu Asp Met Asn Pro Gly Thr Gly Ile Trp Gln Ser Ile Asp Val
             195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                 245                 250                 255

Val Thr Asp Thr Pro Lys Arg Ser Arg Arg Asp Phe Gly Leu Asp Cys
             260                 265                 270

Asp Glu His Ser Thr Glu Ser Arg Cys Cys Arg Tyr Pro Leu Thr Val
             275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                 325                 330                 335

Gly Pro Cys Cys Thr Pro Thr Lys Met Ser Pro Ile Asn Met Leu Tyr
             340                 345                 350

Phe Asn Gly Lys Glu Gln Ile Ile Tyr Gly Lys Ile Pro Ala Met Val
             355                 360                 365

Val Asp Arg Cys Gly Cys Ser
    370                 375

<210> SEQ ID NO 15
<211> LENGTH: 1128
<212> TYPE: DNA
<213> ORGANISM: Ovine
<220> FEATURE:
<221> NAME/KEY: CDS
<222> LOCATION: (1)..(1125)

<400> SEQUENCE: 15
```

```
-continued atg caa aaa ctg caa atc ttt gtt tat att tac cta ttt atg ctg ctt    48
Met Gln Lys Leu Gln Ile Phe Val Tyr Ile Tyr Leu Phe Met Leu Leu
1               5                   10                  15 gtt gct ggc cca gtg gat ctg aat gag aac agc gag cag aag gaa aat    96
Val Ala Gly Pro Val Asp Leu Asn Glu Asn Ser Glu Gln Lys Glu Asn
            20                  25                  30 gtg gaa aaa aag ggg ctg tgt aat gca tgc ttg tgg aga caa aac aat   144
Val Glu Lys Lys Gly Leu Cys Asn Ala Cys Leu Trp Arg Gln Asn Asn
        35                  40                  45 aaa tcc tca aga cta gaa gcc ata aaa atc caa atc ctc agt aag ctt   192
Lys Ser Ser Arg Leu Glu Ala Ile Lys Ile Gln Ile Leu Ser Lys Leu
    50                  55                  60 cgc ctg gaa aca gct cct aac atc agc aaa gat gct ata aga caa ctt   240
Arg Leu Glu Thr Ala Pro Asn Ile Ser Lys Asp Ala Ile Arg Gln Leu
65                  70                  75                  80 ttg ccc aag gct cct cca ctc cgg gaa ctg att gat cag tac gat gtc   288
Leu Pro Lys Ala Pro Pro Leu Arg Glu Leu Ile Asp Gln Tyr Asp Val
                85                  90                  95 cag aga gat gac agc agc gac ggc tcc ttg gaa gac gat gac tac cac   336
Gln Arg Asp Asp Ser Ser Asp Gly Ser Leu Glu Asp Asp Asp Tyr His
            100                 105                 110 gtt acg acg gaa acg gtc att acc atg ccc acg gag tct gat ctt cta   384
Val Thr Thr Glu Thr Val Ile Thr Met Pro Thr Glu Ser Asp Leu Leu
        115                 120                 125 gca gaa gtg caa gaa aaa ccc aaa tgt tgc ttc ttt aaa ttt agc tct   432
Ala Glu Val Gln Glu Lys Pro Lys Cys Cys Phe Phe Lys Phe Ser Ser
    130                 135                 140 aag ata caa cac aat aaa gta gta aag gcc caa ctg tgg ata tat ctg   480
Lys Ile Gln His Asn Lys Val Val Lys Ala Gln Leu Trp Ile Tyr Leu
145                 150                 155                 160 aga cct gtc aag act cct aca aca gtg ttt gtg caa atc ctg aga ctc   528
Arg Pro Val Lys Thr Pro Thr Thr Val Phe Val Gln Ile Leu Arg Leu
                165                 170                 175 atc aaa ccc atg aaa gac ggt aca agg tat act gga atc cga tct ctg   576
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg   624
Lys Leu Asp Met Asn Pro Gly Thr Gly Ile Trp Gln Ser Ile Asp Val
        195                 200                 205 aag aca gtg ttg caa aac tgg ctc aaa caa cct gaa tcc aac tta ggc   672
Lys Thr Val Leu Gln Asn Trp Leu Lys Gln Pro Glu Ser Asn Leu Gly
    210                 215                 220 att gaa atc aaa gct tta gat gag aat ggt cat gat ctt gct gta acc   720
Ile Glu Ile Lys Ala Leu Asp Glu Asn Gly His Asp Leu Ala Val Thr
225                 230                 235                 240 ttc cca gaa cca gga gaa gaa gga ctg aat cct ttt tta gaa gtc aag   768
Phe Pro Glu Pro Gly Glu Glu Gly Leu Asn Pro Phe Leu Glu Val Lys
                245                 250                 255 gta aca gac aca cca aaa aga tct agg aga gat ttt ggg ctt gat tgt   816
Val Thr Asp Thr Pro Lys Arg Ser Arg Arg Asp Phe Gly Leu Asp Cys
            260                 265                 270 gat gag cac tcc aca gaa tct cga tgc tgt cgt tac cct cta act gtg   864
Asp Glu His Ser Thr Glu Ser Arg Cys Cys Arg Tyr Pro Leu Thr Val
        275                 280                 285 gat ttt gaa gct ttt gga tgg gat tgg att att gca cct aaa aga tat   912
Asp Phe Glu Ala Phe Gly Trp Asp Trp Ile Ile Ala Pro Lys Arg Tyr
    290                 295                 300 aag gcc aat tac tgc tct gga gaa tgt gaa ttt tta ttt ttg caa aag   960
Lys Ala Asn Tyr Cys Ser Gly Glu Cys Glu Phe Leu Phe Leu Gln Lys
305                 310                 315                 320
```

```
tat cct cat acc cat ctt gtg cac caa gca aac ccc aaa ggt tca gcc      1008
Tyr Pro His Thr His Leu Val His Gln Ala Asn Pro Lys Gly Ser Ala
            325                 330                 335 ggc cct tgc tgt act cct aca aag atg tct cca att aat atg cta tat      1056
Gly Pro Cys Cys Thr Pro Thr Lys Met Ser Pro Ile Asn Met Leu Tyr
            340                 345                 350 ttt aat ggc aaa gaa caa ata ata tat ggg aag att cca ggc atg gta      1104
Phe Asn Gly Lys Glu Gln Ile Ile Tyr Gly Lys Ile Pro Gly Met Val
            355                 360                 365 gta gat cgc tgt ggg tgc tca tga                                      1128
Val Asp Arg Cys Gly Cys Ser
    370             375

<210> SEQ ID NO 16
<211> LENGTH: 375
<212> TYPE: PRT
<213> ORGANISM: Ovine

<400> SEQUENCE: 16

Met Gln Lys Leu Gln Ile Phe Val Tyr Ile Tyr Leu Phe Met Leu Leu
1               5                   10                  15

Val Ala Gly Pro Val Asp Leu Asn Glu Asn Ser Glu Gln Lys Glu Asn
            20                  25                  30

Val Glu Lys Lys Gly Leu Cys Asn Ala Cys Leu Trp Arg Gln Asn Asn
        35                  40                  45

Lys Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Val Thr Thr Glu Thr Val Ile Thr Met Pro Thr Glu Ser Asp Leu Leu
        115                 120                 125

Ala Glu Val Gln Glu Lys Pro Lys Cys Cys Phe Phe Lys Phe Ser Ser
    130                 135                 140

Lys Ile Gln His Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285
```

```
Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Leu Phe Leu Gln Lys
305                 310                 315                 320

Tyr Pro His Thr His Leu Val His Gln Ala Asn Pro Lys Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Gly Met Val
        355                 360                 365

Val Asp Arg Cys Gly Cys Ser
    370                 375

<210> SEQ ID NO 17
<211> LENGTH: 1128
<212> TYPE: DNA
<213> ORGANISM: Meleagris gallopavo
<220> FEATURE:
<221> NAME/KEY: CDS
<222> LOCATION: (1)..(1125)

<400> SEQUENCE: 17
```

| | | | | | | | | | | | | | | | | |
|---|---|---|---|---|---|---|---|---|---|---|---|---|---|---|---|---|
| atg | caa | aag | cta | gca | gtc | tat | gtt | tat | att | tac | ctg | ttc | atg | cag | att | 48 |
| Met | Gln | Lys | Leu | Ala | Val | Tyr | Val | Tyr | Ile | Tyr | Leu | Phe | Met | Gln | Ile | |
| 1 | | | | 5 | | | | | 10 | | | | | 15 | | |
| tta | gtt | cat | ccg | gtg | gct | ctt | gat | ggc | agt | agt | cag | ccc | aca | gag | aac | 96 |
| Leu | Val | His | Pro | Val | Ala | Leu | Asp | Gly | Ser | Ser | Gln | Pro | Thr | Glu | Asn | |
| | | | 20 | | | | | 25 | | | | | 30 | | | |
| gct | gaa | aaa | gac | gga | ctg | tgc | aat | gct | tgc | acg | tgg | aga | cag | aat | act | 144 |
| Ala | Glu | Lys | Asp | Gly | Leu | Cys | Asn | Ala | Cys | Thr | Trp | Arg | Gln | Asn | Thr | |
| | | 35 | | | | | 40 | | | | | 45 | | | | |
| aaa | tcc | tcc | aga | ata | gaa | gcc | ata | aaa | att | caa | atc | ctc | agc | aaa | ctg | 192 |
| Lys | Ser | Ser | Arg | Ile | Glu | Ala | Ile | Lys | Ile | Gln | Ile | Leu | Ser | Lys | Leu | |
| | 50 | | | | | 55 | | | | | 60 | | | | | |
| cgc | ctg | gaa | caa | gca | cct | aac | att | agc | agg | gac | gtt | att | aaa | caa | ctt | 240 |
| Arg | Leu | Glu | Gln | Ala | Pro | Asn | Ile | Ser | Arg | Asp | Val | Ile | Lys | Gln | Leu | |
| 65 | | | | | 70 | | | | | 75 | | | | | 80 | |
| tta | ccc | aaa | gct | cct | ccg | ctg | cag | gaa | ctg | att | gat | cag | tat | gac | gtc | 288 |
| Leu | Pro | Lys | Ala | Pro | Pro | Leu | Gln | Glu | Leu | Ile | Asp | Gln | Tyr | Asp | Val | |
| | | | | 85 | | | | | 90 | | | | | 95 | | |
| cag | aga | gac | gac | agt | agc | gat | ggc | tct | ttg | gaa | gac | gat | gac | tat | cat | 336 |
| Gln | Arg | Asp | Asp | Ser | Ser | Asp | Gly | Ser | Leu | Glu | Asp | Asp | Asp | Tyr | His | |
| | | | 100 | | | | | 105 | | | | | 110 | | | |
| gcc | aca | acc | gaa | acg | att | atc | aca | atg | cct | acg | gag | tct | gat | ttt | ctt | 384 |
| Ala | Thr | Thr | Glu | Thr | Ile | Ile | Thr | Met | Pro | Thr | Glu | Ser | Asp | Phe | Leu | |
| | | 115 | | | | | 120 | | | | | 125 | | | | |
| gta | caa | atg | gag | gga | aaa | cca | aaa | tgt | tgc | ttc | ttt | aag | ttt | agc | tct | 432 |
| Val | Gln | Met | Glu | Gly | Lys | Pro | Lys | Cys | Cys | Phe | Phe | Lys | Phe | Ser | Ser | |
| | 130 | | | | | 135 | | | | | 140 | | | | | |
| aaa | ata | caa | tat | aac | aaa | gta | gta | aag | gca | caa | tta | tgg | ata | tac | ttg | 480 |
| Lys | Ile | Gln | Tyr | Asn | Lys | Val | Val | Lys | Ala | Gln | Leu | Trp | Ile | Tyr | Leu | |
| 145 | | | | | 150 | | | | | 155 | | | | | 160 | |
| agg | caa | gtc | caa | aaa | cct | aca | acg | gtg | ttt | gtg | cag | atc | ctg | aga | ctc | 528 |
| Arg | Gln | Val | Gln | Lys | Pro | Thr | Thr | Val | Phe | Val | Gln | Ile | Leu | Arg | Leu | |
| | | | | 165 | | | | | 170 | | | | | 175 | | |
| att | aaa | ccc | atg | aaa | gac | ggt | aca | aga | tat | act | gga | att | cga | tct | ttg | 576 |
| Ile | Lys | Pro | Met | Lys | Asp | Gly | Thr | Arg | Tyr | Thr | Gly | Ile | Arg | Ser | Leu | |
| | | | 180 | | | | | 185 | | | | | 190 | | | |
| aaa | ctt | gac | atg | aac | cca | ggc | act | ggt | atc | tgg | cag | agt | att | gat | gtg | 624 |
| Lys | Leu | Asp | Met | Asn | Pro | Gly | Thr | Gly | Ile | Trp | Gln | Ser | Ile | Asp | Val | |

```
                195                 200                 205
aag aca gtg ttg caa aat tgg ctc aaa cag cct gaa tcc aat tta ggc      672
Lys Thr Val Leu Gln Asn Trp Leu Lys Gln Pro Glu Ser Asn Leu Gly
    210                 215                 220 atc gaa ata aaa gct ttt gat gag aat gga cga gat ctt gct gta aca      720
Ile Glu Ile Lys Ala Phe Asp Glu Asn Gly Arg Asp Leu Ala Val Thr
225                 230                 235                 240 ttc cca gga cca ggt gaa gat gga ctg aac cca ttt tta gag gtc aga      768
Phe Pro Gly Pro Gly Glu Asp Gly Leu Asn Pro Phe Leu Glu Val Arg
                245                 250                 255 gtt aca gac aca cca aaa cgg tcc cgc aga gat ttt ggc ctt gac tgc      816
Val Thr Asp Thr Pro Lys Arg Ser Arg Arg Asp Phe Gly Leu Asp Cys
            260                 265                 270 gac gag cac tca acg gaa tct cga tgt tgt cgc tac ccg ctg aca gtg      864
Asp Glu His Ser Thr Glu Ser Arg Cys Cys Arg Tyr Pro Leu Thr Val
        275                 280                 285 gat ttt gaa gct ttt gga tgg gac tgg att ata gca cct aaa aga tac      912
Asp Phe Glu Ala Phe Gly Trp Asp Trp Ile Ile Ala Pro Lys Arg Tyr
    290                 295                 300 aaa gcc aat tac tgc tct gga gaa tgt gaa ttc gta ttt cta cag aaa      960
Lys Ala Asn Tyr Cys Ser Gly Glu Cys Glu Phe Val Phe Leu Gln Lys
305                 310                 315                 320 tac ccg cac act cac ctg gta cac caa gca aat cca aga ggc tca gca     1008
Tyr Pro His Thr His Leu Val His Gln Ala Asn Pro Arg Gly Ser Ala
                325                 330                 335 ggc cct tgc tgc aca ccc acc aag atg tcc cct ata aac atg ctg tat     1056
Gly Pro Cys Cys Thr Pro Thr Lys Met Ser Pro Ile Asn Met Leu Tyr
            340                 345                 350 ttc aat gga aaa gaa caa ata ata tat gga aag ata cca gcc atg gtt     1104
Phe Asn Gly Lys Glu Gln Ile Ile Tyr Gly Lys Ile Pro Ala Met Val
        355                 360                 365 gta gat cgt tgc ggg tgc tca tga                                      1128
Val Asp Arg Cys Gly Cys Ser
    370                 375

<210> SEQ ID NO 18
<211> LENGTH: 375
<212> TYPE: PRT
<213> ORGANISM: Meleagris gallopavo

<400> SEQUENCE: 18

Met Gln Lys Leu Ala Val Tyr Val Tyr Ile Tyr Leu Phe Met Gln Ile
1               5                   10                  15

Leu Val His Pro Val Ala Leu Asp Gly Ser Ser Gln Pro Thr Glu Asn
            20                  25                  30

Ala Glu Lys Asp Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Gln Ala Pro Asn Ile Ser Arg Asp Val Ile Lys Gln Leu
65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Val Gln Met Glu Gly Lys Pro Lys Cys Cys Phe Phe Lys Phe Ser Ser
```

-continued

```
            130                 135                 140
Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Phe Asp Glu Asn Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

<210> SEQ ID NO 19
<211> LENGTH: 1125
<212> TYPE: DNA
<213> ORGANISM: Danio rerio
<220> FEATURE:
<221> NAME/KEY: CDS
<222> LOCATION: (1)..(1122)

<400> SEQUENCE: 19 atg cat ttt aca cag gtt tta att tct cta agt gta tta att gca tgt      48
Met His Phe Thr Gln Val Leu Ile Ser Leu Ser Val Leu Ile Ala Cys
1               5                  10                  15 ggt cca gtg ggt tat gga gat ata acg gcg cac cag cag cct tcc aca      96
Gly Pro Val Gly Tyr Gly Asp Ile Thr Ala His Gln Gln Pro Ser Thr
            20                  25                  30 gcc acg gag gaa agc gag ctg tgt tcc aca tgt gag ttc aga caa cac     144
Ala Thr Glu Glu Ser Glu Leu Cys Ser Thr Cys Glu Phe Arg Gln His
        35                  40                  45 agc aag ctg atg aga ctg cat gcc atc aag tcc caa att ctt agc aaa     192
Ser Lys Leu Met Arg Leu His Ala Ile Lys Ser Gln Ile Leu Ser Lys
    50                  55                  60 ctc cga ctc aag cag gct cca aac atc agc cgg gac gtg gtc aag cag     240
Leu Arg Leu Lys Gln Ala Pro Asn Ile Ser Arg Asp Val Val Lys Gln
65                  70                  75                  80 ctg tta ccc aaa gca ccg cct ttg caa caa ctt ctg gat cag tac gat     288
```

|  |  |
|---|---|
| Leu Leu Pro Lys Ala Pro Pro Leu Gln Gln Leu Leu Asp Gln Tyr Asp<br>                85                    90                  95 | |
| gtt tta gga gat gac agt aag gat gga gct gtg gaa gag gac gat gaa<br>Val Leu Gly Asp Asp Ser Lys Asp Gly Ala Val Glu Glu Asp Asp Glu<br>                100                  105              110 | 336 |
| cat gcc acc aca gag acc atc atg acc atg gcc aca gaa cct gac ccc<br>His Ala Thr Thr Glu Thr Ile Met Thr Met Ala Thr Glu Pro Asp Pro<br>        115                  120                  125 | 384 |
| att gtt caa gta gat cgg aaa ccg aag tgt tgc ttt ttc tcc ttc agt<br>Ile Val Gln Val Asp Arg Lys Pro Lys Cys Cys Phe Phe Ser Phe Ser<br>    130                  135                  140 | 432 |
| ccg aag atc caa gcg aac cgg atc gta aga gcg cag ctc tgg gtt cat<br>Pro Lys Ile Gln Ala Asn Arg Ile Val Arg Ala Gln Leu Trp Val His<br>145                  150                  155                  160 | 480 |
| ctg aga ccg gcg gag gag gcg acc acc gtc ttc tta cag ata tct cgg<br>Leu Arg Pro Ala Glu Glu Ala Thr Thr Val Phe Leu Gln Ile Ser Arg<br>                165                  170              175 | 528 |
| ctg atg ccc gtt aag gac gga gga aga cac cga ata cga tcc ctg aaa<br>Leu Met Pro Val Lys Asp Gly Gly Arg His Arg Ile Arg Ser Leu Lys<br>        180                  185                  190 | 576 |
| atc gac gtg aac gca gga gtc acg tct tgg cag agt ata gac gta aag<br>Ile Asp Val Asn Ala Gly Val Thr Ser Trp Gln Ser Ile Asp Val Lys<br>    195                  200                  205 | 624 |
| cag gtg ctc acg gtg tgg tta aaa caa ccg gag acc aac cga ggc atc<br>Gln Val Leu Thr Val Trp Leu Lys Gln Pro Glu Thr Asn Arg Gly Ile<br>210                  215                  220 | 672 |
| gag att aac gca tat gac gcg aag gga aac gac ttg gcc gtc act tca<br>Glu Ile Asn Ala Tyr Asp Ala Lys Gly Asn Asp Leu Ala Val Thr Ser<br>225                  230                  235              240 | 720 |
| acc gag act ggg gag gat gga ctg ctc ccc ttt atg gag gtg aaa ata<br>Thr Glu Thr Gly Glu Asp Gly Leu Leu Pro Phe Met Glu Val Lys Ile<br>                245                  250              255 | 768 |
| tca gag ggc cca aaa cga atc cgg agg gac tcc gga ctg gac tgc gat<br>Ser Glu Gly Pro Lys Arg Ile Arg Arg Asp Ser Gly Leu Asp Cys Asp<br>        260                  265                  270 | 816 |
| gag aat tcc tca gag tct cgc tgc tgc agg tac cct ctc act gtg gac<br>Glu Asn Ser Ser Glu Ser Arg Cys Cys Arg Tyr Pro Leu Thr Val Asp<br>    275                  280                  285 | 864 |
| ttc gag gac ttt ggc tgg gac tgg att att gct cca aaa cgc tat aag<br>Phe Glu Asp Phe Gly Trp Asp Trp Ile Ile Ala Pro Lys Arg Tyr Lys<br>290                  295                  300 | 912 |
| gcg aat tac tgt tca gga gaa tgc gac tac atg tac ctg cag aag tat<br>Ala Asn Tyr Cys Ser Gly Glu Cys Asp Tyr Met Tyr Leu Gln Lys Tyr<br>305                  310                  315              320 | 960 |
| ccc cac acc cat ctg gtg aac aag gcc agt ccg aga gga acg gct ggg<br>Pro His Thr His Leu Val Asn Lys Ala Ser Pro Arg Gly Thr Ala Gly<br>                325                  330              335 | 1008 |
| ccc tgc tgc act ccc acc aag atg tct ccc atc aac atg ctt tac ttt<br>Pro Cys Cys Thr Pro Thr Lys Met Ser Pro Ile Asn Met Leu Tyr Phe<br>        340                  345                  350 | 1056 |
| aac ggc aaa gag cag atc atc tac ggc aag atc cct tcg atg gta gta<br>Asn Gly Lys Glu Gln Ile Ile Tyr Gly Lys Ile Pro Ser Met Val Val<br>    355                  360                  365 | 1104 |
| gac cgc tgt ggc tgc tca tga<br>Asp Arg Cys Gly Cys Ser<br>        370 | 1125 |

<210> SEQ ID NO 20
<211> LENGTH: 374
<212> TYPE: PRT

<213> ORGANISM: Danio rerio

<400> SEQUENCE: 20

```
Met His Phe Thr Gln Val Leu Ile Ser Leu Ser Val Leu Ile Ala Cys
1               5                   10                  15

Gly Pro Val Gly Tyr Gly Asp Ile Thr Ala His Gln Gln Pro Ser Thr
            20                  25                  30

Ala Thr Glu Glu Ser Glu Leu Cys Ser Thr Cys Glu Phe Arg Gln His
        35                  40                  45

Ser Lys Leu Met Arg Leu His Ala Ile Lys Ser Gln Ile Leu Ser Lys
    50                  55                  60

Leu Arg Leu Lys Gln Ala Pro Asn Ile Ser Arg Asp Val Val Lys Gln
65                  70                  75                  80

Leu Leu Pro Lys Ala Pro Pro Leu Gln Gln Leu Leu Asp Gln Tyr Asp
                85                  90                  95

Val Leu Gly Asp Asp Ser Lys Asp Gly Ala Val Glu Glu Asp Asp Glu
            100                 105                 110

His Ala Thr Thr Glu Thr Ile Met Thr Met Ala Thr Glu Pro Asp Pro
        115                 120                 125

Ile Val Gln Val Asp Arg Lys Pro Lys Cys Cys Phe Phe Ser Phe Ser
130                 135                 140

Pro Lys Ile Gln Ala Asn Arg Ile Val Arg Ala Gln Leu Trp Val His
145                 150                 155                 160

Leu Arg Pro Ala Glu Glu Ala Thr Thr Val Phe Leu Gln Ile Ser Arg
                165                 170                 175

Leu Met Pro Val Lys Asp Gly Gly Arg His Arg Ile Arg Ser Leu Lys
            180                 185                 190

Ile Asp Val Asn Ala Gly Val Thr Ser Trp Gln Ser Ile Asp Val Lys
        195                 200                 205

Gln Val Leu Thr Val Trp Leu Lys Gln Pro Glu Thr Asn Arg Gly Ile
    210                 215                 220

Glu Ile Asn Ala Tyr Asp Ala Lys Gly Asn Asp Leu Ala Val Thr Ser
225                 230                 235                 240

Thr Glu Thr Gly Glu Asp Gly Leu Leu Pro Phe Met Glu Val Lys Ile
                245                 250                 255

Ser Glu Gly Pro Lys Arg Ile Arg Arg Asp Ser Gly Leu Asp Cys Asp
            260                 265                 270

Glu Asn Ser Ser Glu Ser Arg Cys Cys Arg Tyr Pro Leu Thr Val Asp
        275                 280                 285

Phe Glu Asp Phe Gly Trp Asp Trp Ile Ile Ala Pro Lys Arg Tyr Lys
    290                 295                 300

Ala Asn Tyr Cys Ser Gly Glu Cys Asp Tyr Met Tyr Leu Gln Lys Tyr
305                 310                 315                 320

Pro His Thr His Leu Val Asn Lys Ala Ser Pro Arg Gly Thr Ala Gly
                325                 330                 335

Pro Cys Cys Thr Pro Thr Lys Met Ser Pro Ile Asn Met Leu Tyr Phe
            340                 345                 350

Asn Gly Lys Glu Gln Ile Ile Tyr Gly Lys Ile Pro Ser Met Val Val
        355                 360                 365

Asp Arg Cys Gly Cys Ser
    370
```

<210> SEQ ID NO 21
<211> LENGTH: 4

```
<212> TYPE: PRT
<213> ORGANISM: artificial
<220> FEATURE:
<223> OTHER INFORMATION: proteolytic cleavage site
<221> NAME/KEY: VARIANT
<222> LOCATION: (1)..(4)
<223> OTHER INFORMATION: Xaa is any amino acid

<400> SEQUENCE: 21

Arg Xaa Xaa Arg
1

<210> SEQ ID NO 22
<211> LENGTH: 4
<212> TYPE: PRT
<213> ORGANISM: artificial
<220> FEATURE:
<223> OTHER INFORMATION: proteolytic processing site

<400> SEQUENCE: 22

Arg Ser Arg Arg
1

<210> SEQ ID NO 23
<211> LENGTH: 4
<212> TYPE: PRT
<213> ORGANISM: artificial
<220> FEATURE:
<223> OTHER INFORMATION: proteolytic processing site

<400> SEQUENCE: 23

Arg Ile Arg Arg
1

<210> SEQ ID NO 24
<211> LENGTH: 1393
<212> TYPE: DNA
<213> ORGANISM: Homo sapiens
<220> FEATURE:
<221> NAME/KEY: CDS
<222> LOCATION: (54)..(1274)

<400> SEQUENCE: 24
ccgcgggact ccggcgtccc cgccccccag tcctccctcc cctcccctcc agc atg      56
                                                         Met
                                                         1 gtg ctc gcg gcc ccg ctg ctg ctg ggc ttc ctg ctc ctc gcc ctg gag   104
Val Leu Ala Ala Pro Leu Leu Leu Gly Phe Leu Leu Leu Ala Leu Glu
        5                   10                  15 ctg cgg ccc cgg ggg gag gcg gcc gag ggc ccc gcg gcg gcg gcg gcg   152
Leu Arg Pro Arg Gly Glu Ala Ala Glu Gly Pro Ala Ala Ala Ala Ala
            20                  25                  30 gcg gcg gcg gcg gcg gca gcg gcg ggg gtc ggg ggg gag cgc tcc agc   200
Ala Ala Ala Ala Ala Ala Ala Ala Gly Val Gly Gly Glu Arg Ser Ser
    35                  40                  45 cgg cca gcc ccg tcc gtg gcg ccc gag ccg gac ggc tgc ccc gtg tgc   248
Arg Pro Ala Pro Ser Val Ala Pro Glu Pro Asp Gly Cys Pro Val Cys
50                  55                  60                  65 gtt tgg cgg cag cac agc cgc gag ctg cgc cta gag agc atc aag tcg   296
Val Trp Arg Gln His Ser Arg Glu Leu Arg Leu Glu Ser Ile Lys Ser
                70                  75                  80 cag atc ttg agc aaa ctg cgg ctc aag gag gcg ccc aac atc agc cgc   344
Gln Ile Leu Ser Lys Leu Arg Leu Lys Glu Ala Pro Asn Ile Ser Arg
            85                  90                  95 gag gtg gtg aag cag ctg ctg ccc aag gcg ccg ccg ctg cag cag atc   392
```

```
                Glu Val Val Lys Gln Leu Leu Pro Lys Ala Pro Pro Leu Gln Gln Ile
                            100                 105                 110 ctg gac cta cac gac ttc cag ggc gac gcg ctg cag ccc gag gac ttc           440
Leu Asp Leu His Asp Phe Gln Gly Asp Ala Leu Gln Pro Glu Asp Phe
        115                 120                 125 ctg gag gag gac gag tac cac gcc acc acc gag acc gtc att agc atg           488
Leu Glu Glu Asp Glu Tyr His Ala Thr Thr Glu Thr Val Ile Ser Met
130                 135                 140                 145 gcc cag gag acg gac cca gca gta cag aca gat ggc agc cct ctc tgc           536
Ala Gln Glu Thr Asp Pro Ala Val Gln Thr Asp Gly Ser Pro Leu Cys
                150                 155                 160 tgc cat ttt cac ttc agc ccc aag gtg atg ttc aca aag gta ctg aag           584
Cys His Phe His Phe Ser Pro Lys Val Met Phe Thr Lys Val Leu Lys
            165                 170                 175 gcc cag ctg tgg gtg tac cta cgg cct gta ccc cgc cca gcc aca gtc           632
Ala Gln Leu Trp Val Tyr Leu Arg Pro Val Pro Arg Pro Ala Thr Val
        180                 185                 190 tac ctg cag atc ttg cga cta aaa ccc cta act ggg gaa ggg acc gca           680
Tyr Leu Gln Ile Leu Arg Leu Lys Pro Leu Thr Gly Glu Gly Thr Ala
195                 200                 205 ggg gga ggg ggc gga ggc cgg cgt cac atc cgt atc cgc tca ctg aag           728
Gly Gly Gly Gly Gly Gly Arg Arg His Ile Arg Ile Arg Ser Leu Lys
210                 215                 220                 225 att gag ctg cac tca cgc tca ggc cat tgg cag agc atc gac ttc aag           776
Ile Glu Leu His Ser Arg Ser Gly His Trp Gln Ser Ile Asp Phe Lys
                230                 235                 240 caa gtg cta cac agc tgg ttc cgc cag cca cag agc aac tgg ggc atc           824
Gln Val Leu His Ser Trp Phe Arg Gln Pro Gln Ser Asn Trp Gly Ile
            245                 250                 255 gag atc aac gcc ttt gat ccc agt ggc aca gac ctg gct gtc acc tcc           872
Glu Ile Asn Ala Phe Asp Pro Ser Gly Thr Asp Leu Ala Val Thr Ser
        260                 265                 270 ctg ggg ccg gga gcc gag ggg ctg cat cca ttc atg gag ctt cga gtc           920
Leu Gly Pro Gly Ala Glu Gly Leu His Pro Phe Met Glu Leu Arg Val
275                 280                 285 cta gag aac aca aaa cgt tcc cgg cgg aac ctg ggt ctg gac tgc gac           968
Leu Glu Asn Thr Lys Arg Ser Arg Arg Asn Leu Gly Leu Asp Cys Asp
290                 295                 300                 305 gag cac tca agc gag tcc cgc tgc tgc cga tat ccc ctc aca gtg gac          1016
Glu His Ser Ser Glu Ser Arg Cys Cys Arg Tyr Pro Leu Thr Val Asp
                310                 315                 320 ttt gag gct ttc ggc tgg gac tgg atc atc gca cct aag cgc tac aag          1064
Phe Glu Ala Phe Gly Trp Asp Trp Ile Ile Ala Pro Lys Arg Tyr Lys
            325                 330                 335 gcc aac tac tgc tcc ggc cag tgc gag tac atg ttc atg caa aaa tat          1112
Ala Asn Tyr Cys Ser Gly Gln Cys Glu Tyr Met Phe Met Gln Lys Tyr
        340                 345                 350 ccg cat acc cat ttg gtg cag cag gcc aat cca aga ggc tct gct ggg          1160
Pro His Thr His Leu Val Gln Gln Ala Asn Pro Arg Gly Ser Ala Gly
355                 360                 365 ccc tgt tgt acc ccc acc aag atg tcc cca atc aac atg ctc tac ttc          1208
Pro Cys Cys Thr Pro Thr Lys Met Ser Pro Ile Asn Met Leu Tyr Phe
370                 375                 380                 385 aat gac aag cag cag att atc tac ggc aag atc cct ggc atg gtg gtg          1256
Asn Asp Lys Gln Gln Ile Ile Tyr Gly Lys Ile Pro Gly Met Val Val
                390                 395                 400 gat cgc tgt ggc tgc tct taagtgggtc actacaagct gctggagcaa                 1304
Asp Arg Cys Gly Cys Ser
            405
```

```
agacttggtg ggtgggtaac ttaacctctt cacagaggat aaaaaatgct tgtgagtatg    1364
acagaaggga ataaacaggc ttaaagggt                                      1393
```

<210> SEQ ID NO 25
<211> LENGTH: 407
<212> TYPE: PRT
<213> ORGANISM: Homo sapiens

<400> SEQUENCE: 25

```
Met Val Leu Ala Ala Pro Leu Leu Gly Phe Leu Leu Ala Leu
1               5                   10                  15

Glu Leu Arg Pro Arg Gly Glu Ala Glu Gly Pro Ala Ala Ala
            20                  25                  30

Ala Ala Ala Ala Ala Ala Ala Ala Gly Val Gly Gly Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
```

```
                355                 360                 365
Gly Pro Cys Cys Thr Pro Thr Lys Met Ser Pro Ile Asn Met Leu Tyr
        370                 375                 380

Phe Asn Asp Lys Gln Gln Ile Ile Tyr Gly Lys Ile Pro Gly Met Val
385                 390                 395                 400

Val Asp Arg Cys Gly Cys Ser
            405

<210> SEQ ID NO 26
<211> LENGTH: 476
<212> TYPE: DNA
<213> ORGANISM: Salmon
<220> FEATURE:
<221> NAME/KEY: CDS
<222> LOCATION: (3)..(473)
<223> OTHER INFORMATION: Salmon-1

<400> SEQUENCE: 26 gg cag ccg gag acg aat tgg ggg atc gag att aat gcg ttc gac tcg        47
   Gln Pro Glu Thr Asn Trp Gly Ile Glu Ile Asn Ala Phe Asp Ser
   1               5                  10                  15 aag gga aat gat ctg gcc gtt acc tca gca gaa gcg gga gaa gga ctg       95
Lys Gly Asn Asp Leu Ala Val Thr Ser Ala Glu Ala Gly Glu Gly Leu
            20                  25                  30 caa ccc ttc atg gag gtg acg att tca gag ggc ccg aag cgc tcc agg      143
Gln Pro Phe Met Glu Val Thr Ile Ser Glu Gly Pro Lys Arg Ser Arg
        35                  40                  45 aga gac tcg ggc ctg gac tgt gac gag aac tcc ccc gag tcc cgc tgt      191
Arg Asp Ser Gly Leu Asp Cys Asp Glu Asn Ser Pro Glu Ser Arg Cys
    50                  55                  60 tgc cgc tac ccc ctc acg gta gac ttt gaa gac ttt ggc tgg gac tgg      239
Cys Arg Tyr Pro Leu Thr Val Asp Phe Glu Asp Phe Gly Trp Asp Trp
65                  70                  75 att att gcc ccc aag cgc tac aag gcc aac tac tgc tct ggt gag tgt      287
Ile Ile Ala Pro Lys Arg Tyr Lys Ala Asn Tyr Cys Ser Gly Glu Cys
80                  85                  90                  95 gag tac atg cac ctg cag aag tac ccc cac acc cac ctg gtg aac aag      335
Glu Tyr Met His Leu Gln Lys Tyr Pro His Thr His Leu Val Asn Lys
                100                 105                 110 gct aac cct cgc ggc acc gca ggg ccc tgc tgc acc ccc acc aag atg      383
Ala Asn Pro Arg Gly Thr Ala Gly Pro Cys Cys Thr Pro Thr Lys Met
            115                 120                 125 tcc ccc atc aac atg ctc tac ttc aac cgc aaa gag cag atc atc tac      431
Ser Pro Ile Asn Met Leu Tyr Phe Asn Arg Lys Glu Gln Ile Ile Tyr
        130                 135                 140 ggc aag atc ccc tcc atg gtg gtg gac cgt tgc gga tgc tcg tga          476
Gly Lys Ile Pro Ser Met Val Val Asp Arg Cys Gly Cys Ser
    145                 150                 155

<210> SEQ ID NO 27
<211> LENGTH: 157
<212> TYPE: PRT
<213> ORGANISM: Salmon

<400> SEQUENCE: 27

Gln Pro Glu Thr Asn Trp Gly Ile Glu Ile Asn Ala Phe Asp Ser Lys
1               5                   10                  15

Gly Asn Asp Leu Ala Val Thr Ser Ala Glu Ala Gly Glu Gly Leu Gln
            20                  25                  30

Pro Phe Met Glu Val Thr Ile Ser Glu Gly Pro Lys Arg Ser Arg Arg
        35                  40                  45
```

```
Asp Ser Gly Leu Asp Cys Asp Glu Asn Ser Pro Glu Ser Arg Cys Cys
    50                  55                  60

Arg Tyr Pro Leu Thr Val Asp Phe Glu Asp Phe Gly Trp Asp Trp Ile
65                  70                  75                  80

Ile Ala Pro Lys Arg Tyr Lys Ala Asn Tyr Cys Ser Gly Glu Cys Glu
                85                  90                  95

Tyr Met His Leu Gln Lys Tyr Pro His Thr His Leu Val Asn Lys Ala
            100                 105                 110

Asn Pro Arg Gly Thr Ala Gly Pro Cys Cys Thr Pro Thr Lys Met Ser
        115                 120                 125

Pro Ile Asn Met Leu Tyr Phe Asn Arg Lys Glu Gln Ile Ile Tyr Gly
    130                 135                 140

Lys Ile Pro Ser Met Val Val Asp Arg Cys Gly Cys Ser
145                 150                 155

<210> SEQ ID NO 28
<211> LENGTH: 412
<212> TYPE: DNA
<213> ORGANISM: Salmon
<220> FEATURE:
<221> NAME/KEY: CDS
<222> LOCATION: (2)..(409)
<223> OTHER INFORMATION: Salmon-2

<400> SEQUENCE: 28 g gtt acc tca act gaa gcc gga gaa gga ctg caa ccc ttc atg gag gtg      49
  Val Thr Ser Thr Glu Ala Gly Glu Gly Leu Gln Pro Phe Met Glu Val
  1               5                   10                  15 aag att tcg gag ggc ccg aag cgc tcc agg aga gat tcg ggc ctg gac      97
Lys Ile Ser Glu Gly Pro Lys Arg Ser Arg Arg Asp Ser Gly Leu Asp
                20                  25                  30 tgt gat gag aac tcc ccc gag tcc cgc tgc tgc cgg tac ccc ctc acg     145
Cys Asp Glu Asn Ser Pro Glu Ser Arg Cys Cys Arg Tyr Pro Leu Thr
            35                  40                  45 gtg gac ttt gaa gac ttt ggc tgg gac tgg att att gcc ccc aag cgc     193
Val Asp Phe Glu Asp Phe Gly Trp Asp Trp Ile Ile Ala Pro Lys Arg
50                  55                  60 tac aag gcc aac tac tgc tct ggt gag tgc gag tac atg cac ctg cag     241
Tyr Lys Ala Asn Tyr Cys Ser Gly Glu Cys Glu Tyr Met His Leu Gln
65                  70                  75                  80 aag tac ccc cac acc cac ctg gtg aac aag gct aac cct cgc ggc acc     289
Lys Tyr Pro His Thr His Leu Val Asn Lys Ala Asn Pro Arg Gly Thr
                85                  90                  95 gcg ggg ccc tgc tgc acc ccc acc aag atg tcc ccc atc aac atg ctc     337
Ala Gly Pro Cys Cys Thr Pro Thr Lys Met Ser Pro Ile Asn Met Leu
            100                 105                 110 tac ttc aac cgc aaa gag cag atc atc tac ggc aag atc ccc tcc atg     385
Tyr Phe Asn Arg Lys Glu Gln Ile Ile Tyr Gly Lys Ile Pro Ser Met
        115                 120                 125 gtg gtg gac cgc tgc ggc tgc tcg tga                                  412
Val Val Asp Arg Cys Gly Cys Ser
    130                 135

<210> SEQ ID NO 29
<211> LENGTH: 136
<212> TYPE: PRT
<213> ORGANISM: Salmon

<400> SEQUENCE: 29

Val Thr Ser Thr Glu Ala Gly Glu Gly Leu Gln Pro Phe Met Glu Val
```

```
 1               5                    10                   15
Lys Ile Ser Glu Gly Pro Lys Arg Ser Arg Arg Asp Ser Gly Leu Asp
                20                  25                  30

Cys Asp Glu Asn Ser Pro Glu Ser Arg Cys Cys Arg Tyr Pro Leu Thr
                35                  40                  45

Val Asp Phe Glu Asp Phe Gly Trp Asp Trp Ile Ile Ala Pro Lys Arg
            50              55                  60

Tyr Lys Ala Asn Tyr Cys Ser Gly Glu Cys Glu Tyr Met His Leu Gln
65                      70                  75                  80

Lys Tyr Pro His Thr His Leu Val Asn Lys Ala Asn Pro Arg Gly Thr
                    85                  90                  95

Ala Gly Pro Cys Cys Thr Pro Thr Lys Met Ser Pro Ile Asn Met Leu
                100                 105                 110

Tyr Phe Asn Arg Lys Glu Gln Ile Ile Tyr Gly Lys Ile Pro Ser Met
                115                 120                 125

Val Val Asp Arg Cys Gly Cys Ser
130                 135
```

US 7,393,682 B1

POLYNUCLEOTIDES ENCODING PROMYOSTATIN POLYPEPTIDES

This application is a continuation of U.S. Ser. No. 09/628,112, filed Jul. 27, 2000, which is a continuation-in-part (CIP) of U.S. Ser. No. 09/124,180, filed Jul. 28, 1998 (now abandoned); which is a CIP of U.S. Ser. No. 09/019,070, filed Feb. 5, 1998 (now abandoned), which is a CIP of U.S. Ser. No. 08/862,445, filed May 23, 1997 (now abandoned), which is a CIP of U.S. Ser. No. 08/847,910, filed Apr. 28, 1997 (now abandoned), which is a CIP of U.S. Ser. No. 08/795,071, filed Feb. 5, 1997 (now U.S. Pat. No. 5,994,618, which issued Nov. 11, 1999); which is a CIP of U.S. Ser. No. 08/525,596, filed Oct. 26, 1995 (now U.S. Pat. No. 5,827,733, which issued Oct. 27, 1998), which is a 371 of PCT/US94/03019, filed Mar. 18, 1994, and wherein said U.S. Ser. No. 09/124,180 is a CIP of U.S. Ser. No. 08/033,923, filed Mar. 19, 1993 (now abandoned) the entire contents of each of which is incorporated herein by reference.

This invention was made in part with government support under Grant No. RO1HD35887 awarded by the National Institutes of Health. The government has certain rights in this invention.

BACKGROUND OF THE INVENTION

1. Field of the Invention

The invention relates generally to peptide portions of promyostatin (growth differentiation factor-8; GDF-8) polypeptides, and more specifically to compositions that affect myostatin signal transduction in a cell, and to methods of using such compositions to modulate myostatin signal transduction in a cell.

2. Background Information

The amount of time, effort and money spent in the United States each year by individuals intent on losing weight is staggering. For many of these individuals, the goal is not merely to look better, but more importantly to avoid the inevitable medical problems associated with being overweight.

Greater than half of the adult population in the United States is considered to be overweight. Furthermore, twenty to thirty percent of adult men and thirty to forty percent of adult women in the United States are considered obese, with the highest rates occurring among the poor and minorities. Obesity, which is defined a being at least about twenty percent above the mean level of adiposity, has dramatically increased in prevalence over the past few decades and is becoming a major problem among the pediatric population. Twenty percent of all children are now considered overweight, a number that represents a doubling over the past five years.

Obesity and the medical problems directly attributable to it are a major cause of morbidity and mortality throughout the world. Obesity is a major risk factor for the development of various pathologic conditions, including atherosclerosis, hypertension, heart attack, type II diabetes, gallbladder disease, and certain cancers, and contributes to premature death. Heart disease is the leading cause of mortality in the United States, and type II diabetes afflicts over 16 million people in the United States and is one of the leading causes of death by disease.

More than eighty percent of type II diabetes occurs in obese persons. Although type II diabetes affects all races, it is particularly prevalent among Native Americans, African Americans and Hispanics. Significantly, type II diabetes, which used to occur almost exclusively in adults over age forty, now occurs in children, with reported cases having almost tripled over the last five years. Type II diabetes, also called non-insulin dependent diabetes, is characterized by reduced secretion of insulin in response to glucose and by resistance of the body to the action of insulin, even though insulin levels in the circulation generally are normal or elevated. Type II diabetes affects the function of a variety of different tissues and organs and can lead to vascular disease, renal failure, retinopathy and neuropathy.

In contrast to the medical problems associated with obesity, the severe weight loss that commonly occurs in patients with certain chronic diseases also presents a challenge to medical intervention. The molecular basis for this weight loss, referred to as cachexia, is not well understood. It is clear, however, that cachexia complicates management of such diseases and is associated with a poor prognosis for the patients. The effects of cachexia are evident in the wasting syndrome that occurs in cancer and AIDS patients.

Although great efforts have been made in attempting to elucidate the biological processes involved in regulating body weight, the results have provided more fanfare than actual value. For example, the discovery of leptin has been hailed as a breakthrough in understanding the molecular basis for fat accumulation in humans, and, with it, the promise of a cure for obesity. Studies in animals indicated that leptin is involved in transmitting internal signals regulating appetite, and suggested leptin could be useful for treating humans suffering from obesity. Progress in using leptin for treating obesity has been slow, however, and, thus far, leptin has not met initial expectations.

Treatment of the morbidly obese currently is limited to surgery to remove portions of the intestine, thereby reducing the amount of food (and calories) absorbed. For the moderately obese, the only "treatment" is eating a healthy diet and exercising regularly, a method that has proved modestly successful at best. Thus, a need exists to identify the biological factors involved in regulating body weight, including muscle development and fat accumulation, such that methods for treating disorders such as obesity and cachexia can be developed. The present invention satisfies this need and provides additional advantages.

SUMMARY OF THE INVENTION

The present invention relates to a substantially purified peptide portion of a promyostatin polypeptide. A promyostatin polypeptide is exemplified herein by a mammalian promyostatin having an amino acid sequence such as that of human promyostatin (SEQ ID NO: 2); murine promyostatin (SEQ ID NO: 4); rat promyostatin (SEQ ID NO: 6); baboon promyostatin (SEQ ID NO: 10); bovine promyostatin (SEQ ID NO: 12); porcine promyostatin (SEQ ID NO: 14); and ovine promyostatin (SEQ ID NO: 16); by an avian promyostatin having an amino acid sequence such as that of chicken promyostatin (SEQ ID NO: 8), and turkey promyostatin (SEQ ID NO: 18); and by a piscine promyostatin such as a zebrafish promyostatin polypeptide having an amino acid sequence as set forth in SEQ ID NO: 20. In addition, a promyostatin polypeptide is exemplified by a polypeptide comprising the portion of salmon allele 1 (SEQ ID NO: 27) or the portion of salmon allele 2 (SEQ ID NO: 29) disclosed herein.

The present invention also relates to a proteolytic fragment of a growth differentiation factor (GDF) polypeptide (pro-GDF) or a functional peptide portion thereof. Such proteolytic fragments are exemplified herein by proteolytic fragments of a promyostatin polypeptide and of a pro-GDF-11 polypeptide, and by functional peptide portions of such proteolytic fragments. A proteolytic fragment of a pro-GDF polypeptide or functional peptide portion thereof is characterized, in part, by having or affecting an activity associated with GDF signal transduction. As such, a promyostatin polypeptide or functional peptide portion thereof is can have, for example, myostatin receptor binding activity, myostatin signal transduction stimulatory or inhibitory activity, myostatin binding activity, or promyostatin binding activity. In one embodiment, the proteolytic fragment is a fragment produced by cleavage of a promyostatin polypeptide at a proteolytic cleavage recognition site having the amino acid sequence Arg-Xaa-Xaa-Arg (SEQ ID NO: 21). Such proteolytic recognition sites are exemplified by the Arg-Ser-Arg-Arg (SEQ ID NO: 22) sequence shown as amino acid residues 263 to 266 in SEQ ID NO: 1 (promyostatin) or amino acid residues 295 to 298 of SEQ ID NO: 25 (human pro-GDF-11), and by the Arg-Ile-Arg-Arg (SEQ ID NO: 23) sequence shown as amino acid residues 263 to 266 in SEQ ID NO: 20.

In another embodiment, the proteolytic fragment is a GDF prodomain, for example, a myostatin prodomain, which includes amino acid residues 1 to about 262 of a promyostatin polypeptide, or a functional peptide portion thereof, or a GDF-11 prodomain, which includes amino acid residues 1 to about 295 of a pro-GDF-11 polypeptide, or a functional peptide portion thereof. A myostatin prodomain is exemplified by amino acid residues 1 to about 263 as set forth in SEQ ID NO: 4 and SEQ ID NO: 6; as well as by amino acid residues 1 to about 262 as set forth in SEQ ID NO: 2, SEQ ID NO: 10, SEQ ID NO: 12, SEQ ID NO: 8, SEQ ID NO: 18, SEQ ID NO: 14, SEQ ID NO: 16, SEQ ID NO: 20. A functional peptide portion of a myostatin prodomain is exemplified by a peptide portion of a myostatin prodomain that can interact specifically with myostatin or with promyostatin. A GDF-11 prodomain is exemplified by amino acid residues 1 to about 295 of SEQ ID NO: 25, and a functional peptide portion of a GDF-11 prodomain is exemplified by a peptide portion of a GDF-11 prodomain that can specifically interact with mature GDF-11 or a pro-GDF-11 polypeptide. Preferably, the functional peptide portion of a GDF prodomain reduces or inhibits the ability of the corresponding GDF or a related GDF to stimulate signal transduction.

In still another embodiment, the proteolytic fragment of a pro-GDF polypeptide is a mature GDF peptide, or a functional peptide portion thereof. Thus, the proteolytic fragment can be a mature C-terminal myostatin peptide, which includes about amino acid residues 268 to 374 of a promyostatin polypeptide, or a mature C-terminal GDF-11 peptide, which includes about amino acid residues 299 to 407 of a pro-GDF-11 polypeptide. A mature myostatin peptide is exemplified by amino acid residues about 268 to 375 as set forth in SEQ ID NO: 4 and SEQ ID NO: 6; by amino acid residues about 267 to 374 as set forth in SEQ ID NO: 2, SEQ ID NO: 10, SEQ ID NO: 12, SEQ ID NO: 8, SEQ ID NO: 18, SEQ ID NO: 14, SEQ ID NO: 16, and SEQ ID NO: 20; and by the corresponding amino acid residues of SEQ ID NO: 27 and SEQ ID NO: 29. A functional peptide portion of a mature myostatin is exemplified by a peptide portion of myostatin that has myostatin signal transduction stimulatory or inhibitory activity. A mature GDF-11 peptide is exemplified by amino acid residues 299 to 407 of SEQ ID NO: 25, and a functional peptide portion of a mature GDF-11 peptide is exemplified by a peptide portion of mature GDF-11 that has GDF-11 signal transduction stimulatory or inhibitory activity. The activity of the functional peptide portion of a mature GDF peptide can be, for example, an ability to interact specifically with its receptor, an ability to reduce or inhibit the ability of a mature GDF peptide to interact specifically with its receptor, or any other activity that stimulates or inhibits GDF signal transduction activity.

The present invention further relates to a mutant pro-GDF polypeptide, for example, a mutant promyostatin polypeptide or a mutant pro-GDF-11 polypeptide, which contains an amino acid mutation that disrupts proteolytic cleavage at a proteolytic cleavage site having the amino acid sequence Arg-Xaa-Xaa-Arg (SEQ ID NO: 21). Thus, a mutant promyostatin or pro-GDF-11 polypeptide can have a mutation of an Arg residue of SEQ ID NO: 21, such that the mutant polypeptide cannot be cleaved into a prodomain and a mature GDF peptide. Preferably, the mutant GDF polypeptide has a dominant negative activity with respect to a corresponding or related wild type GDF polypeptide. For example, a mutant promyostatin polypeptide or a mutant pro-GDF-11 polypeptide can exhibit a dominant negative activity with respect to myostatin or GDF-11, respectively.

The present invention also relates to a polynucleotide encoding a peptide portion of a promyostatin or pro-GDF-11 polypeptide. For example, the polynucleotide can encode a myostatin or GDF-11 prodomain, or a functional peptide portion thereof. The invention further relates to antibodies that can specifically bind to a peptide portion of a promyostatin polypeptide, for example, to a myostatin prodomain or a functional peptide portion thereof, as well as to antibodies that can specifically bind to a peptide portion of a pro-GDF-11 polypeptide. A kit containing a peptide portion of a promyostatin or pro-GDF-11 polypeptide, or a mutant promyostatin or pro-GDF-11 polypeptide, or a polynucleotide encoding a peptide portion of a promyostatin or a pro-GDF-11 polypeptide, or an antibody that specifically binds such a peptide portion, or a combination thereof, also is provided.

In addition, the present invention relates to a method of identifying a functional peptide portion of a myostatin prodomain or a GDF-11 prodomain that interacts specifically with a myostatin peptide, a GDF-11 peptide, or both. A method of the invention can be performed, for example, by testing a peptide portion of a myostatin prodomain or a GDF-11 prodomain for the ability to interact specifically with myostatin; and detecting a specific interaction of the peptide portion with the myostatin. In one embodiment, a method of the invention is performed using a computer system, wherein the ability of a virtual peptide portion of a myostatin prodomain or a GDF-11 prodomain to specifically interact with a virtual myostatin peptide is tested. In another embodiment, the method is performed by contacting the peptide portion of the prodomain and the myostatin peptide under conditions suitable for a prodomain to specifically interact with a myostatin peptide.

BRIEF DESCRIPTION OF THE FIGURES

FIG. 1 shows the amino acid sequences of murine promyostatin (SEQ ID NO: 4); rat promyostatin (SEQ ID NO: 6); human promyostatin (SEQ ID NO: 2); baboon promyostatin (SEQ ID NO: 10); bovine promyostatin (SEQ ID NO: 12); porcine promyostatin (SEQ ID NO: 14); ovine promyostatin (SEQ ID NO: 16); chicken promyostatin (SEQ ID NO: 8), turkey promyostatin (SEQ ID NO: 18); and zebrafish promyostatin (SEQ ID NO: 20). Amino acids are numbered relative to the human promyostatin (SEQ ID NO: 2). Dashed lines indicate gaps introduced to maximize homology. Identical residues among sequences are shaded.

FIG. 2 shows the amino acid sequences of murine promyostatin (SEQ ID NO: 4) and zebrafish promyostatin (SEQ ID NO: 20), and portions of the amino acid sequences of salmon allele 1 promyostatin (SEQ ID NO: 27; "salmon 1") and salmon allele 2 promyostatin (SEQ ID NO: 29; "salmon 2"). Amino acid position relative to human promyostatin is indicated to left of each row (compare FIG. 1; first amino acid of salmon1 corresponds to human promyostatin 218; first amino acid of salmon2 corresponds to human promyostatin 239). Dashed lines indicate gaps introduced to maximize homology. Relative amino acid positions, including gaps, is indicated along top of each row. Identical residues among sequences are shaded.

DETAILED DESCRIPTION OF THE INVENTION

The present invention provides a substantially purified peptide portion of a promyostatin polypeptide. Promyostatin, which previously has been referred to as growth differentiation factor-8 (GDF-8), comprises an amino terminal prodomain and a C-terminal mature myostatin peptide (see U.S. Pat. No. 5,827,733). Myostatin activity is effected by the mature myostatin peptide following its cleavage from promyostatin. Thus, promyostatin is a precursor polypeptide that is proteolytically cleaved to produce active myostatin. As disclosed herein, the myostatin prodomain can inhibit myostatin activity, GDF-11 activity, or both.

The present invention also provides a substantially purified peptide portion of a pro-GDF-11 polypeptide. Pro-GDF-11, which previously has been referred to generally as GDF-11, comprises an amino terminal prodomain and a C-terminal mature GDF-11 peptide (see International Publication No. WO 98/35019, which is incorporated herein by reference). GDF-11 activity is effected by the mature GDF-11 peptide following its cleavage from pro-GDF-11. Thus, pro-GDF-11, like promyostatin, is a precursor polypeptide that is proteolytically cleaved to produce active GDF-11. As disclosed herein, the GDF-11 prodomain can inhibit GDF-11 activity, myostatin activity, or both.

Promyostatin and pro-GDF-11 are members of the transforming growth factor-β (TGF-β) superfamily, which consists of multifunctional polypeptides that control proliferation, differentiation, and other functions in various cell types. The TGF-β superfamily, which encompasses a group of structurally-related proteins that affect a wide range of differentiation processes during embryonic development, includes, for example, Mullerian inhibiting substance (MIS), which is required for normal male sex development (Behringer et al., Nature 345:167, 1990), Drosophila decapentaplegic (DPP) gene product, which is required for dorsal-ventral axis formation and morphogenesis of the imaginal disks (Padgett et al., Nature 325: 81-84, 1987), the Xenopus Vg-1 gene product, which localizes to the vegetal pole of eggs (Weeks et al., Cell 51: 861-867, 1987), the activins (Mason et al., Biochem. Biophys. Res. Comm. 135:957-964, 1986), which can induce the formation of mesoderm and anterior structures in Xenopus embryos (Thomsen et al., Cell 63:485, 1990), and the bone morphogenic proteins (BMPs, osteogenin, OP-1), which can induce de novo cartilage and bone formation (Sampath et al., J. Biol. Chem. 265: 13198, 1990). The TGF-β family members can influence a variety of differentiation processes, including adipogenesis, myogenesis, chondrogenesis, hematopoiesis, and epithelial cell differentiation (Massague, Cell 49:437, 1987; Massague, Ann. Rev. Biochem. 67:753-791, 1998; each of which is incorporated herein by reference).

Many of the TGF-β family members have regulatory effects (positive or negative) on other peptide growth factors. In particular, certain members of the TGF-β superfamily have expression patterns or possess activities that relate to the function of the nervous system. For example, the inhibins and activins are expressed in the brain (Meunier et al., Proc. Natl. Acad. Sci., USA 85:247, 1988; Sawchenko et al., Nature 334:615, 1988), and activin can function as a nerve cell survival molecule (Schubert et al., Nature 344:868, 1990). Another family member, growth differentiation factor-1 (GDF-1), is nervous system-specific in its expression pattern (Lee, Proc. Natl. Acad. Sci. USA 88:4250, 1991), and other family members such as Vgr-1 (Lyons et al., Proc. Natl. Acad. Sci., USA 86:4554, 1989; Jones et al., Development 111:531, 1991), OP-1 (Ozkaynak et al., J. Biol. Chem. 267: 25220, 1992), and BMP-4 (Jones et al., Development 111:531, 1991), are also expressed in the nervous system. Because skeletal muscle produces a factor or factors that promote the survival of motor neurons (Brown, Trends Neurosci. 7:10, 1984), the expression of myostatin (GDF-8) and GDF-11 in muscle suggests that myostatin and GDF-11 can be trophic factors for neurons. As such, methods for modulating the activity of myostatin, GDF-11, or both can be useful for treating neurodegenerative diseases such as amyotrophic lateral sclerosis or muscular dystrophy, or for maintaining cells or tissues in culture prior to transplantation.

The proteins of the TGF-β family are synthesized as large precursor proteins, which subsequently undergo proteolytic cleavage at a cluster of basic residues approximately 110 to 140 amino acids from the C-terminus, resulting in the formation of a prodomain peptide and a C-terminal mature peptide. The C-terminal mature peptides of the members of this family of proteins are structurally related, and the different family members can be classified into distinct subgroups based on the extent of their homology. Although the homologies within particular subgroups range from 70% to 90% amino acid sequence identity, the homologies between subgroups are significantly lower, generally ranging from 20% to 50%. In each case, the active species appears to be a disulfide-linked dimer of C-terminal peptide fragments.

Promyostatin and pro-GDF-11 polypeptides have been identified in mammalian, avian and piscine species, and myostatin is active in various other species, including vertebrates and invertebrates. During embryonic development and in adult animals, myostatin, for example, is expressed specifically by cells in the myogenic lineage (McPherron et al., Nature 387:83-90, 1997, which is incorporated herein by reference). During early embryogenesis, myostatin is expressed by cells in the myotome compartment of developing somites. At later embryonic stages and in adult animals, myostatin is expressed widely in skeletal muscle tissue, although the levels of expression vary considerably from muscle to muscle. Myostatin expression also is detected in adipose tissue, although at lower levels than in muscle. Similarly, GDF-11 is expressed in skeletal muscle and adipose tissue, as well as in adult thymus, spleen and uterus, and also is expressed in brain at various stages of development.

Figure 1:
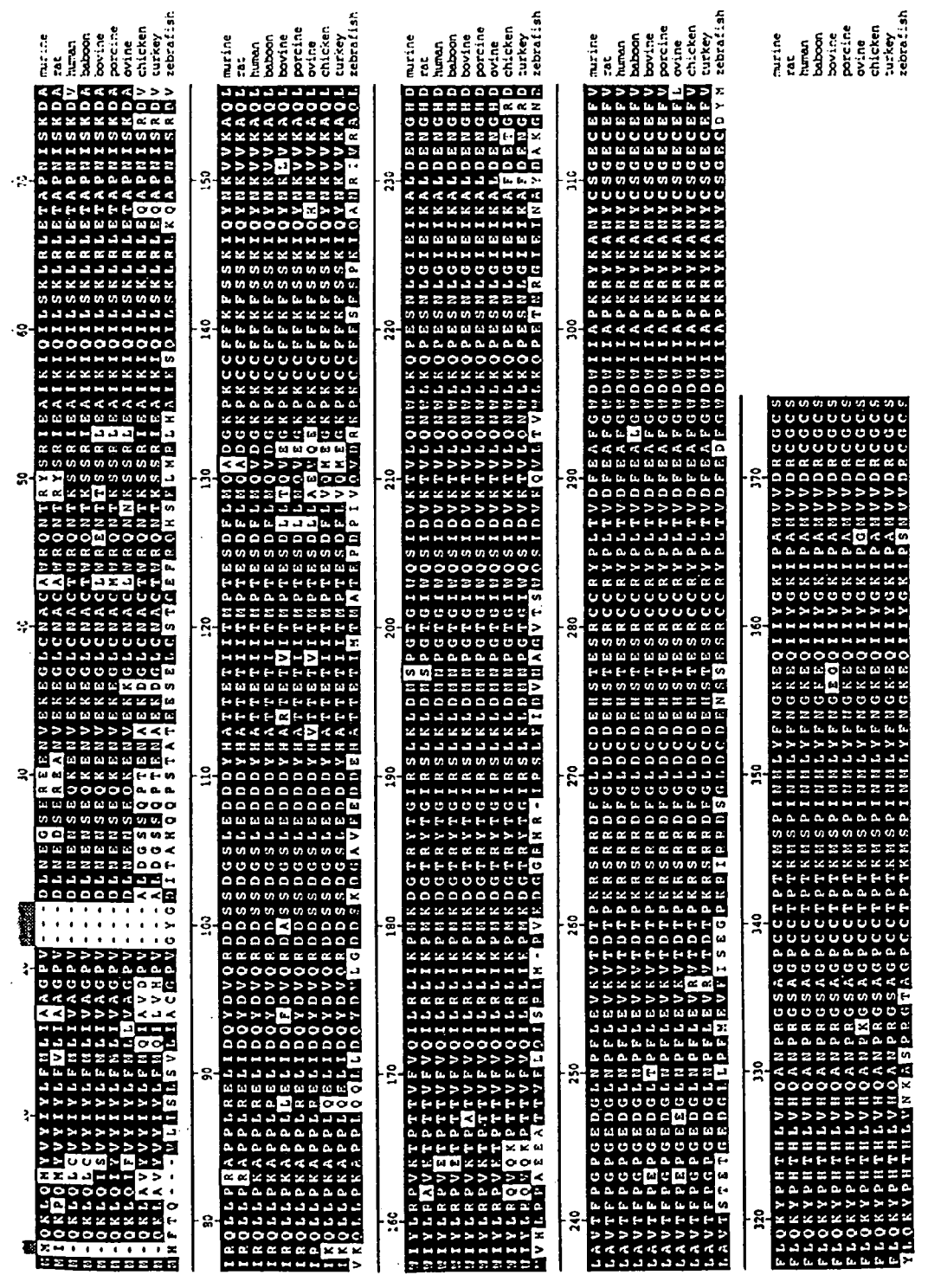

Promyostatin polypeptides from various species share substantial sequence identity, and the amino acid sequences of human, murine, rat and chicken mature myostatin C-terminal sequence are 100% identical (see FIG. 1). Promyostatin polypeptides are exemplified herein (see FIG. 1) by human promyostatin (SEQ ID NO: 2); murine promyostatin (SEQ ID NO: 4); rat promyostatin (SEQ ID NO: 6); baboon promyostatin (SEQ ID NO: 10); bovine promyostatin (SEQ ID NO: 12); porcine promyostatin (SEQ ID NO: 14); ovine promyostatin (SEQ ID NO: 16); chicken promyostatin (SEQ ID NO: 8), turkey promyostatin (SEQ ID NO: 18); and zebrafish promyostatin (SEQ ID NO: 20). Promyostatin polypeptides also are exemplified herein by a polypeptide comprising the portions of salmon allele 1 (SEQ ID NO: 27; "salmon1") and of salmon allele 2 (SEQ ID NO: 29; "salmon2"; see FIG. 2). Nucleic acid molecules encoding these promyostatin polypeptides are disclosed herein as SEQ ID NOS: 1, 3, 5, 9, 11, 13, 15, 7, 17, 19, 26 and 28, respectively (see, also, McPherron and Lee, *Proc. Natl. Acad. Sci., USA* 94: 12457, 1997, which is incorporated herein by reference). A pro-GDF-11 polypeptide is exemplified herein by human pro-GDF-11 (SEQ ID NO: 25), which is encoded by SEQ ID NO: 24.

In view of the extensive conservation among promyostatin polypeptides, particularly among species as diverse as humans and fish, it would be a routine matter to obtain polynucleotides encoding myostatin from any species, including the remainders of the salmon1 and salmon2 sequences, and to identify promyostatin or myostatin expression in any species. In particular, the mature myostatin sequence shares significant homology to other members of the TGF-β superfamily, and myostatin contains most of the residues that are highly conserved among the other family members and in other species. Furthermore, myostatin, like the TGF-β and inhibin βs, contains an extra pair of cysteine residues in addition to the seven cysteine residues present in virtually all other family members. Myostatin is most homologous to Vgr-1 (45% sequence identity). Like other members of the TGF-β superfamily, myostatin is synthesized as a larger precursor promyostatin polypeptide that is proteolytic cleaved into an active myostatin peptide.

Polynucleotides encoding promyostatin polypeptides of various organisms can be identified using well known procedures and algorithms based on identity (or homology) to the disclosed sequences. Homology or identity is often measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. The terms "homology" and "identity," when used herein in the context of two or more nucleic acids or polypeptide sequences, refer to two or more sequences or subsequences that are the same or have a specified percentage of amino acid residues or of nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 20 to 600 positions, for example, amino acid or nucleotide position, usually about 50 to about 200 positions, more usually about 100 to about 150 positions, in which a sequence may be compared to a reference sequence of the same number of contiguous positions after the two sequences are optimally aligned. Methods of alignment of sequence for comparison are well-known in the art. Optimal alignment of sequences for comparison can be conducted, for example, by the local homology algorithm of Smith and Waterman (*Adv. Appl. Math.* 2:482, 1981), by the homology alignment algorithm of Needleman and Wunsch (*J. Mol. Biol.* 48:443, 1970), by the search for similarity method of Person and Lipman (*Proc. Natl. Acad. Sci. USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences.

A number of genome databases are available for comparison, including, for example, a substantial portion of the human genome is available as part of the Human Genome Sequencing Project (J. Roach, http://weber.u.Washington.edu/~roach/human_genome_progress 2.html). In addition, at least twenty-one genomes have been sequenced in their entirety, including, for example, *M. genitalium, M. jannaschii, H. influenzae, E. coli,* yeast (*S. cerevisiae*), and *D. melanogaster*. Significant progress has also been made in sequencing the genomes of model organism such as mouse, *C. elegans,* and *Arabadopsis* sp. Several databases containing genomic information annotated with some functional information are maintained by different organizations, and are accessible via the internet, for example, http://wwwtigr.org/tdb; http://www.genetics.wisc.edu; http://genome-www-.stanford.edu/~ball; http://hiv-web.lanl.gov; http://www.ncbi.nlm.nih.gov; http://www.ebi.ac.uk; http://Pasteur.fr/other/biology; and http://www.genome.wi.mit.edu.

One example of a useful algorithm is BLAST and BLAST 2.0 algorithms, which are described by Altschul et al. (*Nucleic Acids Res.* 25:3389-3402, 1977; *J. Mol. Biol.* 215: 403-410, 1990, each of which is incorporated herein by reference). Software for performing BLAST analyses is publicly available through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff and Henikoff, *Proc. Natl. Acad. Sci. USA* 89: 10915, 1989) alignments (B) of 50, expectation (E) of 10, M=5, N=−4, and a comparison of both strands.

The BLAST algorithm also performs a statistical analysis of the similarity between two sequences (see, for example, Karlin and Altschul, *Proc. Natl. Acad. Sci., USA* 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST"). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443-1445, 1992; Henikoff and Henikoff, *Proteins* 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S. National Library of Medicine, for example, at www.ncbi.nlm.nih.gov.

The parameters used with the above algorithms may be adapted depending on the sequence length and degree of homology studied. In some embodiments, the parameters may be the default parameters used by the algorithms in the absence of instructions from the user.

A polynucleotide encoding a promyostatin can be derived from any organism, including, for example, mouse, rat, cow, pig, human, chicken, turkey, zebrafish, salmon, finfish, other aquatic organisms and other species. Examples of aquatic 3.0 organisms include those belonging to the class Piscina, such as trout, char, ayu, carp, crucian carp, goldfish, roach, whitebait, eel, conger eel, sardine, flying fish, sea bass, sea bream, parrot bass, snapper, mackerel, horse mackerel, tuna, bonito, yellowtail, rockfish, fluke, sole, flounder, blowfish, filefish; those belonging to the class Cephalopoda, such as squid, cuttlefish, octopus; those belonging to the class Pelecypoda, such as clams (e.g., hardshell, Manila, Quahog, Surf, Softshell); cockles, mussels, periwinkles; scallops (e.g., sea, bay, calloo); conch, snails, sea cucumbers; ark shell; oysters (e.g., *C. virginica*, Gulf, New Zealand, Pacific); those belonging to the class Gastropoda such as turban shell, abalone (e.g. green, pink, red); and those belonging to the class Crustacea such as lobster, including but not limited to Spiny, Rock, and American; prawn; shrimp, including but not limited to *M. rosenbergii, P. styllrolls, P. indicus, P. jeponious, P. monodon, P. vannemel, M ensis, S. melantho, N. norvegious*, cold water shrimp; crab, including, but not limited to, Blue, rook, stone, king, queen, snow, brown, dungeness, Jonah, Mangrove, softshelled; squilla, krill, langostinos; crayfish/crawfish, including, but not limited, to Blue, Marron, Red Claw, Red Swamp, Soft-shelled, white; Annelida; Chordata, including, but not limited to, reptiles such as alligators and turtles; Amphibia, including frogs; and Echinodermata, including, but not limited to, sea urchins.

The present invention provides substantially purified peptide portions of a promyostatin polypeptide and substantially purified peptide portions of a pro-GDF-11 polypeptide. As used herein, reference to a "pro-GDF," for example, promyostatin or pro-GDF-11, means the full length polypeptide, including the amino terminal prodomain and the carboxy terminal biologically active GDF peptide. In addition, the prodomain includes a signal peptide (leader sequence), which comprises about the first 15 to 30 amino acids at the amino terminus of the prodomain. The signal peptide can be cleaved from the full length pro-GDF polypeptide, which can be further cleaved at an Arg-Xaa-Xaa-Arg (SEQ ID NO: 21) proteolytic cleavage site.

Reference herein to amino acid residues is made with respect to the full length pro-GDF polypeptides as shown in FIGS. 1 and 2 (see, also, Sequence Listing). It should also be recognized that reference is made herein to particular peptides beginning or ending at "about" a particular amino acid residue. The term "about" is used in this context because it is recognized that a particular protease can cleave a pro-GDF polypeptide at or immediately adjacent to a proteolytic cleavage recognition site, or one or a few amino acids from the recognition site. As such, reference, for example, to a myostatin prodomain having a sequence of about amino acid residues 1 to 263 of SEQ ID NO: 4 would include an amino terminal peptide portion of promyostatin that includes the signal peptide and has a carboxy terminus ending at amino acid residue 257 to amino acid residue 269, preferably at amino acid residue 260 to amino acid residue 266.

Similarly, the signal peptide can be cleaved at any position from about amino acid residue 15 to 30 of a pro-GDF polypeptide, for example, at residue 15, 20, 25 or 30, without affecting the function, for example, of a remaining prodomain. Thus, for convenience, reference is made generally herein to a peptide portion of a pro-GDF polypeptide, from which the signal peptide has been cleaved, as beginning at about amino acid residue 20. However, it will be recognized that cleavage of the signal peptide can be at any amino acid position within about the first 15 to 30 amino terminal amino acids of a pro-GDF polypeptide. As such, reference, for example, to a myostatin prodomain having a sequence of about amino acid residues 20 to 263 of SEQ ID NO: 4 would include a peptide portion of promyostatin that lacks about the first 15 to 30 amino acids of promyostatin, comprising the signal peptide, and that has a carboky terminus ending at amino acid residue 257 to amino acid residue 269, preferably at amino acid residue 260 to amino acid residue 266.

In general, reference is made herein to a pro-GDF polypeptide or a GDF prodomain as beginning at about amino acid 1. In view of the above disclosure, however, it will be recognized that such pro-GDF polypeptides or GDF prodomains that lack the signal peptide also are encompassed within the present invention. Further in this respect, it should be recognized that the presence or absence of a signal peptide in a peptide of the invention can influence, for example, the compartments of a cell through which a peptide, for example, a myostatin prodomain will traverse and to which the peptide ultimately will localize, including whether the peptide will be secreted from the cell. Thus, the present invention further provides a substantially purified signal peptide portion of a pro-GDF polypeptide. As disclosed herein, such a signal peptide can be used to target an agent, particularly a peptide agent, to the same cellular compartments as the naturally occurring GDF from which the signal peptide is derived.

The term "peptide" or "peptide portion" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. Although the term "proteolytic fragment" is used generally herein to refer to a peptide that can be produced by a proteolytic reaction, it should be recognized that the fragment need not necessarily be produced by a proteolytic reaction, but also can be produced using methods of chemical synthesis or methods of recombinant DNA technology, as discussed in greater detail below, to produce a synthetic peptide that is equivalent to a proteolytic fragment. In view of the disclosed homology of promyostatin with other members of the TGF-β superfamily, it will be recognized that a peptide of the invention is characterized, in part, in that it is not present in previously disclosed members of this superfamily. Whether a peptide portion of a promyostatin or pro-GDF-11 polypeptide is present in a previously disclosed member of the TGF-β superfamily readily can be determined using the computer algorithms described above.

Generally, a peptide of the invention contains at least about six amino acids, usually contains about ten amino acids, and can contain fifteen or more amino acids, particularly twenty or more amino acids. It should be recognized that the term "peptide" is not used herein to suggest a particular size or number of amino acids comprising the molecule, and that a peptide of the invention can contain up to several amino acid residues or more. For example, a full length mature C-terminal myostatin peptide contains more than 100 amino acids and a full length prodomain peptide can contain more than 260 amino acids.

As used herein, the term "substantially purified" or "substantially pure" or "isolated" means that the molecule being referred to, for example, a peptide or a polynucleotide, is in a form that is relatively free of proteins, nucleic acids, lipids, carbohydrates or other materials with which it is naturally associated. Generally, a substantially pure peptide, polynucleotide, or other molecule constitutes at least twenty percent of a sample, generally constitutes at least about fifty percent of a sample, usually constitutes at least about eighty percent of a sample, and particularly constitutes about ninety percent or ninety-five percent or more of a sample. A determination that a peptide or a polynucleotide of the invention is substantially pure can be made using well known methods, for example, by performing electrophoresis and identifying the particular molecule as a relatively discrete band. A substantially pure polynucleotide, for example, can be obtained by cloning the polynucleotide, or by chemical or enzymatic synthesis. A substantially pure peptide can be obtained, for example, by a method of chemical synthesis, or using methods of protein purification, followed by proteolysis and, if desired, further purification by chromatographic or electrophoretic methods.

A peptide of the invention can be identified by comparison to a promyostatin or pro-GDF-11 sequence and determining that the amino acid sequence of the peptide is contained within the promyostatin or pro-GDF-11 polypeptide sequence, respectively. It should be recognized, however, that a peptide of the invention need not be identical to a corresponding amino acid sequence of promyostatin or pro-GDF-11. Thus, a peptide of the invention can correspond to an amino acid sequence of a promyostatin polypeptide, for example, but can vary from a naturally occurring sequence, for example, by containing one or more D-amino acids in place of a corresponding L-amino acid; or by containing one or more amino acid analogs, for example, an amino acid that has been derivatized or otherwise modified at its reactive side chain. Similarly, one or more peptide bonds in the peptide can be modified. In addition, a reactive group at the amino terminus or the carboxy terminus or both can be modified. Such peptides can be modified, for example, to have improved stability to a protease, an oxidizing agent or other reactive material the peptide may encounter in a biological environment, and, therefore, can be particularly useful in performing a method of the invention. Of course, the peptides can be modified to have decreased stability in a biological environment such that the period of time the peptide is active in the environment is reduced.

The sequence of a peptide of the invention also can be modified in comparison to the corresponding sequence in a promyostatin or pro-GDF-11 polypeptide by incorporating a conservative amino acid substitution for one or a few amino acids in the peptide. Conservative amino acid substitutions include the replacement of one amino acid residue with another amino acid residue having relatively the same chemical characteristics, for example, the substitution of one hydrophobic residue such as isoleucine, valine, leucine or methionine for another, or the substitution of one polar residue for another, for example, substitution of arginine for lysine; or of glutamic for aspartic acid; or of glutamine for asparagine; or the like. Examples of positions of a promyostatin polypeptide that can be modified are evident from examination of FIG. 1, which shows various amino acid differences in the myostatin prodomain and mature myostatin peptide that do not substantially affect promyostatin or myostatin activity.

The present invention also provides a substantially purified proteolytic fragment of a growth differentiation factor (GDF) polypeptide (a pro-GDF polypeptide) or a functional peptide portion thereof. Proteolytic fragments of a pro-GDF polypeptide are exemplified herein by proteolytic fragments of a promyostatin polypeptide and proteolytic fragments of a pro-GDF-11 polypeptide. As disclosed herein, a peptide portion of a pro-GDF polypeptide that is equivalent to a proteolytic fragment of a pro-GDF can be produced by a chemical method or a recombinant DNA method. In view of the present disclosure, proteolytic fragments of other GDF polypeptides readily can be made and used.

In general, peptides corresponding to proteolytic fragments of a pro-GDF polypeptide are exemplified by a carboxy terminal (C-terminal) mature GDF fragment, which can interact specifically with a GDF receptor and affect GDF signal transduction, and an amino terminal prodomain fragment, which can include a signal peptide and, as disclosed herein, can interact specifically with a pro-GDF polypeptide or mature GDF peptide and affect its ability to effect GDF signal transduction. For example, proteolytic fragments of a promyostatin polypeptide include a C-terminal mature myostatin peptide, which can interact specifically with a myostatin receptor and induce myostatin signal transduction; and an amino terminal prodomain fragment, which can interact specifically with myostatin, thereby reducing or inhibiting the ability of myostatin to induce myostatin signal transduction.

A proteolytic fragment of a pro-GDF polypeptide, or a functional peptide portion thereof, is characterized, in part, by having or affecting an activity associated with the stimulation or inhibition of GDF signal transduction. For example, a promyostatin polypeptide or functional peptide portion thereof can have myostatin receptor binding activity, myostatin signal transduction stimulatory or inhibitory activity, myostatin binding activity, promyostatin binding activity, or a combination thereof. Thus, the term "functional peptide portion," when used herein in reference to a pro-GDF polypeptide, means a peptide portion of the pro-GDF polypeptide that can interact specifically with its receptor and stimulate or inhibit GDF signal transduction; that can interact specifically with a mature GDF or a pro-GDF; or that exhibits cellular localization activity, i.e., the activity of a signal peptide. It should be recognized that a functional peptide portion of full length mature myostatin peptide, for example, need not have the same activity of the mature myostatin, including the ability to stimulate myostatin signal transduction, since functional peptide portions of the mature peptide can have, for example, an ability to specifically interact with a myostatin receptor without also having the ability to activate the signal transduction pathway. Methods for identifying such a functional peptide portion of a pro-GDF polypeptide, which can be useful as a myostatin antagonist, are disclosed herein or otherwise known in the art. Thus, in one embodiment, a functional peptide portion of a promyostatin polypeptide can interact specifically with a myostatin receptor, and can act as an agonist to stimulate myostatin signal transduction or as an antagonist to reduce or inhibit myostatin signal transduction.

In another embodiment, a functional peptide portion of a promyostatin polypeptide can interact specifically with a promyostatin polypeptide or with a mature myostatin peptide, thereby blocking myostatin signal transduction. Such a functional peptide portion of promyostatin can act, for example, by preventing cleavage of a promyostatin polypeptide to mature myostatin; by forming a complex with a mature myostatin peptide; or by some other mechanism. Where a peptide-myostatin complex is formed, the complex can block myostatin signal transduction, for example, by reducing or inhibiting the ability of the myostatin to interact specifically with its receptor, or by binding to the receptor in the form that lacks the ability to induce myostatin signal transduction.

Proteolytic fragments of a pro-GDF polypeptide can be produced by cleavage of the polypeptide at a proteolytic cleavage site having a consensus amino acid sequence Arg-Xaa-Xaa-Arg (SEQ ID NO: 21). Such proteolytic recognition sites are exemplified by the Arg-Ser-Arg-Arg (SEQ ID NO: 22) sequence shown as amino acid residues 263 to 266 in SEQ ID NO: 1 (promyostatin) or amino acid residues 295 to 298 of SEQ ID NO: 25 (human pro-GDF-1; see, also, relative positions 267 to 270 of FIG. 2), and by the Arg-Ile-Arg-Arg (SEQ ID NO: 23) sequence shown as amino acid residues 263 to 266 in SEQ ID NO: 20.

In addition to the proteolytic cleavage site for the signal peptide, promyostatin polypeptides, for example, contain two additional potential proteolytic processing sites (Lys-Arg and Arg-Arg). Cleavage of a promyostatin polypeptide at or near the latter proteolytic processing site, which is contained within the consensus Arg-Xaa-Xaa-Arg (SEQ ID NO: 21) proteolytic cleavage recognition site (see, for example, amino acid residues 263 to 266 of SEQ ID NO: 2), generates a biologically active C-terminal mature human myostatin fragment. The exemplified full length mature myostatin peptides contain about 103 to about 109 amino acids and have a predicted molecular weight of approximately 12,400 daltons (Da). In addition, myostatin can form dimers, which have an expected molecular weight of about 23 to 30 kiloDaltons (kDa). The dimers can be myostatin homodimers or can be heterodimers, for example, with GDF-11 or another GDF or TGF-β family member.

A proteolytic fragment of the invention is exemplified by a GDF prodomain, for example, a myostatin prodomain, which includes about amino acid residues 20 to 262 of a promyostatin polypeptide, or a functional peptide portion thereof, or a GDF-11 prodomain, which includes about amino acid residues 20 to 295 of a pro-GDF-11 polypeptide, or a functional peptide portion thereof, each of which can further contain the signal peptide comprising about amino acids 1 to 20 of the respective pro-GDF polypeptide. Myostatin prodomains are further exemplified by about amino acid residues 20 to 263 as set forth in SEQ ID NO: 4 and SEQ ID NO: 6; as well as by about amino acid residues about 20 to 262 as set forth in SEQ ID NO: 2, SEQ ID NO: 10, SEQ ID NO: 12, SEQ ID NO: 8, SEQ ID NO: 18, SEQ ID NO: 14, SEQ ID NO: 16, SEQ ID NO: 20, which can be produced by proteolytic cleavage of a corresponding promyostatin polypeptide, can be chemically synthesized, or can be expressed from a recombinant polynucleotide encoding the proteolytic fragment. A functional peptide portion of a myostatin prodomain is exemplified by a peptide portion of a myostatin prodomain that can interact specifically with myostatin or with promyostatin. A GDF-11 prodomain is exemplified by about amino acid residues 20 to 295 of SEQ ID NO: 25, which can further include the signal peptide comprising about amino acid residues 1 to 20 of SEQ ID NO: 25, and a functional peptide portion of a GDF-11 prodomain is exemplified by a peptide portion of a GDF-11 prodomain that can specifically interact with mature GDF-11 or a pro-GDF-11 polypeptide. Preferably, the functional peptide portion of a GDF prodomain inhibits the ability of the corresponding GDF or a related GDF to stimulate signal transduction, for example, by reducing or inhibiting the ability of the GDF to interact specifically with its receptor, or by binding to the receptor as an inactive complex. In one embodiment, the present invention provides a functional fragment of a pro-GDF polypeptide, particularly a functional fragment of a GDF prodomain, operably linked to a GDF signal peptide, preferably a myostatin signal peptide or a GDF-11 signal peptide comprising about the first 15 to 30 amino terminal amino acids of promyostatin or pro-GDF-11, respectively.

As disclosed herein, a myostatin prodomain or GDF-11 prodomain can interact with mature myostatin, GDF-11, or both, thereby reducing or inhibiting the ability of the mature GDF to interact specifically with its receptor (see Examples 7 and 8). Thus, a functional peptide portion of a myostatin prodomain, for example, can be obtained by examining peptide portions of a myostatin prodomain using methods as provided herein, and identifying functional peptide portions of the prodomain that can interact specifically with myostatin or with promyostatin and can reduce or inhibit the ability of myostatin to interact specifically with a myostatin receptor or to stimulate myostatin signal transduction.

A functional peptide portion of a myostatin prodomain that can specifically interact with myostatin, or a functional peptide portion of another GDF prodomain, also can be identified using any of various assays known to be useful for identifying specific protein-protein interactions. Such assays include, for example, methods of gel electrophoresis, affinity chromatography, the two hybrid system of Fields and Song (*Nature* 340:245-246, 1989; see, also, U.S. Pat. No. 5,283,173; Fearon et al., *Proc. Natl. Acad. Sci., USA* 89:7958-7962, 1992; Chien et al., *Proc. Natl. Acad. Sci. USA* 88:9578-9582, 1991; Young, *Biol. Reprod.* 58:302-311 (1998), each of which is incorporated herein by reference), the reverse two hybrid assay (Leanna and Hannink, *Nucl. Acids Res.* 24:3341-3347, 1996, which is incorporated herein by reference), the repressed transactivator system (U.S. Pat. No. 5,885,779, which is incorporated herein by reference), the phage display system (Lowman, *Ann. Rev. Biophys. Biomol. Struct.* 26:401-424, 1997, which is incorporated herein by reference), GST/HIS pull down assays, mutant operators (WO 98/01879, which is incorporated herein by reference), the protein recruitment system (U.S. Pat. No. 5,776,689, which is incorporated herein by reference), and the like (see, for example, Mathis, *Clin. Chem.* 41:139-147, 1995 Lam, *Anticancer Drug Res.* 12:145-167, 1997; Phizicky et al., *Microbiol. Rev.* 59:94-123, 1995; each of which is incorporated herein by reference).

A functional peptide portion of a GDF prodomain also can be identified using methods of molecular modeling. For example, an amino acid sequence of a mature myostatin peptide can be entered into a computer system having appropriate modeling software, and a three dimensional representation of the myostatin ("virtual myostatin") can be produced. A promyostatin amino acid sequence also can be entered into the computer system, such that the modeling software can simulate portions of the promyostatin sequence, for example, portions of the prodomain, and can identify those peptide portions of the prodomain that can interact specifically with the virtual myostatin. A base line for a specific interaction can be predefined by modeling the virtual myostatin and a full length promyostatin prodomain, and identifying the amino acid residues in the virtual myostatin that are "contacted" by the prodomain, since such an interaction is known to inhibit the activity of the myostatin.

It should be recognized that such methods, including two hybrid assays and molecular modeling methods, also can be used to identify other specifically interacting molecules encompassed within the present invention. Thus, methods such as the two hybrid assay can be used to identify a GDF receptor such as a myostatin receptor using, for example, a myostatin peptide or a peptide portion thereof that specifically interacts with an Act RIIA or Act RIIB receptor as one binding component of the assay, and identifying a GDF receptor, which specifically interacts with the myostatin peptide. Similarly, methods of molecular modeling can be used to identify an agent that interacts specifically with a mature GDF peptide such as mature myostatin, or with a GDF receptor and, therefore, can be useful as an agonist or an antagonist of signal transduction mediated by the GDF or the GDF receptor. Such an agent can be, for example, a functional peptide portion of a myostatin prodomain or GDF-11 prodomain, or a chemical agent that mimics the action of the GDF prodomain.

Modeling systems useful for the purposes disclosed herein can be based on structural information obtained, for example, by crystallographic analysis or nuclear magnetic resonance analysis, or on primary sequence information (see, for example, Dunbrack et al., "Meeting review: the Second meeting on the Critical Assessment of Techniques for Protein Structure Prediction (CASP2) (Asilomar, Calif., Dec. 13-16, 1996). *Fold Des.* 2(2): R27-42, (1997); Fischer and Eisenberg, *Protein Sci.* 5:947-55, 1996; (see, also, U.S. Pat. No. 5,436,850); Havel, *Prog. Biophys. Mol. Biol.* 56:43-78, 1991; Lichtarge et al., *J. Mol. Biol.* 274:325-37, 1997; Matsumoto et al., *J. Biol. Chem.* 270:19524-31, 1995; Sali et al., *J. Biol. Chem.* 268:9023-34, 1993; Sali, *Molec. Med. Today* 1:270-7, 1995a; Sali, *Curr. Opin. Biotechnol.* 6:437-51, 1995b; Sali et al., *Proteins* 23: 318-26, 1995c; Sali, *Nature Struct. Biol.* 5: 1029-1032, 1998; U.S. Pat. No. 5,933,819; U.S. Pat. No. 5,265,030, each of which is incorporated herein by reference).

The crystal structure coordinates of a promyostatin polypeptide or a GDF receptor can be used to design compounds that bind to the protein and alter its physical or physiological properties in a variety of ways. The structure coordinates of the protein can also be used to computationally screen small molecule data bases for agents that bind to the polypeptide to develop modulating or binding agents, which can act as agonists or antagonists of GDF signal transduction. Such agents can be identified by computer fitting kinetic data using standard equations (see, for example, Segel, "Enzyme Kinetics" (J. Wiley & Sons 1975), which is incorporated herein by reference).

Methods of using crystal structure data to design inhibitors or binding agents are known in the art. For example, GDF receptor coordinates can be superimposed onto other available coordinates of similar receptors, including receptors having a bound inhibitor, to provide an approximation of the way the inhibitor interacts with the receptor. Computer programs employed in the practice of rational drug design also can be used to identify compounds that reproduce interaction characteristics similar to those found, for example, between a mature myostatin and a co-crystallized myostatin prodomain. Detailed knowledge of the nature of the specific interactions allows for the modification of compounds to alter or improve solubility, pharmacokinetics, and the like, without affecting binding activity.

Computer programs for carrying out the activities necessary to design agents using crystal structure information are well known. Examples of such programs include, Catalyst Databases™—an information retrieval program accessing chemical databases such as BioByte Master File, Derwent WDI and ACD; Catalyst/HYPO™—generates models of compounds and hypotheses to explain variations of activity with the structure of drug candidates; Ludi™—fits molecules into the active site of a protein by identifying and matching complementary polar and hydrophobic groups; and Leapfrog™—"grows" new ligands using a genetic algorithm with parameters under the control of the user.

Various general purpose machines can be used with such programs, or it may be more convenient to construct more specialized apparatus to perform the operations. Generally, the embodiment is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

Each such program can be implemented in any desired computer language, including, for example, machine, assembly, high level procedural, or object oriented programming languages, to communicate with a computer system. In any case, the language may be a compiled or interpreted language. The computer program will typically be stored on a storage media or device, for example, a ROM, CD-ROM, magnetic or optical media, or the like, that is readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Embodiments of the invention include systems, for example, internet based systems, particularly computer systems which store and manipulate coordinate information obtained by crystallographic or NMR analysis, or amino acid or nucleotide sequence information, as disclosed herein. As used herein, the term "computer system" refers to the hardware components, software components, and data storage components used to analyze coordinates or sequences as set forth herein. The computer system typically includes a processor for processing, accessing and manipulating the sequence data. The processor can be any well known type of central processing unit, for example, a Pentium II or Pentium III processor from Intel Corporation, or a similar processor from Sun, Motorola, Compaq, Advanced MicroDevices or International Business Machines.

Typically the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In one embodiment, the computer system includes a processor connected to a bus, which is connected to a main memory, preferably implemented as RAM, and one or more internal data storage devices such as a hard drive or other computer readable media having data recorded thereon. In some embodiments, the computer system further includes one or more data retrieving devices for reading the data stored on the internal data storage devices.

The data retrieving device may represent, for example, a floppy disk drive, a compact disk drive, a magnetic tape drive, or a modem capable of connection to a remote data storage system (e.g., via the internet). In some embodiments, the internal data storage device is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device.

The computer system generally include a display, which is used to display output to a computer user. It should also be noted that the computer system can be linked to other computer systems in a network or wide area network to provide centralized access to the computer system.

Where it is desired to identify a chemical entity that interacts specifically with myostatin or with a GDF receptor, any of several methods to screen chemical entities or fragments for their ability to interact specifically with the molecule can be used. This process may begin by visual inspection, for example, of myostatin and a myostatin prodomain on the computer screen. Selected peptide portions of the prodomain, or chemical entities that can act as mimics, then can be positioned in a variety of orientations, or docked, within an individual binding site of the myostatin. Docking can be accomplished using software such as Quanta and Sybyl, followed by energy minimization and molecular dynamics with standard molecular mechanics forcefields, such as CHARMM and AMBER.

Specialized computer programs can be particularly useful for selecting peptide portions of a prodomain, or chemical entities useful, for example, as a GDF receptor agonist or antagonist. Such programs include, for example, GRID (Goodford, *J. Med. Chem.*, 28:849-857, 1985; available from Oxford University, Oxford, UK); MCSS (Miranker and Karplus, *Proteins: Structure. Function and Genetics* 11:29-34, 1991, available from Molecular Simulations, Burlington Mass.); AUTODOCK (Goodsell and Olsen, *Proteins: Structure. Function, and Genetics* 8:195-202, 1990, available from Scripps Research Institute, La Jolla Calif.); DOCK (Kuntz, et al., *J. Mol. Biol.* 161:269-288, 1982, available from University of California, San Francisco Calif.), each of which is incorporated herein by reference.

Suitable peptides or agents that have been selected can be assembled into a single compound or binding agent. Assembly can be performed by visual inspection of the relationship of the fragments to each other on the three-dimensional image displayed on a computer screen, followed by manual model building using software such as Quanta or Sybyl. Useful programs to aid one of skill in the art in connecting the individual chemical entities or fragments include, for example, CAVEAT (Bartlett et al, *Special Pub., Royal Chem. Soc.* 78:182-196, 1989, available from the University of California, Berkeley Calif.); 3D Database systems such as MACCS-3D (MDL Information Systems, San Leandro CA; for review, see Martin. *J. Med. Chem.* 35:2145-2154, 1992); HOOK (available from Molecular Simulations, Burlington, Mass.), each of which is incorporated herein by reference.

In addition to the method of building or identifying such specifically interacting agents in a step-wise fashion, one fragment or chemical entity at a time as described above, the agents can be designed as a whole or de novo using either an empty active site or, optionally, including some portions of a known agent that specifically interacts, for example, a full length myostatin prodomain, which interacts specifically with myostatin. Such methods include, for example, LUDI (Bohm, *J. Comp. Aid. Molec. Design* 6:61-78, 1992, available from Biosym Technologies, San Diego Calif.); LEGEND (Nishibata and Itai, *Tetrahedron* 47:8985, 1991, available from Molecular Simulations, Burlington Mass.); LeapFrog (available from Tripos Associates, St. Louis Mo.), and those described by Cohen et al. (*J. Med. Chem.* 33:883-894, 1990) and by Navia and Murcko, *Curr. Opin. Struct. Biol.* 2:202-210, 1992, each of which is incorporated herein by reference).

Specific computer software is available in the art to evaluate compound deformation energy and electrostatic interaction. Examples of programs designed for such uses include Gaussian 92, revision C (Frisch, Gaussian, Inc., Pittsburgh Pa., 1992); AMBER, version 4.0 (Kollman, University of California at San Francisco, 1994); QUANTA/CHARMM (Molecular Simulations, Inc., Burlington Mass., 1994); and Insight II/Discover (Biosysm Technologies Inc., San Diego Calif., 1994). These programs may be implemented using, for example, a Silicon Graphics workstation, IRIS 4D/35 or IBM RISC/6000 workstation model 550. Other hardware systems and software packages will be known to those skilled in the art of which the speed and capacity are continually modified.

A molecular modeling process for identifying an agent that interacts specifically with a molecule of interest, for example, with a mature GDF peptides such as mature myostatin, or with a GDF receptor can be performed as disclosed herein. In a first step, a virtual representation of a target molecule, for example, myostatin, is performed. Thus, in one embodiment, the present invention provides a virtual representation of a target molecule, wherein the target molecule is selected from a pro-GDF polypeptide, for example, promyostatin; a peptide portion of a pro-GDF polypeptide; a GDF receptor; and a relevant domain of a GDF receptor, for example, a GDF binding domain. The virtual representation of the target molecule can be displayed or can be maintained in a computer system memory. The process begins at a start state, comprising the virtual target molecule, then moves to a state wherein a database containing one or more virtual test molecules stored to a memory in the computer system. As discussed above, the memory can be any type of memory, including RAM or an internal storage device.

The process then moves to a state wherein the ability of a virtual first test molecule to specifically interact with the virtual target molecule is determined, wherein the database containing the virtual test molecule, which can be one of a population of test molecules, is opened for analysis of the an interaction of the virtual target molecule and virtual test molecule, and the analysis is made. A determination of a specific interaction can be made based on calculations performed by software maintained in the computer system, or by comparison to a predetermined specific interaction, which can be stored in a memory in the computer system and accessed as appropriate.

The process then moves to a state wherein, where a specific interaction is detected, the virtual test molecule is displayed, or is stored in a second database on the computer. If appropriate, the process is repeated for the virtual target molecule and a second virtual test molecule, a third virtual test molecule, and so on, as desired.

If a determination is made that a virtual test molecule specifically interacts with the virtual target molecule, the identified virtual test molecule is moved from the database and can be displayed to the user. This state notifies the user that the molecule with the displayed name or structure interacts specifically with the target molecule within the constraints that were entered. Once the name of the identified test molecule is displayed to the user, the process moves to a decision state, wherein a determination is made whether more virtual test molecules exist in the database or are to be examined. If no more molecules exist in the database, then the process terminates at an end state. However, if more test molecules exist in the database, then the process moves to a state, wherein a pointer is moved to the next test molecule in the database so that it can be examined for specific binding activity. In this manner, the new molecule is examined for the ability to interact specifically with the virtual target molecule.

Such methods as described above can be used in various aspects encompassed within the claimed invention. Thus, the methods can be used to identify a peptide portion of a promyostatin prodomain that can interact specifically with myostatin and reduce or inhibit the ability of myostatin to interact with its receptor or otherwise affect the ability of the myostatin to effect signal transduction. Similarly, the methods can be used to identify small organic molecules that mimic the action of a GDF prodomain, thereby reducing or inhibiting myostatin or GDF-11 signal transduction. The methods also can be used to identify agents that interact specifically with a GDF receptor, for example, an Act RIIA, Act RIIB or other GDF receptor, such agents being useful as GDF receptor agonists or antagonists, which can modulate GDF signal transduction in a cell. In addition, the methods provide a means to identify previously unknown pro-GDF polypeptides or GDF receptors, for example, by identifying conserved structural features of the particular polypeptides.

Similar to other members of the TGF-β superfamily, active GDF peptides are expressed as precursor polypeptides, which are cleaved to a mature, biologically active form. Accordingly, in still another embodiment, the proteolytic fragment of a pro-GDF polypeptide is a mature GDF peptide, or a functional peptide portion of a mature GDF peptide, where, as discussed above, the functional peptide portion can have the activity of a GDF agonist or antagonist. The proteolytic fragment can be a mature C-terminal myostatin peptide, which includes about amino acid residues 268 to 374 of a promyostatin polypeptide (see FIG. 1; see, also, FIG. 2), or a mature C-terminal GDF-11 peptide, which includes about amino acid residues 299 to 407 of a pro-GDF-11 polypeptide. Full length mature myostatin peptides are exemplified by amino acid residues about 268 to 375 as set forth in SEQ ID NO: 4 and SEQ ID NO: 6; by amino acid residues about 267 to 374 as set forth in SEQ ID NO: 2, SEQ ID NO: 10, SEQ ID NO: 12, SEQ ID NO: 8, SEQ ID NO: 18, SEQ ID NO: 14, SEQ ID NO: 16, and SEQ ID NO: 20, and by amino acid residues about 49 to 157 of SEQ ID NO:27 and amino acid residues about 28 to 136 of SEQ ID NO: 29. A full length mature GDF-11 peptide is exemplified by amino acid residues about 299 to 407 of SEQ ID NO: 25. Functional peptide portions of the mature GDF peptides are exemplified by peptide portions of mature myostatin or mature GDF-11 that have an agonist or antagonist activity with respect to the activity of a mature GDF peptide. Preferably, the mature GDF peptide activity is an ability to interact specifically with its receptor.

As disclosed herein, a mature myostatin peptide (referred to herein generally as "myostatin") can induce myostatin signal transduction activity by interacting specifically with a myostatin receptor expressed on the surface of a cell (see Example 7). Thus, a functional peptide portion of myostatin can be obtained by examining peptide portions of a mature myostatin peptide using a method as described herein (Example 7) or otherwise known in the art, and identifying functional peptide portions of myostatin that specifically interact with a myostatin receptor, for example, an activin type IIA receptor (Act RIIA) or Act RIIB receptor expressed on a cell.

A myostatin prodomain can reduce or inhibit myostatin signal transduction activity. In one embodiment, the myostatin prodomain can interact specifically with myostatin, thereby reducing or inhibiting the ability of the myostatin peptide to interact specifically with its receptor. As disclosed herein, a precursor promyostatin also lacks the ability to interact specifically with a myostatin receptor, and, therefore, mutations in promyostatin that reduce or inhibit the ability of promyostatin to be cleaved into mature myostatin provide a means to reduce or inhibit myostatin signal transduction. Accordingly, in another embodiment, the present invention provides a mutant pro-GDF polypeptide, which contains one or more amino acid mutations that disrupt proteolytic cleavage of the mutant pro-GDF to an active mature GDF peptide.

A mutant pro-GDF polypeptide of the invention can have a mutation that affects cleavage at a proteolytic cleavage site such as the consensus proteolytic cleavage recognition site Arg-Xaa-Xaa-Arg (SEQ ID NO: 21), which is present in pro-GDF polypeptides. Thus, the mutation can be a mutation of an Arg residue of SEQ ID NO: 21, such that a mutant promyostatin, for example, cannot be cleaved into a myostatin prodomain and a mature myostatin peptide. However, the mutation also can be at a site other than the proteolytic cleavage site, and can alter the ability of the protease to bind to the pro-GDF polypeptide so as to effect proteolysis at the cleavage site. A mutant pro-GDF polypeptide of the invention, for example, a mutant promyostatin or mutant pro-GDF-11 can have a dominant negative activity with respect to myostatin or GDF-11 and, therefore, can be useful for reducing or inhibiting myostatin or GDF-11 signal transduction in a cell.

The present invention also provides a substantially purified polynucleotide, which encodes a peptide portion of a promyostatin polypeptide or a mutant promyostatin, or a peptide portion of a pro-GDF-11 polypeptide or mutant pro-GDF-11, as described above. As discussed in greater detail below, the invention also provides polynucleotides useful as agents for modulating the affect of myostatin on a cell, and further provides a polynucleotide encoding a GDF receptor, or functional peptide portion thereof. Examples of such polynucleotides are provided in the following disclosure. As such, it should be recognized that the following disclosure is relevant to the various embodiments of the invention as disclosed herein.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond (see above).

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986 (1994); Ecker and Crooke, *BioTechnology* 13: 351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Where a polynucleotide encodes a peptide, for example, a peptide portion of promyostatin or a peptide agent, the coding sequence generally is contained in a vector and is operatively linked to appropriate regulatory elements, including, if desired, a tissue specific promoter or enhancer. The encoded peptide can be further operatively linked, for example, to peptide tag such as a His-6 tag or the like, which can facilitate identification of expression of the agent in the target cell. A polyhistidine tag peptide such as His-6 can be detected using a divalent cation such as nickel ion, cobalt ion, or the like. Additional peptide tags include, for example, a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione. Such tags can provide the additional advantage that they can facilitate isolation of the operatively linked peptide or peptide agent, for example, where it is desired to obtain a substantially purified peptide corresponding to a proteolytic fragment of a myostatin polypeptide.

As used herein, the term "operatively linked" or "operatively associated" means that two or more molecules are positioned with respect to each other such that they act as a single unit and effect a function attributable to one or both molecules or a combination thereof. For example, a polynucleotide sequence encoding a peptide of the invention can be operatively linked to a regulatory element, in which case the regulatory element confers its regulatory effect on the polynucleotide similarly to the way in which the regulatory element would effect a polynucleotide sequence with which it normally is associated with in a cell. A first polynucleotide coding sequence also can be operatively linked to a second (or more) coding sequence such that a chimeric polypeptide can be expressed from the operatively linked coding sequences. The chimeric polypeptide can be a fusion polypeptide, in which the two (or more) encoded peptides are translated into a single polypeptide, i.e., are covalently bound through a peptide bond; or can be translated as two discrete peptides that, upon translation, can operatively associate with each other to form a stable complex.

A chimeric polypeptide generally demonstrates some or all of the characteristics of each of its peptide components. As such, a chimeric polypeptide can be particularly useful in performing methods of the invention, as disclosed herein. For example, in one embodiment, a method of the invention can modulate myostatin signal transduction in a cell. Thus, where one peptide component of a chimeric polypeptide encodes a cell compartment localization domain and a second peptide component encodes a dominant negative Smad polypeptide, the functional chimeric polypeptide can be translocated to the cell compartment designated by the cell compartment localization domain and can have the dominant negative activity of the Smad polypeptide, thereby modulating myostatin signal transduction in the cell.

Cell compartmentalization domains are well known and include, for example, a plasma membrane localization domain, a nuclear localization signal, a mitochondrial membrane localization signal, an endoplasmic reticulum localization signal, or the like (see, for example, Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). Such a domain can be useful to target an agent to a particular compartment in the cell, or to target the agent for secretion from a cell. For example, the kinase domain of a myostatin receptor such as Act RIIB generally is associated with the inner surface of the plasma membrane. Thus, a chimeric polypeptide comprising a dominant negative myostatin receptor kinase domain, for example, a dominant negative Act RIIB receptor, which lacks kinase activity, can further comprise a plasma membrane localization domain, thereby localizing the dominant negative Act RIIB kinase domain to the inner cell membrane.

As disclosed herein, a pro-GDF signal peptide has cellular localization activity. As used herein, the term "cellular localization activity" refers to the ability of a signal peptide to direct translocation of a peptide operably linked thereto to one or more specific intracellular compartments or to direct secretion of the molecule from the cell. As such, a pro-GDF signal peptide can be particularly useful for directing translocation of a peptide or other agent operably linked to the signal peptide to the same intracellular compartments as a naturally expressed GDF having substantially the same signal peptide. Furthermore, the signal peptide, for example, a promyostatin signal peptide comprising about the first 15 to 30 amino acids of promyostatin, can direct secretion of an operably linked agent from the cell through the same pathway as the naturally occurring pro-GDF having comprising the signal peptide. Thus, particularly useful agents for performing a method of the invention include a GDF prodomain or functional peptide portion thereof that is operably linked to a GDF signal peptide, preferably a promyostatin or pro-GDF-11 signal peptide.

A polynucleotide of the invention, including a polynucleotide agent useful in performing a method of the invention, can be contacted directly with a target cell. For example, oligonucleotides useful as antisense molecules, ribozymes, or triplexing agents can be directly contacted with a target cell, whereupon the enter the cell and effect their function. A polynucleotide agent also can interact specifically with a polypeptide, for example, a myostatin receptor (or myostatin), thereby altering the ability of myostatin to interact specifically with the receptor. Such polynucleotides, as well as methods of making and identifying such polynucleotides, are disclosed herein or otherwise well known in the art (see, for example, O'Connell et al., *Proc. Natl. Acad. Sci. USA* 93:5883-5887, 1996; Tuerk and Gold, *Science* 249:505-510, 1990; Gold et al., *Ann. Rev. Biochem.* 64:763-797, 1995; each of which is incorporated herein by reference).

A polynucleotide of the invention, which can encode a peptide portion of a pro-GDF polypeptide such as promyostatin, or can encode a mutant promyostatin polypeptide, or can encode a GDF receptor or functional peptide portion thereof, or can be a polynucleotide agent useful in performing a method of the invention, can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A tetracycline (tet) inducible promoter can be particularly useful for driving expression of a polynucleotide of the invention, for example, a polynucleotide encoding a dominant negative form of myostatin, in which the proteolytic processing site has been mutated, or encoding a myostatin prodomain, which can form a complex with a mature myostatin peptide, or encoding a dominant negative form of a GDF receptor. Upon administration of tetracycline, or a tetracycline analog, to a subject containing a polynucleotide operatively linked to a tet inducible promoter, expression of the encoded peptide is induced, whereby the peptide can effect its activity, for example, whereby a peptide agent can reduce or inhibit myostatin signal transduction. Such a method can be used, for example, to induce muscle hypertrophy in an adult organism.

The polynucleotide also can be operatively linked to tissue specific regulatory element, for example, a muscle cell specific regulatory element, such that expression of an encoded peptide is restricted to the muscle cells in an individual, or to muscle cells in a mixed population of cells in culture, for example, an organ culture. Muscle cell specific regulatory elements including, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci. USA* 88:5847-5851, 1991, which is incorporated herein by reference) are well known in the art.

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a myostatin prodomain or functional peptide portion thereof can be cloned into a baculovirus vector, which then can be used to infect an insect host cell, thereby providing a means to produce large amounts of the encoded prodomain. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

The present invention also provides antibodies that specifically bind a peptide portion of a promyostatin polypeptide or a mutant promyostatin polypeptide. Particularly useful antibodies of the invention include antibodies that specifically bind a myostatin prodomain, or a functional peptide portion thereof, and antibodies that bind a promyostatin polypeptide and reduce or inhibit proteolytic cleavage of the promyostatin to a mature myostatin peptide. In addition, an antibody of the invention can be an antibody that specifically binds a GDF receptor, or functional peptide portion thereof, as described below. Methods of preparing and isolating an antibody of the invention are described in greater detail below, the disclosure of which is incorporated herein by reference.

Myostatin is essential for proper regulation of skeletal muscle mass. As compared to wild type mice, myostatin knock-out mice, which lack myostatin, have two to three times the amount of muscle due to a combination of hyperplasia and hypertrophy. As disclosed herein, myostatin knock-out mice also have a dramatic reduction in fat accumulation due, at least in part, to an increased anabolic state of skeletal muscle tissue throughout the body. Conversely, over-expression of myostatin in nude mice induced a wasting syndrome that resembles the cachectic state observed in human patients suffering from chronic diseases such as cancer or AIDS. As further disclosed herein, myostatin activity can be mediated through a signal transduction having the characteristics of the Smad signal transduction pathway. Accordingly, the invention provides methods of modulating an effect of myostatin on a cell by contacting the cell with an agent that affects myostatin signal transduction in the cell.

As used herein, the term "modulate," when used in reference to an effect of myostatin on a cell, means that myostatin signal transduction in the cell either is increased or is reduced or inhibited. The terms "increase" and "reduce or inhibit" are used in reference to a baseline level of myostatin signal transduction activity, which can be the level of activity of the signal transduction pathway in the absence of myostatin, or the level of activity in a normal cell in the presence of myostatin. For example, the myostatin signal transduction pathway exhibits a particular activity in a muscle cell contacted with myostatin, and, upon further contacting the muscle cell with a myostatin prodomain, myostatin signal transduction activity can be reduced or inhibited. As such, a myostatin prodomain is an agent useful for reducing or inhibiting myostatin signal transduction. Similarly, a prodomain of another GDF family member such as a GDF-11 prodomain, or of another TGF-β family member such as an activin prodomain, MIS prodomain, or the like, can be useful for reducing myostatin signal transduction. The terms "reduce or inhibit" are used together herein because it is recognized that, in some cases, the level of myostatin signal transduction can be reduced below a level that can be detected by a particular assay. As such, it may not be determinable using such an assay as to whether a low level of myostatin signal transduction remains, or whether the signal transduction is completely inhibited.

As used herein, the term "myostatin signal transduction" refers to the series of events, generally a series of protein-protein interactions, that occurs in a cell due to the specific interaction of myostatin with a myostatin receptor expressed on the surface of the cell. As such, myostatin signal transduction can be detected, for example, by detecting a specific interaction of myostatin with its receptor on a cell, by detecting phosphorylation of one or more polypeptides involved in a myostatin signal transduction pathway in the cell, by detecting expression of one or more genes that are specifically induced due to myostatin signal transduction, or by detecting a phenotypic change that occurs in response to myostatin signal transduction (see Examples). As disclosed herein, an agent useful in a method of the invention can act as an agonist to stimulate myostatin signal transduction or as an antagonist to reduce or inhibit myostatin signal transduction.

The methods of the present invention are exemplified generally herein with respect to myostatin. It should be recognized, however, that the methods of the invention can more broadly encompass modulating an effect of other GDF peptides, for example, GDF-11, on a cell by contacting the cell with an agent that affects signal transduction due to the GDF in the cell. Methods of practicing the full scope of the invention will be readily known in view of the present disclosure, which includes, for example, methods for identifying GDF receptors, methods for identifying agents that modulate signal transduction due to a specific interaction of the GDF with its receptor, and the like.

A myostatin signal transduction pathway is exemplified herein by the Smad pathway, which is initiated upon myostatin specifically interacting with the extracellular domain of an activin type II receptor and propagated through interactions of intracellular polypeptides, including Smad proteins, in the cell. In general, myostatin signal transduction is associated with phosphorylation or dephosphorylation of specific intracellular polypeptides such as Smad polypeptides. Thus, myostatin signal transduction in a cell can be detected by detecting an increased level of phosphorylation of one or more Smad polypeptides in the presence of myostatin as compared to the level of phosphorylation of the polypeptides in the absence of myostatin. A method of the invention provides a means to increase or decrease myostatin signal transduction and, therefore, the level of phosphorylation of an Smad polypeptide involved in a myostatin signal transduction pathway will be increased above a normal level or decreased below a level expected in the presence of myostatin, respectively.

A method of the invention can be performed, for example, by contacting under suitable conditions a target cell and an agent that affects myostatin signal transduction in the cell. Suitable conditions can be provided by placing the cell, which can be an isolated cell or can be a component of a tissue or organ, in an appropriate culture medium, or by contacting the cell in situ in an organism. For example, a medium containing the cell can be contacted with an agent the affects the ability of myostatin to specifically interact with a myostatin receptor expressed on the cell, or with an agent that affects a myostatin signal transduction pathway in the cell. In general, the cell is a component of a tissue or organ in a subject, in which case contacting the cell can comprise administering the agent to the subject. However, the cell also can be manipulated in culture, then can be maintained in culture, administered to a subject, or used to produce a transgenic nonhuman animal.

An agent useful in a method of the invention can be any type of molecule, for example, a polynucleotide, a peptide, a peptidomimetic, peptoids such as vinylogous peptoids, a small organic molecule, or the like, and can act in any of various ways to affect myostatin signal transduction. The agent can act extracellularly by binding myostatin or a myostatin receptor such as an activin receptor, thereby altering the ability of myostatin to specifically interact with its receptor, or can act intracellularly to alter myostatin signal transduction in the cell. In addition, the agent can be an agonist, which mimics or enhances the effect of myostatin on a cell, for example, the ability of myostatin to specifically interact with its receptor, thereby increasing myostatin signal transduction in the cell; or can be an antagonist, which can reduces or inhibits the effect of myostatin on a cell, thereby reducing or inhibiting myostatin signal transduction in the cell.

As used herein, the term "specific interaction" or "specifically binds" or the like means that two molecules form a complex that is relatively stable under physiologic conditions. The term is used herein in reference to various interactions, including, for example, the interaction of myostatin and a myostatin receptor, the interaction of the intracellular components of a myostatin signal transduction pathway, the interaction of an antibody and its antigen, and the interaction of a myostatin prodomain with myostatin. A specific interaction can be characterized by a dissociation constant of at least about $1 \times 116$ M, generally at least about $1 \times 10^{-7}$ M, usually at least about $1 \times 10^{-8}$ M, and particularly at least about $1 \times 10^{-9}$ M or $1 \times 10^{-10}$ M or greater. A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. In addition, a specific interaction such as the extracellular interaction of a myostatin prodomain and myostatin generally is stable under conditions such as those used for aquaculture of a commercially valuable marine organism. Methods for determining whether two molecules interact specifically are well known and include, for example, equilibrium dialysis, surface plasmon resonance, and the like.

An agent that alters a specific interaction of myostatin with its receptor can act, for example, by binding to myostatin such that it cannot interact specifically with its cellular receptor, by competing with myostatin for binding to its receptor, or by otherwise by-passing the requirement that myostatin specifically interact with its receptor in order to induce myostatin signal transduction. A truncated myostatin receptor such as a soluble extracellular domain of a myostatin receptor is an example of an agent that can bind myostatin, thereby sequestering myostatin and reducing or inhibiting its ability to interact specifically with a cell surface myostatin receptor. A myostatin prodomain or functional peptide portion thereof is another example of an agent that can bind myostatin, thereby reducing or inhibiting the ability of the myostatin to interact specifically with a cell surface myostatin receptor. Such myostatin antagonists are useful in practicing a method of the invention, particularly for reducing or inhibiting myostatin signal transduction in a cell.

Follistatin is another example of an agent that can bind to myostatin, thereby reducing or inhibiting the ability of myostatin to interact specifically with its receptor. Follistatin can bind to and inhibit the activity of various TGF-β family members, including myostatin (GDF-8; U.S. Pat. No. 6,004,937) and GDF-11 (Gamer et al., *Devel. Biol.* 208:222-232, 1999) and, therefore, can be used for performing a method as disclosed. Although the use of follistatin for modulating the effects of myostatin previously has been described (U.S. Pat. No. 6,004,937), it was not known, prior to the present disclosure, that follistatin reduces or inhibits the ability of myostatin to interact specifically with a myostatin receptor such as Act RIIB.

An agent useful in a method of the invention also can interact with a cellular myostatin receptor, thereby competing with myostatin for the receptor. Such an agent can be, for example, an antibody that specifically binds a cell surface myostatin receptor, including all or a portion of the myostatin binding domain, thereby preventing myostatin from interacting specifically with the receptor. Such an anti-myostatin receptor antibody can be selected for its ability to specifically bind the receptor without activating myostatin signal transduction and, therefore, can be useful as a myostatin antagonist for reducing or inhibiting myostatin signal transduction; or can be selected for its ability to specifically bind the receptor and activate myostatin signal transduction, thus acting as a myostatin agonist. The antibody can be raised using a myostatin receptor, or the extracellular domain of the receptor, as an immunogen, or can be an anti-idiotype antibody, which is raised against an anti-myostatin antibody and mimics myostatin. Anti-GDF receptor antibodies are discussed in greater detail below.

An agent useful in a method of the invention also can be an agent that reduces or inhibits proteolytic cleavage of a pro-GDF polypeptide to an active mature GDF peptide, thereby reducing or inhibiting GDF signal transduction. Such an agent can be a protease inhibitor, particularly one that inhibits the activity of a protease that recognizes and cleaves an Arg-Xaa-Xaa-Arg (SEQ ID NO: 21) proteolytic recognition site. Where the pro-GDF is promyostatin, an anti-myostatin antibody that reduces or inhibits the specific binding of a protease to the Arg-Xaa-Xaa-Arg (SEQ ID NO: 21) proteolytic cleavage site in myostatin also can be used reduce or inhibit proteolysis of promyostatin, thereby reducing the amount of mature myostatin produced. Such an antibody can bind the proteolytic cleavage site, or can bind some other site on the pro-GDF polypeptide such that binding of and cleavage by the protease is reduced or inhibited.

In addition, an agent useful in a method of the invention can be a mutant myostatin receptor, which, for example, lacks myostatin signal transduction activity in response to myostatin binding, or has constitutive myostatin signal transduction activity. For example, a mutant myostatin receptor can have a point mutation, a deletion, or the like in its kinase domain such that the receptor lacks kinase activity. Such a dominant negative mutant myostatin receptor lacks the ability to transmit myostatin signal transduction despite the fact that it can specifically bind myostatin.

An agent useful in a method of the invention also can modulate the level or activity of an intracellular polypeptide involved in a myostatin signal transduction pathway. As disclosed herein, regulation of muscle growth by myostatin can involve components of a signal transduction pathway that is activated by activin type II receptors (see Examples 7 and 9; see, also, Example 14). Myostatin specifically interacts with activin type IIB receptors (Act RIIB) expressed in COS cells in culture (Example 7). The low affinity of binding indicates that myostatin binding to Act RIIB in vivo may involve other factors, similar to TGF-β, which has significantly higher affinity for the type II receptor when the type I receptor also is present (Attisano et al., *Cell* 75:671-680, 1993), or to other systems that require other molecules for presenting the ligand to the signaling receptor (Massague, supra, 1998; Wang et al., *Cell* 67:795-805, 1991).

The specific interaction of myostatin with Act RIIB indicates that myostatin signal transduction can involve components of the Smad signal transduction pathway. Thus, the Smad signal transduction pathway provides a target for modulating the effect of myostatin on a cell, and agents that affect the Smad pathway can be useful for modulating myostatin signal transduction in a cell.

Agents useful for modulating the level or activity of intracellular polypeptide components of a GDF signal transduction include agonists, which can increase signal transduction activity, and antagonists, which can reduce or inhibit signal transduction activity. With respect to myostatin, for example, agents that can increase myostatin signal transduction activity are exemplified by phosphatase inhibitors, which can reduce or inhibit dephosphorylation of Smad polypeptides, thereby prolonging the signal transducing activity of the Smad. Dominant negative Smad 6 or Smad 7 polypeptides, which can negate the inhibitory effect of Smad 6 and Smad 7 on myostatin signal transduction, are additional examples of agents that can increase myostatin signal transduction activity by increasing Smad signal transduction.

Antagonist agents that can reduce or inhibit myostatin signal transduction activity are exemplified by dominant negative Smad polypeptides such as dominant negative Smad 2, Smad 3 or Smad 4, in which the C-terminal phosphorylation sites have been mutated. The inhibitory Smad polypeptides such as Smad 6 and Smad 7, which inhibit the activation of Smad 2 and Smad 3; and a c-ski polypeptide, which binds Smad polypeptides and inhibits signal transduction, are additional examples of antagonists useful for reducing or inhibiting myostatin signal transduction by decreasing Smad signal transduction.

Where the agent that acts intracellularly is a peptide, it can be contacted with the cell directly, or a polynucleotide encoding the peptide (or polypeptide) can be introduced into the cell and the peptide can be expressed in the cell. It is recognized that some of the peptides useful in a method of the invention are relatively large and, therefore, may not readily traverse a cell membrane. However, various methods are known for introducing a peptide into a cell. The selection of a method for introducing such a peptide into a cell will depend, in part, on the characteristics of the target cell, into which the polypeptide is to be provided. For example, where the target cells, or a few cell types including the target cells, express a receptor, which, upon binding a particular ligand, is internalized into the cell, the peptide agent can be operatively associated with the ligand. Upon binding to the receptor, the peptide is translocated into the cell by receptor-mediated endocytosis. The peptide agent also can be encapsulated in a liposome or formulated in a lipid complex, which can facilitate entry of the peptide into the cell, and can be further modified to express a receptor (or ligand), as above. The peptide agent also can be introduced into a cell by engineering the peptide to contain a protein transduction domain such as the human immunodeficiency virus TAT protein transduction domain, which facilitates translocation of the peptide into the cell (see Schwarze et al., *Science* 285:1569-1572 (1999), which is incorporated herein by reference; see, also, Derossi et al., *J. Biol. Chem.* 271: 18188 (1996)).

The target cell also can be contacted with a polynucleotide encoding the peptide agent, which can be expressed in the cell. The expressed peptide agent can be a mutant GDF receptor or peptide portion thereof. Example of a mutant GDF receptor include a kinase-deficient form of a myostatin receptor such as a dominant negative Act RIIA or Act RIIB, which can, but need not, have the ability to specifically bind a ligand (e.g., myostatin); and a truncated myostatin or other GDF receptor, such as a soluble form of a myostatin receptor, which binds myostatin, thereby sequestering it from interacting specifically with a cellular myostatin receptor; a dominant-negative form of a Smad polypeptide such as a dominant negative Smad 3, in which the C-terminal phosphorylation sites have been mutated (Liu et al., *Proc. Natl. Acad. Sci., USA* 94:10669-10674, 1997); a Smad 7 polypeptide, which inhibits the activation of Smad 2 and Smad 3 (Heldin et al., *Nature* 390:465-471, 1997); or a c-ski polypeptide, which can bind a Smad polypeptide and inhibit signal transduction by the Smad (Suprave et al., *Genes Devel.* 4:1462-1472, 1990).

Expression of a c-ski peptide agent in a cell can be particularly useful for modulating myostatin signal transduction. Mice lacking c-ski show a severe reduction in skeletal muscle mass (Berk et al., *Genes Devel.* 11:2029-2039, 1997), whereas transgenic mice that overexpress c-ski in muscle show dramatic muscle hypertrophy (Suprave et al., supra, 1990). c-ski interacts with and blocks the activity of certain Smad proteins, including Smad 2, Smad 3 and Smad 4, which mediate signaling of TGF-β and activin type II receptors (Luo et al., *Genes Devel.* 13:2196-1106, 1999; Stroschein et al., *Science* 286:771-774, 1999; Sun et al., *Mol. Cell.* 4:499-509, 1999a; Sun et al., *Proc. Natl. Acad. Sci. USA* 96:112442-12447, 1999b; Akiyoshi et al., *J. Biol. Chem.* 274: 35269, 1999). Thus, in view of the present disclosure that myostatin activity can be mediated through Act RIIB binding, it will be recognized that the activity of myostatin, or of any GDF that utilizes an Smad pathway, can be modulated by increasing or decreasing c-ski expression in a target cell.

An agent useful in a method of the invention can be a polynucleotide, which can be contacted with or introduced into a cell as described above. Generally, but not necessarily, the polynucleotide is introduced into the cell, where it effects its function either directly, or following transcription or translation or both. For example, as discussed above, the polynucleotide can encode a peptide agent, which is expressed in the cell and modulates myostatin activity. Such an expressed peptide can be, for example, a mutant promyostatin polypeptide, which cannot be cleaved into active myostatin; or can be a mutant myostatin receptor, for example, a truncated myostatin receptor extracellular domain; a myostatin receptor extracellular domain operatively associated with a membrane anchoring domain; or a mutant myostatin receptor lacking protein kinase activity. Methods for introducing a polynucleotide into a cell are exemplified below or otherwise known in the art.

A polynucleotide agent useful in a method of the invention also can be, or can encode, an antisense molecule, a ribozyme or a triplexing agent. For example, the polynucleotide can be (or can encode) an antisense nucleotide sequence such as an antisense c-ski nucleotide sequence, which can act as an agonist to increase myostatin signal transduction in a cell; or an antisense Smad nucleotide sequence, which can act either as an agonist to increase myostatin signal transduction or as antagonist to reduce or inhibit myostatin signal transduction, depending on the particular Smad antisense nucleotide sequence. Such polynucleotides can be contacted directly with a target cell and, upon uptake by the cell, can effect their antisense, ribozyme or triplexing activity; or can be encoded by a polynucleotide that is introduced into a cell, whereupon the polynucleotide is expressed to produce, for example, an antisense RNA molecule or ribozyme, which effects its activity.

An antisense polynucleotide, ribozyme or triplexing agent is complementary to a target sequence, which can be a DNA or RNA sequence, for example, messenger RNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of 20 nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., supra, 1989) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A polynucleotide useful as an antisense molecule, a ribozyme or a triplexing agent can inhibit translation or cleave the nucleic acid molecule, thereby modulating myostatin signal transduction in a cell. An antisense molecule, for example, can bind to an mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a polynucleotide introduced into the target cell. Specific nucleotide sequences useful as antisense molecules can be identified using well known methods, for example, gene walking methods (see, for example, Seimiya et al., *J. Biol. Chem.* 272:4631-4636 (1997), which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., *Antisense Res. Devel.* 1:227 (1991); Helene, *Anticancer Drug Design* 6:569 (1991)). Thus, a triplexing agent can be designed to recognize, for example, a sequence of a Smad gene regulatory element, thereby reducing or inhibiting the expression of a Smad polypeptide in the cell, thereby modulating myostatin signal transduction in a target cell.

The present invention also provides a method of identifying an agent that can alter the effect of a GDF such myostatin on a cell, particularly agents that can alter the ability of the GDF to interact specifically with its cellular receptor. Such agents can act by increasing or decreasing the ability of the GDF to interact specifically with its receptor and, therefore, are useful for increasing or decreasing GDF signal transduction, respectively. A screening method of the invention is exemplified herein using a myostatin receptor, for example, an activin type II receptor such as Act RIIA or Act RIIB.

A screening method of the invention can be performed, for example, by contacting under suitable conditions myostatin, or a functional peptide portion thereof, a myostatin receptor such as Act RIIA or Act RIIB, and an agent to be tested. The myostatin, the receptor and the agent can be contacted in any order as desired. As such, the screening method can be used to identify agents that can competitively or non-competitively inhibit myostatin binding to the receptor, agents that can mediate or enhance myostatin binding to the receptor, agents that can induce dissociation of specifically bound myostatin from the receptor, and agents that otherwise affect the ability of myostatin to induce signal transduction, such agents having agonist or antagonist activity. Appropriate control reactions are performed to confirm that the action of the agent is specific with respect to the myostatin or other GDF receptor.

Suitable conditions for performing a screening method of the invention can be any conditions that allow myostatin to specifically interact with its receptor, including methods as disclosed herein (see Examples 7 and 9) or otherwise known in the art. Thus, suitable conditions for performing the screening assay can be, for example, in vitro conditions using a substantially purified myostatin receptor; cell culture conditions, utilizing a cell that normally expresses a myostatin receptor, for example, an adipocyte or a muscle cell, or a cell that has been genetically modified to express a functional myostatin receptor on its surface; or in situ conditions as occur in an organism.

A screening method of the invention also can be performed using the methods of molecular modeling as described above. The utilization of a molecular modeling method provides a convenient, cost effective means to identify those agents, among a large population such as a combinatorial library of potential agents, that are most likely to interact specifically with a GDF receptor, thereby reducing the number of potential agents that need to be screened using a biological assay. Upon identifying agents that interact specifically with a GDF receptor such as Act RIIB using a molecular modeling method, the selected agents can be examined for the ability to modulate an effect of a GDF such as myostatin on a cell using the methods disclosed herein.

The ability of a test agent to modulate an effect of myostatin can be detected using methods as disclosed herein (see Examples 7 and 9) or otherwise known in the art. The term "test agent" or "test molecule" is used broadly herein to mean any agent that is being examined for agonist or antagonist activity in a method of the invention. Although the method generally is used as a screening assay to identify previously unknown molecules that can act as agonist or antagonist agents as described herein, the methods also can be used to confirm that a agent known to have a particular activity in fact has the activity, for example, in standardizing the activity of the agent.

A method of the invention can be performed, for example, by contacting myostatin with a cell that has been genetically modified to express an Act RIIB receptor, and determining the effect of an agent, for example, a dominant negative Act RIIB, by examining phosphorylation of a Smad polypeptide involved in the myostatin signal transduction pathway. If desired, the cell can be further genetically modified to contain a reporter nucleotide sequence, the expression of which is dependent on the myostatin signal transduction pathway, for example, on activation of the Smad pathway, and the effect of the test agent can be determined by comparing expression of the reporter nucleotide sequence in the presence and absence of the agent, the myostatin, or both. Expression of the reporter nucleotide sequence can be detected, for example, by detecting an RNA transcript of the reporter nucleotide sequence, or by detecting a polypeptide encoded by the reporter nucleotide sequence. A polypeptide reporter can be, for example, a β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase or xanthine guanine phosphoribosyltransferase polypeptide or the like, and can be detected, for example, by detecting radioactivity, luminescence, chemiluminescence, fluorescence, enzymatic activity, or specific binding due to the reporter polypeptide.

A screening method of the invention provides the advantage that it can be adapted to high throughput analysis and, therefore, can be used to screen combinatorial libraries of test agents in order to identify those agents that can modulate an effect of myostatin on a cell, including those agents that can alter a specific interaction of myostatin and a myostatin receptor. Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83-92, 1995; a nucleic acid library (O'Connell et al., supra, 1996; Tuerk and Gold, supra, 1990; Gold et al., supra, 1995; each of which is incorporated herein by reference); an oligosaccharide library (York et al., *Carb. Res.*, 285:99-128, 1996; Liang et al., *Science*, 274:1520-1522, 1996; Ding et al., *Adv. Expt. Med. Biol.*, 376:261-269, 1995; each of which is incorporated herein by reference); a lipoprotein library (de Kruif et al., *FEBS Lett.*, 399:232-236, 1996, which is incorporated herein by reference); a glycoprotein or glycolipid library (Karaoglu et al., *J. Cell Biol.*, 130:567-577, 1995, which is incorporated herein by reference); or a chemical library containing, for example, drugs or other pharmaceutical agents (Gordon et al., *J. Med. Chem.*, 37:1385-1401, 1994; Ecker and Crooke, *Bio/Technology*, 13:351-360, 1995; each of which is incorporated herein by reference). Polynucleotides can be particularly useful as agents that can modulate a specific interaction of myostatin and its receptor because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

In view of the present disclosure, it will be recognized that various animal model systems can be used as research tools to identify agents useful for practicing a method of the invention. For example, transgenic mice or other experimental animals can be prepared using the various myostatin inhibitor constructs disclosed herein, and the transgenic non-human organism can be examined directly to determine the effect produced by expressing various levels of a particular agent in the organism. In addition, the transgenic organism, for example, a transgenic mouse, can be crossbred with other mice, for example, with ob/ob, db/db, or agouti lethal yellow mutant mice, to determine optimal levels of expression of a myostatin inhibitor useful for treating or preventing a disorder such as obesity, type II diabetes, or the like. As such, the present invention provides transgenic non-human organisms, particularly transgenic organisms containing a polynucleotide encoding a myostatin prodomain, which can include the myostatin signal peptide, or a polynucleotide encoding a mutant promyostatin polypeptide.

Various methods are known for producing a transgenic animal. In one method, an embryo at the pronuclear stage (a "one cell embryo") is harvested from a female and the transgene is microinjected into the embryo, in which case the transgene will be chromosomally integrated into the germ cells and somatic cells of the resulting mature animal. In another method, embryonic stem cells are isolated and the transgene is incorporated into the stem cells by electroporation, plasmid transfection or microinjection; the stem cells are then reintroduced into the embryo, where they colonize and contribute to the germ line. Methods for microinjection of polynucleotides into mammalian species are described, for example, in U.S. Pat. No. 4,873,191, which is incorporated herein by reference. In yet another method, embryonic cells are infected with a retrovirus containing the transgene, whereby the germ cells of the embryo have the transgene chromosomally integrated therein.

When the animals to be made transgenic are avian, microinjection into the pronucleus of the fertilized egg is problematic because avian fertilized ova generally go through cell division for the first twenty hours in the oviduct and, therefore, the pronucleus is inaccessible. Thus, the retrovirus infection method is preferred for making transgenic avian species (see U.S. Pat. No. 5,162,215, which is incorporated herein by reference). If microinjection is to be used with avian species, however, the embryo can be obtained from a sacrificed hen approximately 2.5 hours after the laying of the previous laid egg, the transgene is microinjected into the cytoplasm of the germinal disc and the embryo is cultured in a host shell until maturity (Love et al., *Biotechnology* 12, 1994). When the animals to be made transgenic are bovine or porcine, microinjection can be hampered by the opacity of the ova, thereby making the nuclei difficult to identify by traditional differential interference-contrast microscopy. To overcome this problem, the ova first can be centrifuged to segregate the pronuclei for better visualization.

Non-human transgenic animals of the invention can be bovine, porcine, ovine, avian or other animals. The transgene can be introduced into embryonal target cells at various developmental stages, and different methods are selected depending on the stage of development of the embryonal target cell. The zygote is the best target for microinjection. The use of zygotes as a target for gene transfer has a major advantage in that the injected DNA can incorporate into the host gene before the first cleavage (Brinster et al., *Proc. Natl. Acad. Sci. USA* 82:4438-4442, 1985). As a consequence, all cells of the transgenic non-human animal carry the incorporated transgene, thus contributing to efficient transmission of the transgene to offspring of the founder, since 50% of the germ cells will harbor the transgene.

A transgenic animal can be produced by crossbreeding two chimeric animals, each of which includes exogenous genetic material within cells used in reproduction. Twenty-five percent of the resulting offspring will be transgenic animals that are homozygous for the exogenous genetic material, 50% of the resulting animals will be heterozygous, and the remaining 25% will lack the exogenous genetic material and have a wild type phenotype.

In the microinjection method, the transgene is digested and purified free from any vector DNA, for example, by gel electrophoresis. The transgene can include an operatively associated promoter, which interacts with cellular proteins involved in transcription, and provides for constitutive expression, tissue specific expression, developmental stage specific expression, or the like. Such promoters include those from cytomegalovirus (CMV), Moloney leukemia virus (MLV), and herpes virus, as well as those from the genes encoding metallothionein, skeletal actin, Phosphenolpyruvate carboxylase (PEPCK), phosphoglycerate (PGK), dihydrofolate reductase (DHFR), and thymidine kinase (TK). Promoters from viral long terminal repeats (LTRs) such as Rous sarcoma virus LTR also can be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements, including, for example, enhancer elements to stimulate transcription, splice acceptors, termination and polyadenylation signals, ribosome binding sites to permit translation, and the like.

In the retroviral infection method, the developing non-human embryo can be cultured in vitro to the blastocyst stage. During this time, the blastomeres can be targets for retroviral infection (Jaenich, *Proc. Natl. Acad. Sci. USA* 73:1260-1264, 1976). Efficient infection of the blastomeres is obtained by enzymatic treatment to remove the zona pellucida (Hogan et al., *Manipulating the Mouse Embryo* (Cold Spring Harbor Laboratory Press, 1986). The viral vector system used to introduce the transgene is typically a replication-defective retrovirus carrying the transgene (Jahner et al., *Proc. Natl. Acad. Sci., USA* 82:6927-6931, 1985; Van der Putten et al., *Proc. Natl. Acad. Sci. USA* 82:6148-6152, 1985). Transfection is easily and efficiently obtained by culturing the blastomeres on a monolayer of virus producing cells (Van der Putten et al., supra, 1985; Stewart et al., *EMBO J.* 6:383-388, 1987). Alternatively, infection can be performed at a later stage. Virus or virus-producing cells can be injected into the blastocoele (Jahner et al., *Nature* 298:623-628, 1982). Most of the founders will be mosaic for the transgene since incorporation occurs only in a subset of the cells which formed the transgenic nonhuman animal. Further, the founder can contain various retroviral insertions of the transgene at different positions in the genome, which generally will segregate in the offspring. In addition, it is also possible to introduce transgenes into the germ line, albeit with low efficiency, by intrauterine retroviral infection of the mid-gestation embryo (Jahner et al., supra, 1982).

Embryonal stem cell (ES) also can be targeted for introduction of the transgene. ES cells are obtained from pre-implantation embryos cultured in vitro and fused with embryos (Evans et al. *Nature* 292:154-156, 1981; Bradley et al., *Nature* 309:255-258, 1984; Gossler et al., *Proc. Natl. Acad. Sci., USA* 83:9065-9069, 1986; Robertson et al., *Nature* 322:445-448, 1986). Transgenes can be efficiently introduced into the ES cells by DNA transfection or by retrovirus mediated transduction. Such transformed ES cells can thereafter be combined with blastocysts from a nonhuman animal. The ES cells thereafter colonize the embryo and contribute to the germ line of the resulting chimeric animal (see Jaenisch, *Science* 240:1468-1474, 1988).

As disclosed herein, myostatin can exert its activity, at least in part, through the Smad signal transduction pathway, and myostatin expression can be associated with various pathological conditions. As such, the present invention provides new targets for the treatment of various pathological conditions associated with myostatin, including metabolic conditions such as obesity and type II diabetes. Accordingly, the present invention provides methods for ameliorating the severity of a pathological condition in a subject, wherein the pathologic condition is characterized at least in part by an abnormal amount, development or metabolic activity of muscle or adipose tissue, by modulating myostatin signal transduction in a muscle cell or adipose tissue cell in the subject.

Myostatin functions as a negative regulator of muscle growth (McPherron et al., supra, 1997). Myostatin knock-out mice weighed approximately 25% to 30% more than wild type littermates, and this increase in body weight in the mice examined resulted entirely from a dramatic increase in skeletal muscle tissue weight. In mice lacking myostatin, the skeletal muscles weighed about 2 to 3 times as much as the corresponding muscles of wild type littermates. This increased muscle weight in the homozygous knock-out mice resulted from a combination of hyperplasia and hypertrophy.

As disclosed herein, heterozygous myostatin knock-out mice also have increased skeletal muscle mass, although to a lesser extent than that observed in homozygous mutant mice, thus demonstrating that myostatin acts in a dose-dependent manner in vivo (see Example 1). Furthermore, overexpression of myostatin in animals had the opposite effect with respect to muscle growth. For example, nude mice carrying myostatin-expressing tumors developed a wasting syndrome characterized by a dramatic loss of muscle and fat weight (see Example 8). This syndrome in the nude mice resembled the cachectic state that occurs in patients with chronic diseases such as cancer or AIDS.

The serum levels of myostatin immunoreactive material have been correlated with the status of patients with respect to muscle wasting (Gonzalez-Kadavid et al., *Proc. Natl. Acad. Med., USA* 95:14938-14943, 1998, which is incorporated herein by reference). Thus, patients with AIDS, who also showed signs of cachexia as measured by loss of total body weight, had slightly increased serum levels of myostatin immunoreactive material compared to either normal males without AIDS or to AIDS patients that did not have weight loss. However, the interpretation of these results was complicated because the myostatin immunoreactive material detected in the serum samples did not have the mobility on SDS gels that was expected for authentic processed myostatin.

As disclosed herein, myostatin not only affects muscle mass, but also affects the overall metabolism of an organism. For example, myostatin is expressed in adipose tissue, and myostatin deficient mice have a dramatic reduction in fat accumulation as the animals age (see Examples II and III). Although no mechanism for myostatin action is proposed herein, the effect of myostatin can be direct effect of myostatin on adipose tissue, or can be an indirect effect caused by the lack of myostatin activity on skeletal muscle tissue. Regardless of the mechanism, the overall anabolic effect on muscle tissue that results in response to decreased myostatin activity can alter the overall metabolism of the organism and affect the storage of energy in the form of fat, as demonstrated by the introduction of a myostatin mutation into an obese mouse strain (agouti lethal yellow ($A^Y$) mice), which suppressed fat accumulation by five-fold (see Example 5). Abnormal glucose metabolism also was partially suppressed in agouti mice containing the myostatin mutation. These results demonstrate that methods that inhibition of myostatin can be used to treat or prevent metabolic diseases such as obesity and type II diabetes.

The methods of the invention are useful, for example, for ameliorating the severity of various pathologic conditions, including, for example, the cachexia associated with chronic diseases such as cancer (see Norton et al., *Crit. Rev. Oncol. Hematol.* 7:289-327, 1987), as well as conditions such as type II diabetes, obesity, and other metabolic disorders. As used herein, the term "pathologic condition" refers to a disorder that is characterized, at least in part, by an abnormal amount, development or metabolic activity of muscle or adipose tissue. Such pathologic conditions, which include, for example, obesity; conditions associated with obesity, for example, atherosclerosis, hypertension, and myocardial infarction; muscle wasting disorders such as muscular dystrophy, neuromuscular diseases, cachexia, and anorexia; and metabolic disorders such as type II diabetes, which generally, but not necessarily, is associated with obesity, are particularly amenable to treatment using a method of the invention.

As used herein, the term "abnormal," when used in reference to the amount, development or metabolic activity of muscle or adipose tissue, is used in a relative sense in comparison to an amount, development or metabolic activity that a skilled clinician or other relevant artisan would recognize as being normal or ideal. Such normal or ideal values are known to the clinician and are based on average values generally observed or desired in a healthy individual in a corresponding population. For example, the clinician would know that obesity is associated with a body weight that is about twenty percent above an "ideal" weight range for a person of a particular height and body type. However, the clinician would recognize that a body builder is not necessarily obese simply by virtue of having a body weight that is twenty percent or more above the weight expected for a person of the same height and body type in an otherwise corresponding population. Similarly, the artisan would know that a patient presenting with what appears to be abnormally decreased muscle activity could be identified as having abnormal muscle development, for example, by subjecting the patient to various strength tests and comparing the results with those expected for an average healthy individual in a corresponding population.

A method of the invention can ameliorate the severity of a pathologic condition that is characterized, at least in part, by an abnormal amount, development or metabolic activity in muscle or adipose tissue, by modulating myostatin signal transduction in a muscle or adipose tissue cell associated with the etiology of the condition. As used herein, the term "ameliorate," when used in reference to the severity of a pathologic condition, means that signs or symptoms associated with the condition are lessened. The signs or symptoms to be monitored will be characteristic of a particular pathologic condition and will be well known to skilled clinician, as will the methods for monitoring the signs and conditions. For example, where the pathologic condition is type II diabetes, the skilled clinician can monitor the glucose levels, glucose clearance rates, and the like in the subject. Where the pathologic condition is obesity or cachexia, the clinician can simply monitor the subject's body weight.

The agent to be administered to the subject is administered under conditions that facilitate contact of the agent with the target cell and, if appropriate, entry into the cell. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell (see Schwarze et al., supra, 1999; Derossi et al., supra, 1996).

The presence of the agent in the target cell can be identified directly, for example, by operatively linking a detectable label to the agent, by using an antibody specific for the agent, particularly a peptide agent, or by detecting a downstream effect due to the agent, for example, decreased phosphorylation of an Smad polypeptide in the cell. An agent can be labeled so as to be detectable using methods well known in the art (Hermanson, "Bioconjugate Techniques" (Academic Press 1996), which is incorporated herein by reference; see, also, Harlow and Lane, supra, 1988). For example, a peptide or polynucleotide agent can be labeled with various detectable moieties including a radiolabel, an enzyme such as alkaline phosphatase, biotin, a fluorochrome, and the like. Where the agent is contained in a kit, the reagents for labeling the agent also can be included in the kit, or the reagents can be purchased separately from a commercial source.

An agent useful in a method of the invention can be administered to the site of the pathologic condition, or can be administered by any method that provides the target cells with the polynucleotide or peptide. As used herein, the term "target cells" means muscle cells or adipocytes that are to be contacted with the agent. For administration to a living subject, the agent generally is formulated in a pharmaceutical composition suitable for administration to the subject. Thus, the invention provides pharmaceutical compositions containing an agent, which is useful for modulating myostatin signal transduction in a cell, in a pharmaceutically acceptable carrier. As such, the agents are useful as medicaments for treating a subject suffering from a pathological condition as defined herein.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition useful for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of a pharmaceutical composition containing an agent that alters myostatin signal transduction will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a peptide agent can be prepared using D-amino acids, or can contain one or more domains based on peptidomimetics, which are organic molecules that mimic the structure of peptide domain; or based on a peptoid such as a vinylogous peptoid.

A pharmaceutical composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The pharmaceutical composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The present invention also provides a method of modulating the growth of muscle tissue or adipose tissue in a subject. As disclosed herein, GDF receptors such as Act RIIA and Act RIIB are involved in mediating the effects of a GDF such as myostatin, which is involved in muscle tissue and adipose tissue formation. Thus, in one embodiment, a method of modulating the growth of muscle tissue or adipose tissue includes affecting signal transduction from a GDF receptor, such as an activin receptor, e.g., Act RIIA or Act RIIB. Such a method can be performed by contacting cells of the tissue, or expressing in the cells, a mutant GDF receptor, which has dominant negative activity, constitutive activity, or the like.

In another embodiment, a method of modulating the growth of muscle tissue or adipose tissue in an organism is performed by administering to the organism an agent that affects myostatin signal transduction. Preferably, the agent is or encodes a myostatin prodomain or a mutant promyostatin polypeptide, either of which can include a myostatin signal peptide. As used herein, the term "growth" is used in a relative sense in referring to the mass of muscle tissue or mass of adipose tissue in an organism that has been subjected to a method of the invention as compared to a corresponding organism that has not been subjected to a method of the invention. Thus, where a method of the invention is performed such that myostatin signal transduction has been reduced or inhibited, it will be recognized that the growth of muscle tissue in the organism would result in an increased muscle mass in the organism as compared to the muscle mass of a corresponding organism (or population of organisms) in which myostatin signal transduction had not been so effected.

A method of the invention can be useful for increasing the muscle mass or reducing the fat content of an organism or both. For example, where such a method is performed on an organism that is useful as a food source, the protein content of the food can be increased, the cholesterol level can be decreased, and the quality of the foodstuff can be improved. A method of the invention also can be useful for decreasing the growth of muscle tissue in an organism, for example, an organism that is detrimental to an environment, such that the organism is less able to compete in the environment. Thus, a method of the invention can be performed on any eukaryotic organism that expresses myostatin, including a vertebrate organism, for example, mammalian, avian or piscine organism, or can be an invertebrate organism, for example, a mollusk, echinoderm, gastropod or cephalopod.

The agent can be any agent that alters myostatin signal transduction, as disclosed herein, and can be administered to the organism in any convenient manner. For example, where the organism to be treated are fish, shrimp, scallops, or the like, which are grown in aquaculture, the agent can be added to the water in which the organisms are maintained or can be included in their food, particularly where the agent is a soluble peptide or a small organic molecule.

Where the agent used in a method of the invention is a polynucleotide that encodes a peptide agent, an antisense agent, or the like, germ cells of a non-human organism containing the polynucleotide can be selected and transgenic organisms expressing the agent can be produced. Preferably, the polynucleotide is under the control of an inducible regulatory element, such that the agent encoded by the polynucleotide can be expressed at a time and for a duration as desired. Accordingly, the present invention provides transgenic non-human organisms, as well as food products produced by these organisms. Such food products have increased nutritional value because of the increase in muscle tissue. The transgenic non-human animals can be any species as disclosed herein, including vertebrate organisms such as cattle, pigs, sheep, chicken, turkey and fish, and invertebrate species such as shrimp, lobster, crabs, squid, oysters and abalone.

The regulation of TGF-β family members and their specific interactions with cell surface receptors are beginning to be elucidated. Thus, coexpression of the prodomain of a TGF-β family member with a mature region of another member of the TGF-β family is associated with intracellular dimerization and secretion of biologically active homodimers occur (Gray et al., *Science* 247:1328, 1990). For example, use of the BMP-2 prodomain with the BMP-4 mature region led to dramatically improved expression of mature BMP-4 (Hammonds et al., (*Mol. Endocrinol.* 5:149, 1991). For most of the family members that have been studied, the homodimeric species are biologically active, whereas for other family members such as the inhibins (Ling et al., *Nature* 321:779, 1986) and the TGF-βs (Cheifetz et al., *Cell* 48:409, 1987), heterodimers also have been detected and appear to have different biological properties than the respective homodimers.

Receptor-ligand interaction studies have revealed a great deal of information as to how cells respond to external stimuli, and have led to the development of therapeutically important compounds such as erythropoietin, the colony stimulating factors, and PDGF. Thus, continual efforts have been made at identifying the receptors that mediate the action of the TGF-β family members. As disclosed herein, myostatin specifically interacts with an activin type II receptor. The identification of this interaction provides targets for identifying antagonists and agonists useful for agricultural and human therapeutic purposes, for example, for treating in various pathological conditions such as obesity, type II diabetes, and cachexia. The identification of this specific interaction also provides a means to identify other myostatin receptors, as well as the specific receptors of other growth differentiation factors. Accordingly, the present invention provides GDF receptors, which specifically interact with a GDF or combination of GDFs, for example, with myostatin, GDF-11, or both.

A GDF receptor of the invention is exemplified herein by a myostatin receptor, particularly an activin type II receptor, which specifically interacts with myostatin and with GDF-11. However, myostatin receptors that specifically interact with myostatin, but not GDF-11, also are encompassed within the present invention, as are GDF-11 receptors that specifically interact with GDF-11 but not myostatin, and the like. For convenience of discussion, the receptors of the invention are referred to herein generally as a "GDF receptor" and are exemplified by a myostatin receptor, which is a receptor that specifically interacts at least with myostatin. As such, while reference is made generally to a specific interaction of myostatin with a myostatin receptor, it will be recognized that the present disclosure more broadly encompasses any GDF receptor, including a GDF-11 receptor, which specifically interacts at least with GDF-11.

A recombinant cell line that expresses a GDF receptor polypeptide also is provided, as are antibodies that specifically bind the receptor, substantially purified polynucleotides that encode the receptor, and substantially purified GDF receptor polypeptides. Peptide portions of a GDF receptor also are provided, including, for example, soluble extracellular domains of a GDF receptor such as a myostatin receptor, which, as disclosed herein, can alter the specific interaction of myostatin with a cellular myostatin receptor; a constitutively active intracellular kinase domain of a GDF receptor, which can induce, stimulate or otherwise maintain GDF signal transduction in a cell; or other truncated portion of a GDF receptor having an ability to modulate myostatin or other GDF signal transduction.

The invention also provides methods for identifying a GDF receptor polypeptide, including methods of screening genomic or cDNA libraries, which can be expression libraries, using nucleotide probes or antibody probes; methods of screening cells that are responsive to and, therefore, express the receptor, using, for example, a GDF such as myostatin or a functional peptide portion thereof; two hybrid assays, as described above, using, for example, the GDF peptide as a component of one hybrid and peptides expressed from a cDNA library, which is prepared from cells expressing a receptor for the GDF, as components of the second hybrids, and the like.

As described above, agents that specifically interact with a GDF receptor, for example, a myostatin receptor such as Act RIIB can be identified by using the receptor to screen for such agents. Conversely, an agent that has been identified as having the ability to specifically interact with a myostatin receptor such as the Act RIIB receptor, can be used to screen for additional myostatin receptors or other GDF receptors. Such a method can include incubating components such as the agent (or myostatin or other GDF) and a cell expressing a GDF receptor, which can be a truncated membrane bound receptor or a soluble receptor, under conditions sufficient to allow the agent (or GDF) to interact specifically with the receptor; measuring the agent (or GDF) bound to the receptor; and isolating the receptor. A method of molecular modeling as described above also can be useful as a screening method for identifying a GDF receptor, or a functional peptide portion thereof.

Non-human transgenic animals that have a phenotype characterized by expression of a GDF receptor also are provided, the phenotype being conferred by a transgene contained in the somatic and germ cells of the animal. The transgene comprises a polynucleotide encoding the GDF receptor, for example, myostatin receptor, polypeptide. Methods of producing such transgenic animals are disclosed herein or otherwise known in the art.

The present invention provides a substantially purified polynucleotide encoding all or a peptide portion of a GDF receptor. Although a GDF receptor is exemplified herein by an activin type II receptor, polynucleotides encoding activin type II receptors previously have been described (U.S. Pat. No. 5,885,794). Thus, it should be recognized that such activin type II receptors are not encompassed within the present invention (Massague, supra, 1998; Heldin et al., supra, 1997). Similarly, activin type I receptors, including Act RIB; TGF-β receptors, including TGF-β RI and TGF-β R11; and BMP receptors, including BMP RIA, BMP RIB and BMP R11, have been described and are well known in the art (Massague, supra, 1998; Heldin et al., supra, 1997) and, therefore, are not encompassed within the GDF receptors of the invention.

A polynucleotide of the invention can encode a polypeptide having a myostatin receptor activity, for example, myostatin binding activity, or can encode a mutant myostatin receptor, for example, a mutant myostatin receptor having a mutation in a kinase domain, such that the mutant acts as a dominant negative myostatin receptor (see above). Thus, a polynucleotide of the invention can be a naturally occurring, synthetic, or intentionally manipulated polynucleotide. For example, portions of the mRNA sequence can be altered due to alternate RNA splicing patterns or the use of alternate promoters for RNA transcription. As another example, the polynucleotide can be subjected to site directed mutagenesis. The polynucleotide also can be antisense nucleotide sequence. GDF receptor polynucleotides of the invention include sequences that are degenerate as a result of the genetic code. There are 20 natural amino acids, most of which are specified by more than one codon. Therefore, all degenerate nucleotide sequences are included within the invention, provided the amino acid sequence of the GDF receptor polypeptide encoded by the polynucleotide is functionally unchanged. Also included are nucleotide sequences that encode myostatin receptor polypeptides.

Oligonucleotide portions of a polynucleotide encoding a GDF receptor of the invention also are encompassed within the present invention. Such oligonucleotides generally are at least about 15 bases in length, which is sufficient to permit the oligonucleotide to selectively hybridize to a polynucleotide encoding the receptor, and can be at least about 18 nucleotides or 21 nucleotides or more in length. As used herein, the term "selective hybridization" or "selectively hybridize" refers to hybridization under moderately stringent or highly stringent physiological conditions, which can distinguish related nucleotide sequences from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

A GDF receptor-encoding polynucleotide of the invention can be obtained by any of several methods. For example, the polynucleotide can be isolated using hybridization or computer based techniques, as are well known in the art. These methods include, but are not limited to, 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences (see above); 5) differential screening of a subtracted DNA library; and 6) two hybrid assays using, for example, a mature GDF peptide in one of the hybrids.

In view of the present disclosure that an activin receptor specifically interacts with myostatin, oligonucleotide probes can be designed based on the sequence encoding an activin receptor, for example, a sequence encoding the extracellular domain, which binds myostatin, and used to screen a library prepared from cells such as muscle cells or adipocytes, which are responsive to myostatin, thus facilitating identification of a polynucleotide encoding a myostatin receptor. Selected clones can be further screened, for example, by subcloning the inserts into an expression vector and, following expression of the cloned sequences, screening the expressed polypeptides using myostatin.

A polynucleotide of the invention, for example, a polynucleotide encoding a myostatin receptor, can be derived from a vertebrate species, including a mammalian, avian, or piscine species, or from an invertebrate species. Screening procedures that rely on nucleic acid hybridization allow the isolation any gene sequence from any organism, provided the appropriate probe is available. Oligonucleotide probes that correspond to a part of the sequence encoding the protein in question can be synthesized chemically. This requires that short, oligopeptide stretches of amino acid sequence are known. A polynucleotide sequence encoding the receptor can be deduced from the genetic code, taking into account the degeneracy of the genetic code. Thus, mixed addition reactions can be performed when the sequence is degenerate. This includes a heterogeneous mixture of denatured double stranded DNA. For such screening, hybridization is preferably performed on either single stranded DNA or denatured double stranded DNA. Hybridization is particularly useful in the detection of cDNA clones derived from sources where an extremely low amount of mRNA sequences relating to the polypeptide of interest are present. Thus, by using stringent hybridization conditions directed to avoid nonspecific binding, autoradiographic visualization can be used to identify a specific cDNA clone by the hybridization of the target DNA to an oligonucleotide probe in the mixture that is the complete complement of the target nucleic acid (Wallace et al., *Nucl. Acid Res.*, 9:879, 1981, which is incorporated herein by reference). Alternatively, a subtractive library can be used, thereby eliminating nonspecific cDNA clones.

When the entire amino acid sequence of a desired polypeptide is not known, the direct synthesis of DNA sequences is not possible and the method of choice is the synthesis of cDNA sequences. Among the standard procedures for isolating cDNA sequences of interest is the formation of cDNA libraries prepared in plasmids or phage, wherein the libraries are derived from reverse transcription of mRNA that is abundant in donor cells having a high level of genetic expression. When used in combination with polymerase chain reaction technology, even rare expression products can be cloned. Where significant portions of the amino acid sequence of the polypeptide are known, the production of labeled single stranded or double stranded DNA or RNA probe sequences duplicating a sequence putatively present in the target cDNA can be employed in hybridization procedures carried out on cloned copies of the cDNA, which have been denatured into a single stranded form (Jay et al., *Nucl. Acid Res.*, 11:2325, 1983, which is incorporated herein by reference).

A cDNA expression library, such as a lambda gt11 library, can be screened for GDF receptor peptides using an antibody specific for a GDF receptor, for example, an anti-Act RIIB antibody. The antibody can be polyclonal or monoclonal, and can be used to detect expression product indicative of the presence of a GDF receptor cDNA. Such an expression library also can be screened with a GDF peptide, for example, with myostatin, or a functional peptide portion thereof, to identify a clone encoding at least a portion of a myostatin binding domain of a myostatin receptor.

Polynucleotides encoding mutant GDF receptors and mutant GDF receptor polypeptides are also encompassed within the invention. An alteration in a polynucleotide encoding a GDF receptor can be an intragenic mutation such as point mutation, nonsense (STOP) mutation, missense mutation, splice site mutation or frameshift, or can be a heterozygous or homozygous deletion, and can be a naturally occurring mutation or can be engineered using recombinant DNA methods, for example. Such alterations can be detected using standard methods known to those of skill in the art, including, but not limited to, nucleotide sequence analysis, Southern blot analysis, a PCR based analysis such as multiplex PCR or sequence tagged sites (STS) analysis, or in situ hybridization analysis. GDF receptor polypeptides can be analyzed by standard SDS-PAGE, immunoprecipitation analysis, western blot analysis, or the like. Mutant GDF receptors are exemplified by truncated GDF receptors, including a soluble extracellular domain, which can have the ability to specifically bind its cognate GDF, but lacks a kinase domain; an intracellular GDF receptor kinase domain, which can exhibit constitutive kinase activity; as well as by GDF receptors that contain a point mutation, which disrupts the kinase activity of the receptor or the ligand binding ability of the receptor; and the like. Such GDF receptor mutants are useful for modulating GDF signal transduction and, therefore, for practicing various methods of the invention.

A polynucleotide encoding a GDF receptor can be expressed in vitro by introducing the polynucleotide into a suitable host cell. "Host cells" can be any cells in which the particular vector can be propagated, and, where appropriate, in which a polynucleotide contained in the vector can be expressed. The term "host cells" includes any progeny of an original host cell. It is understood that all progeny of the host cell may not be identical to the parental cell due, for example, to mutations that occur during replication. However, such progeny are included when the term "host cell" is used. Methods of obtaining a host cell that transiently or stably contains an introduced polynucleotide of the invention are well known in the art.

A GDF receptor polynucleotide of the invention can be inserted into a vector, which can be a cloning vector or a recombinant expression vector. The term "recombinant expression vector" refers to a plasmid, virus or other vehicle known in the art that has been manipulated by insertion or incorporation of a polynucleotide, particularly, with respect to the present invention, a polynucleotide encoding all or a peptide portion of a GDF receptor. Such expression vectors contain a promoter sequence, which facilitates the efficient transcription of the inserted genetic sequence of the host. The expression vector generally contains an origin of replication, a promoter, as well as specific genes which allow phenotypic selection of the transformed cells. Vectors suitable for use in the present invention include, but are not limited to, the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter, which can be a T7 promoter, metallothionein I promoter, polyhedrin promoter, or other promoter as desired, particularly tissue specific promoters or inducible promoters.

A polynucleotide sequence encoding a GDF receptor can be expressed in either prokaryotes or eukaryotes. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example, whether the polynucleotide is to be expressed preferentially in a particular cell type or under particular conditions (see, for example, Sambrook et al., supra, 1989).

A variety of host cell/expression vector systems can be utilized to express a GDF receptor coding sequence, including, but not limited to, microorganisms such as bacteria transformed with recombinant bacteriophage DNA, plasmid DNA or cosmid DNA expression vectors; yeast cells transformed with recombinant yeast expression vectors; plant cell systems infected with recombinant virus expression vectors such as a cauliflower mosaic virus or tobacco mosaic virus, or transformed with recombinant plasmid expression vector such as a Ti plasmid; insect cells infected with recombinant virus expression vectors such as a baculovirus; animal cell systems infected with recombinant virus expression vectors such as a retrovirus, adenovirus or vaccinia virus vector; and transformed animal cell systems genetically engineered for stable expression. Where the expressed GDF receptor is post-translationally modified, for example, by glycosylation, it can be particularly advantageous to select a host cell/expression vector system that can effect the desired modification, for example, a mammalian host cell/expression vector system.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516-544, 1987). For example, when cloning in bacterial systems, inducible promoters such as pL of bacteriophage λ, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

In yeast cells, a number of vectors containing constitutive or inducible promoters can be used (see Ausubel et al., supra, 1987, see chapter 13; Grant et al., *Meth. Enzymol.* 153:516-544, 1987; Glover, *DNA Cloning* Vol. II (IRL Press, 1986), see chapter 3; Bitter, *Meth. Enzymol.* 152:673-684, 1987; see, also, *The Molecular Biology of the Yeast Saccharomyces* (Eds., Strathern et al., Cold Spring Harbor Laboratory Press, 1982), Vols. I and II). A constitutive yeast promoter such as ADH or LEU2 or an inducible promoter such as GAL can be used (Rothstein, *DNA Cloning* Vol. II (supra, 1986), chapter 3). Alternatively, vectors can be used which promote integration of foreign DNA sequences into the yeast chromosome.

Eukaryotic systems, particularly mammalian expression systems, allow for proper post-translational modifications of expressed mammalian proteins. Eukaryotic cells which possess the cellular machinery for proper processing of the primary transcript, glycosylation, phosphorylation, and advantageously, plasma membrane insertion of the gene product can be used as host cells for the expression of a GDF receptor polypeptide, or functional peptide portion thereof.

Mammalian cell systems which utilize recombinant viruses or viral elements to direct expression can be engineered. For example, when using adenovirus expression vectors, the GDF receptors coding sequence can be ligated to an adenovirus transcription/translation control complex, e.g., the late promoter and tripartite leader sequence. Alternatively, the vaccinia virus 7.5K promoter can be used (Mackett et al., *Proc. Natl. Acad. Sci. USA* 79:7415-7419, 1982; Mackett et al., *J. Virol.* 49:857-864, 1984; Panicali et al., *Proc. Natl. Acad. Sci. USA* 79:4927-4931, 1982). Particularly useful are bovine papilloma virus vectors, which can replicate as extrachromosomal elements (Sarver et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host cell chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the GDF receptors gene in host cells (Cone and Mulligan, *Proc. Natl. Acad. Sci., USA* 81:6349-6353, 1984). High level expression can also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with the GDF receptors cDNA controlled by appropriate expression control elements such as promoter, enhancer, sequences, transcription terminators, and polyadenylation sites, and a selectable marker. The selectable marker in the recombinant plasmid can confer resistance to the selection, and allows cells to stably integrate the plasmid into their chromosomes and grow to form foci, which, in turn can be cloned and expanded into cell lines. For example, following the introduction of foreign DNA, engineered cells can be allowed to grow for 1 to 2 days in an enriched media, and then are switched to a selective media. A number of selection systems can be used, including, but not limited to, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci., USA* 48:2026, 1982), and adenine phosphoribosyltransferase (Lowy, et al., *Cell* 22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare et al., *Proc. Natl. Acad. Sci., USA* 78: 1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984) genes. Additional selectable genes, including trpB, which allows cells to utilize indole in place of tryptophan; hisD, which allows cells to utilize histinol in place of histidine (Hartman and Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue, *Curr. Comm. Mol. Biol.* (Cold Spring Harbor Laboratory Press, 1987), also have been described.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be cotransformed with DNA sequences encoding the GDF receptors of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Gluzman, *Eukarvotic Viral Vectors* (Cold Spring Harbor Laboratory Press, 1982)).

The invention also provides stable recombinant cell lines, the cells of which express GDF receptor polypeptides and contain DNA that encodes GDF receptors. Suitable cell types include, but are not limited to, NIH 3T3 cells (murine), C2C12 cells, L6 cells, and P19 cells. C2C12 and L6 myoblasts differentiate spontaneously in culture and form myotubes depending on the particular growth conditions (Yaffe and Saxel, *Nature* 270:725-727, 1977; Yaffe, *Proc. Natl. Acad. Sci. USA* 61:477-483, 1968). P19 is an embryonal carcinoma cell line. Such cells are described, for example, in the Cell Line Catalog of the American Type Culture Collection (ATCC). These cells can be stably transformed using well known methods (see, for example, Ausubel et al., supra, 1995, see sections 9.5.1-9.5.6).

A GDF receptor can be expressed from a recombinant polynucleotide of the invention using inducible or constitutive regulatory elements, as described herein. The desired protein encoding sequence and an operably linked promoter can be introduced into a recipient cell either as a non-replicating DNA (or RNA) molecule, which can either be a linear molecule or a covalently closed circular molecule. Expression of the desired molecule can occur due to transient expression of the introduced sequence, or the polynucleotide can be stably maintained in the cell, for example, by integration into a host cell chromosome, thus allowing a more permanent expression. Accordingly, the cells can be stably or transiently transformed (transfected) cells.

An example of a vector that can be employed is one which is capable of integrating the desired gene sequences into the host cell chromosome. Cells which have stably integrated the introduced DNA into their chromosomes can be selected by also introducing one or more markers which allow for selection of host cells which contain the expression vector. The marker can complement an auxotrophy in the host such as leu2, or ura3, which are common yeast auxotrophic markers; can confer a biocide resistance, for example, to an antibiotic or to heavy metal ions such as copper, or the like. The selectable marker gene can either be directly linked to the DNA gene sequences to be expressed, or can be introduced into the same cell by cotransfection.

The introduced sequence can be incorporated into a plasmid or viral vector capable of autonomous replication in the recipient host. Any of a variety of vectors can be employed for this purpose. Factors of importance in selecting a particular plasmid or viral vector include the ease with which recipient cells that contain the vector can be recognized and selected from those cells that do not contain the vector; the number of copies of the vector desired in a particular host cell; and whether it is desirable to be able to "shuttle" the vector between host cells of different species.

For a mammalian host, several vector systems are available for expression. One class of vectors utilizes DNA elements that provide autonomously replicating extra-chromosomal plasmids derived from animal viruses, for example, a bovine papilloma virus, polyoma virus, adenovirus, or SV40 virus. A second class of vectors includes vaccinia virus expression vectors. A third class of vectors relies upon the integration of the desired gene sequences into the host chromosome. Cells that have stably integrated the introduced DNA into their chromosomes can be selected by also introducing one or more markers genes (as described above), which allow selection of host cells that contain the expression vector. The selectable marker gene can be directly linked to the DNA sequences to be expressed, or introduced into the same cell by cotransfection. Additional elements can be included to provide for optimal synthesis of an encoded mRNA or peptide, including, for example, splice signals, transcription promoters or enhancers, and transcription or translation termination signals. cDNA expression vectors incorporating appropriate regulatory elements are well known in the art (see, for example, Okayama, *Mol. Cell. Biol.* 3:280, 1983).

Once the vector or DNA sequence containing the construct has been prepared for expression, the DNA construct can be introduced into an appropriate host. Various methods can be used for introducing the polynucleotide into a cell, including, for example, methods of transfection or transformation such as protoplast fusion, calcium phosphate precipitation, and electroporation or other conventional techniques, for example, infection where the vector is a viral vector.

The invention also provides transgenic animals, which have cells that express a recombinant GDF receptor. Such transgenic animals can be selected to have decreased fat content or increased muscle mass, or both, and, therefore, can be useful as a source of food products with high muscle and protein content, and reduced fat and cholesterol content. The animals have been altered chromosomally in their germ cells and somatic cells such that the production of a GDF, particularly myostatin, is maintained at a normal" level, but the myostatin receptor is produced in reduced amounts, or is completely disrupted, resulting in the cells in the animals having a decreased ability to bind myostatin and, consequently, having greater than normal levels of muscle tissue, preferably without increased fat or cholesterol levels. Accordingly, the present invention also includes food products provided by the animals. Such food products have increased nutritional value because of the increase in muscle tissue. The transgenic non-human animals of the invention include bovine, porcine, ovine and avian animals, as well as other vertebrates, and further includes transgenic invertebrates.

The invention also provides a method of producing animal food products having increased muscle content. Such a method can include modifying the genetic makeup of the germ cells of a pronuclear embryo of the animal, implanting the embryo into the oviduct of a pseudopregnant female, thereby allowing the embryo to mature to full term progeny, testing the progeny for presence of the transgene to identify transgene positive progeny, crossbreeding transgene positive progeny to obtain further transgene positive progeny, and processing the progeny to obtain a foodstuff. The modification of the germ cell comprises altering the genetic composition so as to reduce or inhibit the expression of the naturally occurring gene encoding for production of a myostatin receptor protein. For example, the transgene can comprise an antisense molecule that is specific for a polynucleotide encoding a myostatin receptor; can comprise a non-functional sequence that replaces or intervenes in the endogenous myostatin receptor gene or the transgene; or can encode a myostatin receptor antagonist, for example, a dominant negative myostatin receptor such as a dominant negative Act RIIB.

As used herein, the term "animal" refers to any bird, fish or mammal, except a human, and includes any stage of development, including embryonic and fetal stages. Farm animals such as pigs, goats, sheep, cows, horses, rabbits and the like; rodents such as mice; and domestic pets such as cats and dogs are included within the meaning of the term "animal." In addition, the term "organism" is used herein to include animals as described above, as well as other eukaryotes, including, for example, other vertebrates such as reptiles and amphibians, as well as invertebrates as described above.

As used herein, the term "transgenic," when used in reference to an animal or an organism, means that cells of the animal or organism have been genetically manipulated to contain an exogenous polynucleotide sequence that is stably maintained with the cells. The manipulation can be, for example, microinjection of a polynucleotide or infection with a recombinant virus containing the polynucleotide. Thus, the term "transgenic" is used herein to refer to animals (organisms) in which one or more cells receive a recombinant polynucleotide, which can be integrated into a chromosome in the cell, or can be maintained as an extrachromosomally replicating polynucleotide, such as might be engineered into a yeast artificial chromosome. The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, the offspring also are considered to be transgenic animals. The invention further encompasses transgenic organisms.

A transgenic organism can be any organism whose genome has been altered by in vitro manipulation of an early stage embryo or a fertilized egg, or by any transgenic technology to induce a specific gene knock-out. The term "gene knock-out" refers to the targeted disruption of a gene in a cell or in vivo that results in complete loss of function. A target gene in a transgenic animal can be rendered nonfunctional by an insertion targeted to the gene to be rendered nonfunctional, for example, by homologous recombination, or by any other method for disrupting the function of a gene in a cell.

The transgene to be used in the practice of the subject invention can be a DNA sequence comprising a modified GDF receptors coding sequence. Preferably, the modified GDF receptor gene is one that is disrupted by homologous targeting in embryonic stem cells. For example, the entire mature C-terminal region of the GDF receptors gene can be deleted (see Example 13). Optionally, the disruption (or deletion) can be accompanied by insertion of or replacement with another polynucleotide, for example, a nonfunctional GDF receptor sequence. A "knock-out" phenotype also can be conferred by introducing or expressing an antisense GDF receptor polynucleotide in a cell in the organism, or by expressing an antibody or a dominant negative GDF receptor in the cells. Where appropriate, polynucleotides that encode proteins having GDF receptor activity, but that differ in nucleotide sequence from a naturally occurring GDF gene sequence due to the degeneracy of the genetic code, can be used herein, as can truncated forms, allelic variants and interspecies homologs.

The present invention also provides antibodies that specifically bind a GDF receptor, and that block GDF binding to the receptor. Such antibodies can be useful, for example, for ameliorating a pathologic condition such as a cell proliferative disorder associated with muscle tissue.

A monoclonal antibody that binds specifically to a GDF receptor, particularly to a myostatin receptor, can increase the development of skeletal muscles. In preferred embodiments of the claimed methods, a GDF receptor monoclonal antibody, polypeptide, or polynucleotide is administered to a patient suffering from a pathologic condition such as a muscle wasting disease, a neuromuscular disorder, muscle atrophy, aging, or the like. The GDF receptor antibody, particularly an anti-myostatin receptor antibody, can also be administered to a patient suffering from a pathologic condition such as a muscular dystrophy, spinal cord injury, traumatic injury, congestive obstructive pulmonary disease (COPD), AIDS or cachexia.

In a preferred embodiment, the anti-myostatin receptor antibody is administered to a patient with muscle wasting disease or disorder by intravenous, intramuscular or subcutaneous injection; preferably, a monoclonal antibody is administered within a dose range between about 0.1 µg/kg to about 100 mg/kg; more preferably between about 1 µg/kg to 75 mg/kg; most preferably from about 10 mg/kg to 50 mg/kg. The antibody can be administered, for example, by bolus injunction or by slow infusion. Slow infusion over a period of 30 minutes to 2 hours is preferred. The anti-myostatin receptor antibody, or other anti-GDF receptor antibody, can be formulated in a formulation suitable for administration to a patient. Such formulations are known in the art.

The dosage regimen will be determined by the attending physician considering various factors which modify the action of the myostatin receptor protein, for example, amount of tissue desired to be formed, the site of tissue damage, the condition of the damaged tissue, the size of a wound, type of damaged tissue, the patient's age, sex, and diet, the severity of any infection, time of administration and other clinical factors. The dosage can vary with the type of matrix used in the reconstitution and the types of agent, such as anti-myostatin receptor antibodies, to be used in the composition. Generally, systemic or injectable administration, such as intravenous, intramuscular or subcutaneous injection. Administration generally is initiated at a dose which is minimally effective, and the dose is increased over a preselected time course until a positive effect is observed. Subsequently, incremental increases in dosage are made limiting such incremental increases to such levels that produce a corresponding increase in effect, while taking into account any adverse affects that can appear. The addition of other known growth factors, such as IGF I (insulin like growth factor I), human, bovine, or chicken growth hormone, which can aid in increasing muscle mass, to the final composition, can also affect the dosage. In the embodiment where an anti-myostatin receptor antibody is administered, the antibody is generally administered within a dose range of about 0.1 µg/kg to about 100 mg/kg.; more preferably between about 10 mg/kg to 50 mg/kg.

As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope of a GDF receptor, for example, a myostatin receptor. In addition, as discussed above, an antibody of the invention can be an antibody that specifically binds a peptide portion of a promyostatin polypeptide, particularly a myostatin prodomain or functional peptide portion thereof. It will be recognized that the following methods, which exemplify the preparation and characterization of GDF receptor antibodies, further are applicable to the preparation and characterization of additional antibodies of the invention, including antibodies that specifically bind a myostatin prodomain, antibodies that specifically bind a promyostatin polypeptide and reduce or inhibit proteolytic cleavage of the promyostatin to myostatin, and the like The term "binds specifically" or "specific binding activity," when used in reference to an antibody means that an interaction of the antibody and a particular epitope has a dissociation constant of at least about $1\times10^{-6}$, generally at least about $1\times10^{-7}$ usually at least about $1\times10^{-8}$, and particularly at least about $1\times10^{-9}$ or $1\times10^{-10}$ or less. As such, Fab, F(ab')$_2$, Fd and Fv fragments of an antibody that retain specific binding activity for an epitope of a GDF receptor, are included within the definition of an antibody. For purposes of the present invention, an antibody that reacts specifically with an epitope of a myostatin receptor, for example, is considered to not substantially react with a TGF-β receptor or a BMP receptor if the antibody has at least a two-fold greater binding affinity, generally at least a five-fold greater binding affinity, and particularly at least a ten-fold greater binding affinity for the myostatin receptor as compared to the TGF-β or BMP receptor.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989), which is incorporated herein by reference). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1.988); Hilyard et al., *Protein Engineering: A practical approach* (IRL Press 1992); Borrabeck, *Antibody Engineering,* 2d ed. (Oxford University Press 1995); each of which is incorporated herein by reference).

Antibodies that bind specifically with a GDF receptor can be raised using the receptor as an immunogen and removing antibodies that crossreact, for example, with a TGF-β type I or type II receptor, with an activin receptor such as Act RIB, Act RIIA or Act RIIB, or a BMP receptors such as BMP RII, BMP RIA and BMP RIB (see Massague, supra, 1998). An antibody of the invention conveniently can be raised using a peptide portion of a myostatin receptor that is not present in a TGF-β, activin, or BMP receptor. Similarly, an antibody that specifically binds a myostatin prodomain can be raised using the prodomain, or a functional peptide portion thereof as the immunogen. Where such a peptide is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988).

If desired, a kit incorporating an antibody or other agent useful in a method of the invention can be prepared. Such a kit can contain, in addition to the agent, a pharmaceutical composition in which the agent can be reconstituted for administration to a subject. The kit also can contain, for example, reagents for detecting the antibody, or for detecting specific binding of the antibody to a GDF receptor. Such detectable reagents useful for labeling or otherwise identifying the antibody are described herein and known in the art.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1; each or which is incorporated herein by reference). In addition, monoclonal antibodies can be obtained using methods that are well known and routine in the art (Harlow and Lane, supra, 1988). For example, spleen cells from a mouse immunized with a myostatin receptor, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. The antibodies can be further screened for the inability to bind specifically with the myostatin receptor. Such antibodies are useful, for example, for preparing standardized kits for clinical use. A recombinant phage that expresses, for example, a single chain anti-myostatin receptor antibody also provides an antibody that can used for preparing standardized kits.

Methods of preparing monoclonal antibodies well known (see, for example, Kohler and Milstein, *Nature* 256:495, 1975, which is incorporated herein by reference; see, also, Coligan et al., supra, 1992, see sections 2.5.1-2.6.7; Harlow and Lane, supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well established techniques, including, for example, affinity chromatography with Protein-A SEPHAROSE gel, size exclusion chromatography, and ion exchange chromatography (Coligan et al., supra, 1992, see sections 2.7.1-2.7.12 and sections 2.9.1-2.9.3; see, also, Barnes et al., "Purification of Immunoglobulin G (IgG)," in *Meth. Molec. Biol.* 10:79-104 (Humana Press 1992), which is incorporated herein by reference). Methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention can also be derived from subhuman primate antibody. General techniques for raising therapeutically useful antibodies in baboons can be found, for example, in Goldenberg et al., International Patent Publication WO 91/11465 (1991); and Losman et al., *Int. J. Cancer* 46:310, 1990, each of which is incorporated herein by reference.

A therapeutically useful anti-GDF receptor antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions: General techniques for cloning murine immunoglobulin variable domains are known (see, for example, Orlandi et al., *Proc. Natl. Acad. Sci., USA* 86:3833, 1989, which is hereby incorporated in its entirety by reference). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. USA*

89:4285, 1992; Sandhu, *Crit. Rev. Biotechnol.* 12:437, 1992; and Singer et al., *J. Immunol.* 150:2844, 1993; each of which is incorporated herein by reference).

Antibodies of the invention also can be derived from human antibody fragments isolated from a combinatorial human immunoglobulin library (see, for example, Barbas et al., *METHODS: A Companion to Methods in Immunology* 2:119, 1991; Winter et al., *Ann. Rev. Immunol.* 12:433, 1994; each of which is incorporated herein by reference). Cloning and expression vectors that are useful for producing a human immunoglobulin phage library can be obtained, for example, from STRATAGENE Cloning Systems (La Jolla, Calif.).

An antibody of the invention also can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immunol.* 6:579, 1994; each of which is incorporated herein by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647, each of which is incorporated by reference, and references contained therein; Nisonhoff et al., *Arch. Biochem. Biophvs.* 89:230, 1960; Porter, *Biochem. J.* 73:119, 1959; Edelman et al., *Meth. Enzymol.*, 1:422 (Academic Press 1967), each of which is incorporated herein by reference; see, also, Coligan et al., supra, 1992, see sections 2.8.1-2.8.10 and 2.10.1-2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains. This association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, supra, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Methods in Enzymology 2: 97, 1991; Bird et al., *Science* 242:423-426, 1988; Ladner et al., U.S. Pat. No. 4,946,778; Pack et al., *Bio/Technology* 11: 1271-1277, 1993; each of which is incorporated herein by reference; see, also Sandhu, supra, 1992.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzamology* 2:106, 1991, which is incorporated herein by reference).

The invention also provides a method for identifying a GDF receptor polypeptide. Such a method can be performed, for example, by incubating components comprising GDF polypeptide and a cell expressing a full length receptor or truncated receptor under conditions sufficient to allow the GDF to bind to the receptor; measuring the binding of the GDF polypeptide to the receptor; and isolating the receptor. The GDF can be any of the known GDFs (e.g., GDF-1-16), and preferably is GDF-8 (myostatin) or GDF-11. Methods of isolating the receptors are described in more detail in the Examples section below. Accordingly, the invention also provides a substantially purified GDF receptor, as well as peptides and peptide derivatives of a GDF receptor that have fewer amino acid residues than a naturally occurring GDF receptor. Such peptides and peptide derivatives are useful as research and diagnostic tools in the study of muscle wasting diseases and the development of more effective therapeutics.

The invention further provides GDF receptor variants. As used herein, the term "GDF receptors variant" means a molecule that simulates at least part of the structure of GDF receptors. GDF receptor variants can be useful in reducing or inhibiting GDF binding, thereby ameliorating a pathologic condition as disclosed herein. Examples of GDF receptor variants include, but are not limited to, truncated GDF receptors such as a soluble extracellular domain of a GDF receptor; a dominant negative GDF receptor such as a dominant negative Act RIIB receptor, which lacks kinase activity; or other truncated or mutant GDF receptors.

The invention relates not only to peptides and peptide derivatives of a naturally-occurring GDF receptor, but also to GDF receptor variants, including mutants GDF receptors, and chemically synthesized derivatives of GDF receptors that specifically bind a GDF, for example, myostatin. For example, changes in the amino acid sequence of a GDF receptor are contemplated in the present invention. GDF receptors can be altered by changing the DNA encoding the protein. Preferably, only conservative amino acid alterations are undertaken, using amino acids that have the same or similar properties. Illustrative amino acid substitutions include the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Variants useful for the present invention comprise analogs, homologs, muteins and mimetics of a GDF receptor that retain the ability to specifically bind to their respective GDFs. In another embodiment, variant GDF receptors that have dominant negative activity also are contemplated, regardless of whether the variant also interacts specifically with its GDF. Peptides of the GDF receptors refer to portions of the amino acid sequence of GDF receptors that have these abilities. The variants can be generated directly from GDF receptors itself by chemical modification, by proteolytic enzyme digestion, or by combinations thereof. Additionally, genetic engineering techniques, as well as methods of synthesizing polypeptides directly from amino acid residues, can be employed.

Peptides can be synthesized by such commonly used methods as t-BOC or FMOC protection of alpha-amino groups. Both methods involve stepwise syntheses whereby a single amino acid is added at each step starting from the C terminus of the peptide (Coligan, et al., *Current Protocols in Immunology* (Wiley Interscience, 1991), Unit 9, which is incorporated herein by reference). Peptides of the invention can also be synthesized by the well known solid phase peptide synthesis methods (Merrifield, *J. Am. Chem. Soc.,* 85:2149, 1962; Stewart and Young, *Solid Phase Peptides Synthesis* (Freeman, San Francisco, 1969), see pages 27-62, each of which is incorporated herein by reference), using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Non-peptide compounds that mimic the binding and function of GDF receptors ("mimetics") can be produced by the approach outlined by Saragovi et al. (*Science* 253: 792-95, 1991, which is incorporated herein by reference). Mimetics are molecules which mimic elements of protein secondary structure (Johnson et al., "Peptide Turn Mimetics," in *Biotechnology and Pharmacy* (Pezzuto et al., Eds.; Chapman and Hall, New York 1993), which is incorporated herein by reference). The underlying rationale behind the use of peptide mimetics is that the peptide backbone of proteins exists chiefly to orient amino acid side chains in such a way as to facilitate molecular interactions. For the purposes of the present invention, an appropriate mimetic can be considered to be the equivalent of a GDF receptor.

Longer peptides can be produced by the "native chemical" ligation technique which links together peptides (Dawson et al., *Science* 266:776, 1994, which is incorporated herein by reference). Variants can be created by recombinant techniques employing genomic or cDNA cloning methods. Site specific and region directed mutagenesis techniques can be employed (Ausubel et al., supra, 1989 and 1990 to 1993 supplements), see volume 1, chapter 8; *Protein Engineering* (Oxender and Fox eds., A. Liss, Inc., 1987)). In addition, linker scanning and PCR mediated techniques can be employed for mutagenesis (Erlich, *PCR Technology* (Stockton Press 1989); Ausubel et al., supra, 1989 to 1993). Protein sequencing, structure and modeling approaches for use with any of the above techniques are disclosed in the above cited references.

The present invention also provides GDF receptor-binding agents that block the specific binding of a GDF to its receptor. Such agents are useful, for example, as research and diagnostic tools in the study of muscle wasting disorder as described above and as effective therapeutics, and can be identified using the methods as disclosed herein, for example, a molecular modeling method. In addition, pharmaceutical compositions comprising GDF receptor-binding agents can represent effective therapeutics. In the context of the invention, the phrase "GDF receptor-binding agent" denotes a naturally occurring ligand of a GDF receptor, for example, GDF-1 to GDF-16; a synthetic ligand of GDF receptors, or an appropriate derivative of the natural or synthetic ligands. The determination and isolation of ligands is well known in the art (Lerner, *Trends Neurosci.* 17:142-146, 1994, which is incorporated herein by reference).

In yet another embodiment, the present invention relates to GDF receptor-binding agents that interfere with binding between a GDF receptor and a GDF. Such binding agents can interfere by competitive inhibition, by non-competitive inhibition or by uncompetitive inhibition. Interference with normal binding between GDF receptors and one or more GDF can result in a useful pharmacological effect.

The invention also provides a method for identifying a composition that binds to a GDF receptor. The method includes incubating components comprising the composition and a GDF receptor under conditions sufficient to allow the components to interact specifically, and measuring the binding of the composition to GDF receptors. Compositions that bind to GDF receptors include peptides, peptidomimetics, polypeptides, chemical compounds and biologic agents as described above. Incubating includes exposing the reactants to conditions that allow contact between the test composition and GDF receptors, and provide conditions suitable for a specific interaction as would occur in vivo. Contacting can be in solution or in solid phase. The test ligand/composition can optionally be a combinatorial library for screening a plurality of compositions, as described above. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki et al., *Bio/Technology* 3: 1008-1012, 1985, which is incorporated herein by reference), allele-specific oligonucleotide (ASO) probe analysis (Conner et al., *Proc. Natl. Acad. Sci. USA* 80:278, 1983, which is incorporated herein by reference), oligonucleotide ligation assays (OLAs) (Landegren et al., *Science* 241: 1077 1988, which is incorporated herein by reference), and the like (see Landegren et al., *Science* 242:229-237, 1988, which is incorporated herein by reference).

To determine if a composition can functionally complex with the receptor protein, induction of an exogenous gene can be monitored by monitoring changes in the protein level of a protein encoded for by the exogenous gene, or any other method as disclosed herein. When a compositions is identified that can induce transcription of the exogenous gene, it is concluded that this composition can specifically bind to the receptor protein coded for by the nucleic acid encoding the initial sample test composition.

Expression of the exogenous gene can be monitored by a functional assay or assay for a protein product, for example. The exogenous gene is therefore a gene that provides an assayable/measurable expression product in order to allow detection of expression of the exogenous gene. Such exogenous genes include, but are not limited to, reporter genes such as chloramphenicol acetyltransferase gene, an alkaline phosphatase gene, β-galactosidase, a luciferase gene, a green fluorescent protein gene, guanine xanthine phosphoribosyl-transferase, alkaline phosphatase, and antibiotic resistance genes such as neomycin phosphotransferase (see above).

Expression of the exogenous gene is indicative of a specific interaction of a composition and a GDF receptor; thus, the binding or blocking composition can be identified and isolated. The compositions of the present invention can be extracted and purified from the culture media or a cell by using known protein purification techniques commonly employed, including, for example, extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to GDF receptors, as described above. Thus, the screening method is also useful for identifying variants, binding or blocking agents, etc., which functionally, if not physically (e.g., sterically) act as antagonists or agonists, as desired.

The following examples are intended to illustrate but not limit the invention.

EXAMPLE 1

Myostatin Acts in a Dose Dependent Manner

This example demonstrates that the activity of myostatin in inhibiting muscle growth is dependent on the level of myostatin expression in vivo.

Myostatin is a negative regulator of skeletal muscle mass (McPherron et al., supra, 1997; McPherron and Lee, supra, 1997). Myostatin knock-out mice that were homozygous for a deletion of the myostatin gene had a 25-30% increase in total body mass. An examination of the homozygous knock-out mice revealed that the increased muscle mass was due to about a 100-200% increase in skeletal muscle mass throughout the body.

Mice that were heterozygous for the myostatin mutation also had an increase in total body mass. However, the increase mass of the heterozygotes was less than that of the homozygotes, and was statistically significant in only one age and sex group among the many examined. In order to determine whether heterozygous mice have an intermediate phenotype between that of wild type mice and homozygous myostatin knock-out mice, the analysis of muscle weights was extended to the heterozygous mice. Individual muscles sampled from heterozygous mice weighed approximately 25-50% more than those of wild type mice. These results demonstrate that mice that are heterozygous for deletion of a myostatin gene have a phenotype that is intermediate between that of wild type mice and homozygous myostatin knock-out mice, and demonstrate that myostatin produces a dose-dependent effect in vivo.

These results indicate that the manipulation of myostatin activity can be useful in treating muscle wasting diseases and other metabolic disorders associated with myostatin activity. Furthermore, the dose-dependent effect of myostatin indicates that a therapeutic effect can be obtained without achieving complete inhibition of myostatin activity, thereby allowing for an adjustment of myostatin activity if, for example, a certain level of activity produces undesirable effects in a subject.

EXAMPLE 2

Myostatin Effect Decreases with age in Knock-Out Mice

This example demonstrates that a decreased difference in body weight between wild type mice and homozygous myostatin knock-out mice is associated with a decline in muscle weight of the mutant mice.

Myostatin knock-out mice weighed approximately 25-30% more than wild type mice at five months of age (McPherron et al., supra, 1997). However, this difference in total body weights became significantly smaller or disappeared altogether as the animals aged. In order to determine whether this effect was due to a relative loss of weight in the knock-out mice due, for example, to muscle degeneration, or to a relatively greater weight gain by wild type mice, a detailed analysis of muscle weights was made as a function of age.

At all ages examined from 2 months to 17 months, the pectoralis muscle weighed significantly more in homozygous mutant mice than in wild type littermates. The most dramatic difference was observed at 5 months, at which time the pectoralis weight was approximately 200% greater in the mutant mice. Although the pectoralis weight declined slightly at older ages, the weight of this muscle in mutant mice remained greater than twice that of wild type mice. This same basic trend was observed in all of the other muscles examined, including the triceps brachii, the quadriceps, the gastrocnemius and plantaris, and the tibialis anterior. Similar trends were observed in both male and female mice. These results demonstrate that the decreased difference in total body weights between mutant and wild type mice observed with aging is due to a slight decline in muscle weights in the mutant mice.

EXAMPLE 3

Myostatin Affects Fat Accumulation in a Dose Dependent Manner

This example demonstrates that myostatin knock-out mice fail to accumulate fat, and that the decrease in fat accumulation is associated with the level of myostatin expression in vivo.

Since the decline in muscle weights in myostatin mutants, as demonstrated in Example 2, did not fully account for the observation that the wild type animals eventually weighed about the same as the mutant mice, the amount of fat accumulation in wild type and mutant mice was examined. The inguinal, epididymal and retroperitoneal fat pads in male mice were examined. There was no difference in the weights of any of these fat pads between wild type and mutant mice at two months of age. By 5 to 6 months of age, wild type and heterozygous knock-out mice both exhibited a large range of fat pad weights, and, on average, fad pad weights increased by approximately 3-fold to 5-fold by the time the animals reached 9 to 10 months of age. Due to the large range of fat pad weights observed in these animals, some animals showed a much larger increase (up to 10-fold) than others.

In contrast to the wild type and heterozygous knock-out mice, the fat pad weights of myostatin homozygous mutant mice were in a relatively narrow range and were virtually identical in 2 month old mice and in 9 to 10 month old mice. Thus, the increased fat accumulation that occurred with aging in the wild type mice was not observed in the homozygous myostatin knock-out mice. This difference in fat accumulation, together with the slight decline in muscle weights, as a function of age in the homozygous mutant mice fully accounted for the observation that the wild type animals eventually have the same total body weight as the mutants.

The mean fat pad weights of heterozygous knock-out mice at 9 to 10 months of age was intermediate between that of the wild type mice and the homozygous mutant mice. Although this difference was not statistically significant, due to the wide range of fat pad weights in these and the wild type mice, these results nevertheless indicate that myostatin has a dose-dependent effect on the accumulation of fat, similar to its effect on muscle growth.

EXAMPLE 4

Effect of Myostatin on Metabolism

This example demonstrates that serum insulin and glucose levels, as well as metabolic activity, are affected by the level of myostatin expression.

In order to determine whether the skeletal muscle hypertrophy and the lack of fat accumulation in the myostatin mutant mice is due to an effect on overall metabolism, the metabolic profile of the mutant mice was examined. Serum triglyceride and serum cholesterol levels were significantly lower in myostatin mutant mice as compared to wild type control mice (Table 1). Serum insulin levels also appeared to be lower in the myostatin mutant mice. However, the fed and fasting glucose levels both were indistinguishable among homozygous mutant mice and wild type mice (Table 1), and both groups of mice had a normal response in a glucose tolerance test. The results demonstrate that the homozygous myostatin knock-out mice can maintain normal levels of serum glucose even though their serum insulin level is lower than that of wild type animals.

TABLE 1

SERUM PARAMETERS

| | +/+ | -/- | |
|---|---|---|---|
| triglycerides (mg/dl) | 131.5 +/- 16.5 | 66.8 +/- 11.4 | p = 0.012 |
| cholesterol (mg/dl) | 138.3 +/- 8.1 | 94.5 +/- 6.8 | p = 0.0034 |
| fed glucose (mg/dl) | 114.0 +/- 4.8 | 119.3 +/- 5.2 | n.s. (p = 0.43) |
| fasting glucose (mg/dl) | 86.5 +/- 3.8 | 103.3 +/- 9.3 | n.s. (p = 0.13) |

+/+ indicates wild type mice; -/- indicate homozygous knock-out mice

In order to determine whether differences in metabolic rates could explain the lack of fat accumulation in the mutant mice, the rate of oxygen consumption of wild type and mutant mice was compared using a calorimeter. Mutant mice had a lower basal metabolic rate and a lower overall metabolic rate than wild type control mice. These results indicate that the lack of fat accumulation in the myostatin mutant mice is not due to a higher rate of metabolic activity.

EXAMPLE 5

Myostatin Affects Fat Accumulation in Genetically Obese Mice

This example demonstrates that a lack of myostatin expression suppresses fat accumulation in mice that are a genetic model for obesity.

In order to determine whether the loss of myostatin activity could suppress fat accumulation not only in normal mice but also in obese mice, the effect of the myostatin mutation in agouti lethal yellow (AY) mice, which represent a genetic model of obesity (Yen et al., *FASEB J.* 8:479-488, 1994), was examined. Mice that were doubly heterozygous for the lethal yellow and myostatin mutations were generated, and offspring from crosses of these doubly heterozygous mice were examined.

The total body weight of the $A^y$/a, myostatin -/- double mutant mouse was dramatically reduced (approximately 9 grams) compared to that of the $A^y$/a, myostatin +/+ mouse. This reduction in total body weight was even more dramatic considering that the $A^y$/a, myostatin -/- double mutant had about 2 to 3 times more skeletal muscle than did the $A^Y$/a, myostatin +/+ mouse. The double mutant had approximately 10 grams more muscle than the $A^y$/a, myostatin +/+ mouse and, therefore, the total weight reduction in the rest of the tissues was about 19 grams.

The reduction in total body weight resulted from a reduction in overall fat content. As shown in Table 2, the weights of the parametrial and retroperitoneal fat pads were reduced 5-fold to 6-fold in the $A^y$/a, myostatin -/- double mutant as compared to the $A^y$/a, myostatin +/+ mouse. These results indicate that the presence of the myostatin mutation dramatically suppresses fat accumulation in obesity.

The presence of the myostatin mutation also dramatically affected glucose metabolism. Agouti lethal mice lacking the myostatin mutation had grossly abnormal glucose tolerance test results, with serum glucose levels often reaching 450 to 600 mg/dl and only slowly recovering to baseline levels over a period of 4 hours. Female agouti lethal mice were affected less than male mice, and some females responded almost normally in this test, as previously described (see Yen et al., supra, 1994). In contrast, although the Ay/a, myostatin -/- mice had slightly abnormal glucose tolerance tests, but none of these animals had the gross abnormalities observed in the Ay/a myostatin +/+ mice.

These results indicate that the myostatin mutation at least partially suppressed the development of abnormal glucose metabolism in the agouti lethal mice. Significantly, mice that were heterozygous for the myostatin mutation had an intermediate response compared to myostatin +/+ and myostatin -/- mice, thus confirming the dose-dependent effect of myostatin.

EXAMPLE 6

Purification of Recombinant Myostatin

This example provides a method for preparing and isolating recombinant myostatin.

In order to elucidate the biological activity of myostatin, large quantities of myostatin protein were purified for bioassays. Stable Chinese hamster ovary (CHO) cell lines producing high levels of myostatin protein were generated by co-amplifying a myostatin expression cassette with a dihydrofolate reductase cassette using a methotrexate selection scheme (McPherron et al., supra, 1997). Myostatin was purified from the conditioned medium of the highest producing line by successive fractionation on hydroxyapatite, lentil lectin SEPHAROSE gel, DEAE agarose, and heparin SEPHAROSE gel. Silver stain analysis revealed that the purified protein obtained following these four column chromatography steps (referred to as "heparin eluate") consisted of two species with molecular masses of approximately 35 liodaltons (kDa) and 12 kDa.

The purified protein preparation was determined by various criteria to represent a complex of two myostatin prodomain peptides and a disulfide-linked dimer of mature C-terminal myostatin peptides. First, western blot analysis, using antibodies raised against specific portions of the promyostatin sequence, identified the 35 kDa band as the prodomain and the 12 kDa band as the mature C-terminal peptide. Second, under non-reducing conditions, the species reacting with antibodies directed against the mature C-terminal peptide had an electrophoretic mobility consistent with a disulfide linked dimer. Third, the molar ratio of prodomain to mature C-terminal peptide was approximately 1:1. Fourth, the prodomain and mature C-terminal peptide copurified through the four column chromatography steps. Finally, the mature C-terminal peptide bound to the lentil lectin column even though the C-terminal region does not contain consensus N-linked glycosylation signals, indicating that the mature C-terminal peptide bound to the column due to its interaction with the prodomain peptide, which contains a potential N-linked glycosylation site.

These results indicate that myostatin produced by the genetically modified CHO cells is secreted in a proteolytically processed form, and that the resulting prodomain and mature C-terminal region associate non-covalently to form a complex containing two prodomain peptides and a disulfide-linked dimer of C-terminal proteolytic fragments, similar to that described for TGF-β. In the TGF-β complex, the C-terminal dimer exists in an inactive, latent form (Miyazono et al., *J. Biol. Chem.* 263:6407-6415, 1988), and the active species can be released from this latent complex by treatment with acid, chaotropic agents, reactive oxygen species, or plasmin, or by interactions with other proteins, including thrombospondin and integrin αvB6 (Lawrence et al., *Biochem. Biophvs. Res. Comm.* 133:1026-1034, 1985; Lyons et al., *J. Cell Biol.* 106:1659-1665, 1988; Schultz-Chemy and Murphy-Ullrich, *J. Cell Biol.* 122:923-932, 1993; Barcellos-Hoff and Dix, *Mol. Endocrinol.* 10:1077-1083, 1996; Munger et al., *Cell* 96:319-328, 1999). Furthermore, the addition of purified prodomain peptide (also known as latency-associated peptide or LAP) to the TGF-β complex inhibits the biological activity of the purified C-terminal dimer in vitro and in vivo (Gentry and Nash, *Biochemistry* 29:6851-6857, 1990; Bottinger et al., *Proc. Natl. Acad. Sci. USA* 93:5877-5882, 1996).

The heparin eluate, which consisted of a complex of prodomain and mature C-terminal peptide, was further purified using an HPLC C4 reversed phase column. The C-terminal dimer eluted from the HPLC column earlier than the prodomain, thus allowing the isolation of the C-terminal dimer free of prodomain. Fractions that contained mostly prodomain also were obtained, although these fractions contained small amounts of the C-terminal dimer. Some of the protein also was present as higher molecular weight complexes. The nature of the higher molecular weight complexes is unknown, but, based on western blot analysis in the presence or absence of reducing agents, these complexes can contain at least one prodomain peptide and one C-terminal mature myostatin peptide linked by one or more disulfide bonds. In fact, most of the mature C-terminal peptide present in the HPLC fraction enriched for the propeptide (HPLC fractions 35-37) was present in these high molecular weight complexes. These higher molecular weight complexes likely represent improperly folded proteins that are secreted by the genetically modified CHO cells.

EXAMPLE 7

Myostatin Specifically Interacts with an Activin Receptor

This example demonstrates that myostatin specifically binds an activin type II receptor expressed on cells in culture, and that this specific binding is inhibited by a myostatin prodomain.

The receptors for some TGF-β family members have been identified, and most are single membrane spanning serine/threonine kinases (Massague and Weis-Garcia, *Cancer Surveys* 27:41-64, 1996). The activin type II receptors (Act RIIA and/or Act RIIB), for example, are known to bind members of the TGF-β superfamily. The phenotype of mice lacking the Act RIIB receptor showed anterior/posterior axial patterning defects and kidney abnormalities that were very similar to those observed in GDF-11 knock-out mice (McPherron et al., *Nat. Genet.* 22:260-264, 1999; Oh and Li, *Genes Devel.* 11:1812-1826, 1997). Since the amino acid sequences of GDF-11 and myostatin (GDF-8) are 90% identical in the mature C-terminal region, the ability of myostatin to specifically interact with a activin type II receptor was examined Myostatin was labeled by radio-iodination, and binding studies were performed using COS cells transfected with an Act RIIB expression construct. Myostatin interacted specifically with the transfected COS cells. Myostatin binding was competed in a dose dependent manner by excess unlabeled myostatin, and was significantly lower in control COS cells, which were transfected with an empty vector. No significant binding occurred to cells transfected with a BMP RII or TGF-β RII expression construct. Myostatin binding to Act RIIB-transfected cells was saturable, and the binding affinity was approximately 5 nM as determined by Scatchard analysis.

The receptor binding assay also was used to examine the ability of the myostatin prodomain to inhibit the ability of the mature C-terminal dimer to interact specifically with Act RIIB in this system. The addition of purified prodomain peptide blocked the ability of the C-terminal dimer to bind the Act RIIB transfected COS cells in a dose-dependent manner. These results indicate that the myostatin prodomain is a natural inhibitor of myostatin.

EXAMPLE 8

Increased Myostatin Levels Induce Weight Loss

This example demonstrates that elevated levels of myostatin can lead to substantial weight loss in vivo.

In one set of experiments, CHO cells that express myostatin were injected into nude mice. The nude mice that had myostatin expressing CHO cell tumors showed severe wasting over the course of approximately 12 to 16 days following injection of the cells. This wasting syndrome was not observed in nude mice injected with any of a variety of control CHO lines that had undergone a similar selection process but did not express myostatin. Furthermore, the myostatin coding sequence in the construct used to transfect the CHO cells was under the control of a metallothionein promoter, and the wasting syndrome was exacerbated when mice bearing the myostatin expressing tumors were maintained on water containing zinc sulfate. Western blot analysis revealed high levels of myostatin protein in the serum of the nude mice that bore the myostatin-expressing CHO cells. These results indicate that the wasting syndrome was induced in response to the elevated level of myostatin in the nude mice and, as discussed below, this result was confirmed by observing similar effects in mice injected with purified myostatin.

The dramatic weight loss observed in the nude mice bearing myostatin expressing CHO cells was due primarily to a disproportionate loss of both fat and muscle weight. White fat pad weights (intrascapular white, uterine, and retroperitoneal fat) were reduced by greater than 90% compared to mice bearing control CHO cell tumors. Muscle weights were also severely reduced, with individual muscles weighing approximately half as much in myostatin expressing mice as in control mice by day 16. This loss in muscle weight was reflected by a corresponding decrease in fiber sizes and protein content.

Mice bearing the myostatin expressing CHO cell tumors also became severely hypoglycemic. However, the weight loss and hypoglycemia were not due to a difference in food consumption, as all of the mice consumed equivalent amounts of food at each time interval examined during the 16 day course of the study. These results indicate that myostatin overexpression induces a dramatic weight loss, which resembles the cachectic wasting syndrome that occurs in patients suffering from chronic diseases such as cancer or AIDS.

With more chronic administrations using lower doses of myostatin, changes in fat weight were observed. For example; twice daily injections of 1 μg of myostatin protein for 7 days resulted in an approximately 50% decrease in the weights of a number of different white fat pads (intrascapular white, uterine, and retroperitoneal fat pads) with no significant effect on brown fat (intrascapular brown). These results confirm that myostatin can induce weight loss and, in extreme cases, a wasting syndrome in vivo.

EXAMPLE 9

Characterization of Myostatin Binding to an Activin Receptor

This example describes a method for characterizing the relationship of myostatin binding to an activin receptor with the biological effects produced by myostatin in vivo.

Act RIIA or Act RIIB knock-out mice can be used to confirm that Act RIIA or Act RIIB is a receptor for myostatin in vivo. A detailed muscle analysis of these mice can determine whether knock-out of an activin receptors is associated with a change in muscle fiber number or size. Since Act RIIA/Act RIIB double homozygous mutant die early during embryogenesis (Song et al., *Devel. Biol.* 213:157-169, 1999), only the various homozygous/heterozygous combinations can be examined. However, tissue-specific or conditional knock-out mice can be generated such that both genes can be "deleted" only in muscle tissue, thus allowing postnatal examination of the double homozygous knock-out mice.

The effect on adipose tissue can be examined with aging of the mice to determine whether the number of adipocytes or the accumulation of lipid by these adipocytes is altered in the knock-out mice. Adipocyte number and size is determined by preparing cell suspensions from collagenase treated tissue (Rodbell, *J. Biol. Chem.* 239:375-380, 1964; Hirsch and Gallian, *J. Lipid Res.* 9:110-119, 1968). Total lipid content in the animals is determined by measuring dry carcass weights and then the residual dry carcass weights after lipid extraction (Folch et al., *J. Biol. Chem.* 226:497-509, 1957).

A variety of serum parameters also can be examined, including fed and fasting glucose and insulin, triglycerides, cholesterol, and leptin. As disclosed above, serum triglycerides and serum insulin are decreased in the myostatin mutant animals. The ability of the activin receptor knock-out mice to respond to an exogenous glucose load also can be examined using glucose tolerance tests. As disclosed above, the response to a glucose load essentially was identical in wild type and myostatin mutant mice at 5 months of age. This observation can be extended by measuring these parameters in the mice as they age. Serum insulin levels also can be measured at various times during the glucose tolerance tests.

Basal metabolic rates also can be monitored using a calorimeter (Columbus Instruments). As disclosed above, myostatin mutant mice have a lower metabolic rate at 3 months of age than their wild type counterparts. This analysis can be extended to older mice, and the respiratory quotient also can be measured in these animals. The ability to maintain normal thermogenesis can be determined by measuring the basal body temperatures as well as their ability to maintain body temperature when placed at 4° C. Brown fat weights and expression levels of UCP1, UCP2, and UCP3 in brown fat, white fat, muscle, and other tissues also can be examined (Schrauwen et al., 1999).

Food intake relative to weight gain can be monitored, and feed efficiency can be calculated. In addition, the weight gain of the animals placed on high fat diets can be monitored. Wild type mice maintained on a high fat diet accumulate fat rapidly, whereas the results disclosed herein indicate the activin receptor mutant animals will remain relatively lean.

The results of these studies can provide a more complete profile of the effect of myostatin mice, particularly with respect to their overall metabolic state, thereby providing insight as to whether the ability of the myostatin knock-out mice to suppress the accumulation of fat is an anabolic effect of the myostatin mutation in muscle that leads to a shift in energy utilization such that little energy is available for storage in the form of fat. For example, the decreased fat accumulation can be due to an increased rate of thermogenesis. These results also will provide a baseline for comparison of the effect of the myostatin activity in the context of different genetic models of obesity and type II diabetes.

EXAMPLE 10

Characterization of Myostatin Effects in Genetic Models of Obesity and Type II Diabetes This example describes methods for determining the effect of myostatin in treating obesity or type II diabetes.

The dramatic reduction in overall fat accumulation in myostatin mutant mice as compared to wild type mice indicates that myostatin activity can be manipulated to treat or prevent obesity or type II diabetes. The effect of the myostatin mutation can be examined in the context of several well characterized mouse models of these metabolic diseases, including, for example, "obese" mice (ob/ob), "diabetic" mice (db/db), and agouti lethal yellow (AY) mutant strains. Each of these strains is abnormal for virtually every parameter and test described above (see, for example, Yen et al., supra, 1994, Friedman and Halaas, *Nature* 395:763-770, 1998). The ability of the myostatin mutation to slow or suppress the development of these abnormalities in mice carrying these other mutations can be examined by constructing double mutants, then subjecting the double mutant animals, along with appropriate control littermates carrying only the ob/ob, db/db, or agouti lethal yellow mutations, to the various tests.

As disclosed above, the myostatin mutation in $A^y$ mice was associated with about a 5-fold suppression of fat accumulation in the myostatin mutant $A^y$ mice, and with a partial suppression of the development of abnormal glucose metabolism as assessed by glucose tolerance tests. These results can be extended to include additional animals at various ages, and similar studies can be performed with the ob/ob and db/db mutants. As both the these mutations are recessive, mice that are doubly homozygous for the myostatin mutation and either the ob or db mutation can be generated. In order to examine the effects of partial loss of myostatin function in these genetic model systems, mice that are homozygous for the ob or db mutation and heterozygous for the myostatin mutation also are examined. Mice that are doubly heterozygous for the myostatin and ob mutations have been generated, and the offspring from matings of these doubly heterozygous mice can be examined, particularly with respect to fat accumulation and glucose metabolism. Partial suppression of either or both of these abnormalities in the obese mutants can indicate that myostatin is a target for the treatment of obesity and type II diabetes.

EXAMPLE 11

Characterization of Transgenic Mice Expressing Dominant Negative Polypeptides that can Affect Myostatin Activity This example describes methods for characterizing the effect of myostatin postnatally by expressing dominant negative polypeptides that can block myostatin expression or myostatin signal transduction.

Myostatin Inhibitors

The modulation of myostatin activity postnatally can be used to determine the effect of myostatin on muscle fiber number (hyperplasia) and muscle fiber size (hypertrophy). Conditional myostatin knock-out mice, in which the myostatin gene is deleted at defined times during the life of the animal, can be used for these studies. The tet regulator in combination with the cre recombinase provides a system for generating such mice. In this system, the expression of cre is induced by administration of doxycycline.

Transgenic mice expressing an inhibitor of myostatin from an inducible promoter also can be generated such that myostatin activity can be reduced or inhibited at defined times during the life of the animal. The tetracycline regulators are useful for generating such transgenic mice, in which the myostatin expression is induced by doxycycline.

A modification of the tet system, which utilizes co-expression of a hybrid reverse tet-transactivator (fusion protein of the activation domain of VP 16 with the mutant reverse tet repressor) and a hybrid tet-transrepressor (fusion protein of the KRAB repressor domain of mammalian KoxI with the native tet repressor), can be particularly useful for producing the transgenic mice (Rossi et al., *Nat. Genet.* 20:389-393, 1998; Forster et al., *Nucl. Acids Res.* 27:708-710, 1999). In this system, the hybrid reverse tet-transactivator binds tet operator sequences, and activates transcription only in the presence of tetracycline; the hybrid tet-transrepressor binds tet operator sequences and represses transcription only in the absence of tetracycline. By co-expressing these two fusion proteins, the basal activity of the target promoter is silenced by the tet-transrepressor in the absence of tetracycline, and is activated by the reverse tet-transactivator upon administration of tetracycline.

Two types of transgenic lines can be generated. In the first type, the transgene encodes a myostatin inhibitor polypeptide under the control of a muscle specific promoter, for example, the muscle creatine kinase promoter (Sternberg et al., supra, 1988) or the myosin light chain enhancer/promoter (Donoghue et al., supra, 1991). Individual transgenic lines are screened for specific expression of the tet regulators in skeletal muscle, and several independent lines for each of the two promoters are selected and examined to confirm that any effects observed are not due, for example, to integration site-specific effects. A construct containing the two tet regulators under the control of the myosin light chain promoter/enhancer has been constructed, and can be used for pronuclear injections. In the second type of line. the transgene contains a myostatin inhibitor polypeptide under the control of a minimal CMV promoter that further contains tet operator sequences.

The myostatin inhibitor can be a dominant negative form of myostatin or a myostatin prodomain, which, as disclosed herein, can inhibit myostatin activity. Dominant negative forms of TGF-β family members have been described (see, for example, Lopez et al., *Mol. Cell. Biol.* 12:1674-1679, 1992; Wittbrodt and Rosa, *Genes Devel.* 8:1448-1462, 1994), and contain, for example, a mutant proteolytic cleavage site, thereby preventing the protein from being processed into the biologically active species. When co-expressed in a cell with the endogenous wild type gene, the mutant protein forms non-functional heterodimers with the wild type protein, thus acting as a dominant negative. A mutant myostatin polypeptide containing a mutation in the promyostatin cleavage site has been constructed, and can be examined for a dominant negative effect by co-expressing the mutant with wild type myostatin in varying ratios in 293 cells. Conditioned medium from 293 cells transiently transfected with the constructs can be examined by western blot analysis and the ability of the mutant to block the formation of mature C-terminal dimers can be examined.

An expression construct encoding only the myostatin prodomain also can be utilized. As disclosed above, the prodomain forms a tight complex with the mature C-terminal dimer and blocks the ability of the mature C-terminal myostatin dimer to bind Act RIIB in cells expressing the receptor in culture. By analogy to TGF-β, the myostatin prodomain also can maintain the mature C-terminal dimer in an inactive latent complex in vivo.

These transgenic animals can be bred with those expressing the tet regulators to generate doubly transgenic lines containing both the tet regulators and the inhibitor target construct. These doubly transgenic lines can be screened for those in which all of the different components are expressed appropriately. Northern blot analysis using RNA obtained from various muscles and control tissues from representative mice in each line, before and after administration of doxycycline in the drinking water, can be used to identify such transgenic lines. Transgenic lines will be selected that do not express the transgene in any tissue in the absence of doxycycline, and that express the transgene only in muscle in the presence of doxycycline.

Doxycycline is administered to the selected transgenic animals and the effect on muscle mass is examined. Doxycycline can be administered to pregnant mothers to induce the expression of the inhibitor during embryogenesis. The effect of blocking myostatin activity during development of the transgenic animals can be compared to the effects observed in myostatin knock-out mice. Since the promoters for driving expression of the tet regulators can be induced at a later time during development than the time when myostatin is first expressed, the effect on muscle mass in the transgenic mice can be compared to the effect that occurs in the myostatin knock-out mice.

The effect of inhibiting myostatin activity postnatally can be examined by administering doxycycline to the doubly transgenic mice at various times after birth. Doxycycline treatment can begin, for example, at 3 weeks of age, and the animals can be analyzed at 5 months of age, which is the age at which the difference in muscle weights were at a maximum in the myostatin knock-out mice versus wild type mice. The animals are examined for the effects of the inhibitor on muscle mass. Muscles also can be examined histologically to determine effects on fiber number and fiber size. In addition, a fiber type analysis of various muscles in the transgenic mice can be performed to determine whether there is a selective effect on type I or type II fibers.

Doxycycline can be administered in different doses and at different times to characterize the effect of the myostatin inhibitors. Doubly transgenic mice also can be maintained chronically on doxycycline, then examined for effects on fat pad weights and other relevant metabolic parameters as described above. The results of these studies can confirm that modulating myostatin activity postnatally can increase muscle mass or decrease fat accumulation, thus indicating that targeting myostatin can be useful for the treatment of a variety of muscle wasting and metabolic diseases clinically.

Myostatin

Transgenic mice containing a myostatin transgene also can be examined and the effects produced upon expression of myostatin can be compared with those observed in the nude mice containing the myostatin-expressing CHO cells. Similarly as described above, myostatin can be placed under control of conditional (tet) and tissue specific regulatory elements, and expression of myostatin in the transgenic mice can be examined to determine whether a wasting syndrome occurs similar to that observed in the nude mice. The myostatin transgene can include, for example, processing signals derived from SV40, such that transgene can be distinguished from the endogenous myostatin gene.

Serum samples can be isolated from the myostatin transgenic mice at various times following the administration of doxycycline and the level of myostatin transgene product in the serum can be determined. Total body weights of the animals are monitored over time to determine whether the animals show significant weight loss. In addition, individual muscles and fat pads are isolated and weighed, and the number, size and type of muscle fibers are determined in selected muscle samples.

The level of myostatin transgene expression can be varied by varying the dose of doxycycline administered to the animals. Transgene expression can be monitored using, for example, northern blot analysis of transgene RNA levels in muscle, or myostatin protein levels in serum. The identification of specific levels of myostatin transgene expression allows a correlation of the extent of wasting induced by myostatin. The transgenic lines also can be crossed with the myostatin knock-out mice to generate mice in which the only source of myostatin is expression from the transgene. Expression of myostatin at various times during development can be examined and the effect of myostatin on fiber number, fiber size, and fiber type can be determined. The availability of mice in which the expression of myostatin can be precisely and rapidly controlled provides a powerful tool for further characterizing the myostatin signal transduction pathway and for examining the effects of various agents that potentially can be useful for modulating myostatin signal transduction.

Effectors of Myostatin Signal Transduction

Transgenic mice containing either dominant negative forms of a myostatin signal transduction pathway, which can include components of a TGF-β signal transduction pathway, that is expressed specifically in skeletal muscle can be generated. As disclosed herein, the Smad proteins, which mediate signal transduction through a pathway induced by activin type II receptors, can be involved in myostatin signal transduction.

Act RIIB can bind GDF-11, which is highly related to myostatin (McPherron et al., supra, 1997; Gamer et al., supra, 1999; Nakashima et al., Mech. Devel. 80:185-189, 1999), and expression of c-ski, which can bind an inhibit Smad 2, Smad 3, and Smad 4, dramatically affects muscle growth (Suprave et al., supra, 1990; Berk et al., supra, 1997; see, also, Luo et al., supra, 1999; Stroschein et al., supra, 1999; Sun et al., supra, 1999a and b; Akiyoshi et al., supra, 1999). As disclosed herein, myostatin interacts specifically with Act RIIB and, therefore, can exert its biological effect, at least in part, by binding to activin type II receptors in vivo and activating the Smad signaling pathway.

The role of the Smad signaling pathway in regulating muscle growth can be examined using transgenic mouse lines that are blocked, or capable of being blocked, at specific points in the Act RIIB/Smad signal transduction pathway. The muscle creatine kinase promoter or myosin light chain enhancer/promoter can be used to drive expression of various inhibitors of the Smad signal transduction pathway.

An inhibitor useful in this system can include, for example, follistatin; a dominant negative Act RIIB receptor; a dominant negative Smad polypeptide such as Smad 3; c-ski; or an inhibitory Smad polypeptide such as Smad 7. Follistatin can bind and inhibit the activity of certain TGF-13 family members, including GDF-11 (Gamer et al., supra, 1999). Dominant negative forms of an activin type II receptor can be obtained, for example, by expressing the extracellular domain, particularly a soluble form of an Act RIIB extracellular domain, or by expressing a truncated Act RIIB receptor that lacks the kinase domain or contains a mutation such that the mutant receptor lacks kinase activity. Smad 7 functions as an inhibitory Smad that can block the signaling pathway induced by activin, TGF-β, and BMP. A dominant negative form of Smad 3, for example, can be constructed by mutating the Smad 3 C-terminal phosphorylation sites, thereby blocking Smad 3 function (Liu et al., supra, 1997). c-ski overexpression has been correlated to muscle hypertrophy in transgenic mice (Suprave et al., supra, 1990).

Transgenic mice can be prepared and each founder line examined for proper, muscle-specific expression of the transgene. The selected mice are examined for total body weights, individual muscle weights, and muscle fiber sizes, numbers and types. Those lines demonstrating a clear effect on muscle mass can be examined further for fat accumulation and other relevant metabolic parameters as described above. The use of these different agents to target specific steps in the activin receptor/Smad signal transduction pathway is particularly informative because the signaling pathways for the different agents overlap at different steps. For example, follistatin binds to and inhibits activin and GDF-11 activity, but not TGF-β, whereas a dominant negative Smad 3 can block signaling through both activin and TGF-β receptors. Smad 7 can have an even more pleotropic because it blocks signaling through BMP receptors as well. The studies can allow the identification of specific targets for modulating myostatin activity, thus providing various strategies for developing drugs or other agents that modulate myostatin signal transduction and, therefore, myostatin activity.

In particular, the transgenic lines described herein can be used to determine the effect of blocking myostatin function or the Smad signaling pathway postnatally on the development of obesity or type II diabetes. For example, the inhibitory transgenes can e crossed into the ob/ob, db/db, and Ay mutant mice. In the absence of doxycycline, an inhibitor transgene is not expressed and, therefore, the animals are indistinguishable from each of the parental mutant mice. In the presence of doxycycline, the inhibitor is expressed and can block myostatin activity. The effect of blocking myostatin activity on development of the metabolic abnormalities in these mutant animals can be examined.

Expression of the inhibitor can be induced at an early age, for example, at 3 weeks of age, to maximize the effect. In addition, myostatin activity can be blocked prior to the time that the metabolic abnormalities become so severe as to be irreversible. Animals can be maintained on doxycycline and assessed at various ages using the tests described above, including those relating to fat accumulation and glucose metabolism. Any delay in the age at which one or more test results becomes abnormal in the ob/ob, db/db, and Ay mutant animals can be identified. Similar studies can be performed using older animals, which have developed some of the signs of obesity or type II diabetes, and the effect of blocking myostatin activity on various parameters, including fat weight and glucose metabolism, can be determined. The results of these studies can further identify specific targets that can be manipulated in an effort to prevent or treat obesity or type II diabetes.

EXAMPLE 12

Characterization of Myostatin Effect on the Induction of Cachexia

This example describes methods for determining the role of myostatin signal transduction in the development and progression of cachexia.

The activin receptor and Smad pathway can constitute at least part of the signal transduction pathway involved in mediating myostatin activity in normal individuals and, therefore, can be involved in mediating the effects that occur in an individual due to excess levels of myostatin. As disclosed herein, cachexia, for example, can be mediated, at least in part, by abnormally high levels of myostatin. As such, methods for manipulating signal transduction through the Smad pathway can provide a new strategy for developing drugs for the treatment of muscle wasting in general and cachexia in particular.

The role of the Smad signaling pathway in cachexia can be examined by examining the susceptibility of the various transgenic lines described above to cachexia, which can be induced, for example, by interleukin-6 (IL-6; Black et al., $Endocrinology$ 128:2657-2659, 1991, which is incorporated herein by reference]), tumor necrosis factor-$\alpha$ (TNF-$\alpha$; Oliff et al., $Cell$ 50:555-563, 1987, which is incorporated herein by reference), or certain tumor cells. In the case of IL-6 and TNF-$\alpha$, the inhibitor transgenes can be crossed into a nude mouse background, then the animals can be challenged with CHO cells that produce IL-6 or TNF-$\alpha$, which induce wasting in nude mice when overexpressed in this manner. CHO cells that overproduce IL-6 or TNF-$\alpha$ can be prepared using the methods described above for generating myostatin overproducing cells. For example, TNF-$\alpha$ cDNA can be cloned into the pMSXND expression vector (Lee and Nathans, $J. Biol. Chem.$ 263:3521-3527, 1988), then cells carrying amplified copies of the expression construct can be selected stepwise in increasing concentrations of methotrexate.

Tumor cells such as Lewis lung carcinoma cells (Matthys et al., $Eur. J. Cancer$ 27:182-187, 1991, which is incorporated herein by reference) or colon 26 adenocarcinoma cells (Tanaka et al., $J. Cancer Res.$ 50:2290-2295, 1990, which is incorporated herein by reference), which can induce cachexia in mice, also can be utilized for these studies. These cell lines cause severe wasting when grown as tumors in mice. Thus, the effect of these tumors can be examined in the various transgenic mice described herein. It is recognized that the various tumor cells will only grow in certain genetic backgrounds. For example, the Lewis lung carcinoma cells are routinely grown in C57 BL/6 mice, and the colon 26 carcinoma cells are routinely grown in BALB/c mice. Thus, the transgenes can be backcrossed into these or other genetic backgrounds to allow growth of the tumor cells.

Various parameters, including total body weight, individual muscle weight, muscle fiber size and number, food intake and serum parameters, including glucose levels, can be monitored. In addition, serum myostatin levels and myostatin RNA levels in muscle can be examined to confirm that increased myostatin expression is correlated with cachexia. The results of these studies can confirm that the action of myostatin is downstream of the cachexia-inducing agents in these experimental models. The results also can confirm that the Smad signaling pathway is essential for development of cachexia in these models, and can demonstrate that a therapeutic benefit can be obtained in the treatment of cachexia by modulating the Smad signaling pathway.

EXAMPLE 13

Identification and Characterization of Growth Differentiation Factor-8 (GDF-8) and GDF-11 Receptors This example describes methods for identifying and characterizing cell surface receptors for GDF-8 (myostatin) and GDF-11.

The purified GDF-8 and GDF-11 proteins will be used primarily to assay for biological activities. In order to identify potential target cells for GDF-8 and GDF-11 action cells expressing their receptors will be searched. For this purpose, the purified protein will be radio-iodinated using the chloramine T method, which has been used successfully to label other members of this superfamily, like TGF-$\beta$(Cheifetz et al., supra, 1987), activins (Sugino et al., $J. Biol. Chem.$ 263: 15249-15252, 1988), and BMPs (Paralkar et al., $Proc. Natl. Acad. Sci. USA$ 88:3397-3401, 1991), for receptor binding studies. The mature processed forms of GDF-8 and GDF-11 each contain multiple tyrosine residues. Two different approaches will be taken to identify receptors for these proteins.

One approach will determine the number, affinity, and distribution of receptors. Either whole cells grown in culture, frozen sections of embryos or adult tissues, or total membrane fractions prepared from tissues or cultured cells will be incubated with the labeled protein, and the amount or distribution of bound protein will be determined. For experiments involving cell lines or membranes, the amount of binding will be determined by measuring either the amount of radioactivity bound to cells on the dish after several washes or, in the case of membranes, the amount of radioactivity sedimented with the membranes after centrifugation or retained with the membranes on a filter. For experiments involving primary cultures, where the number of cells can be more limited, binding sites will be visualized directly by overlaying with photographic emulsion. For experiments involving frozen sections, sites of ligand binding will be visualized by exposing these sections to high resolution Beta-max hyperfilm; if finer localization is required, the sections will be dipped in photographic emulsion. For all of these experiments, specific binding will be determined by adding excess unlabeled protein as competitor (for example, see Lee and Nathans, supra, 1988).

A second approach will be to characterize the receptor biochemically. Membrane preparations or potential target cells grown in culture will be incubated with labeled ligand, and receptor/ligand complexes will be covalently crosslinked using disuccinimidyl suberate, which has been commonly used to identify receptors for a variety of ligands, including members of the TGF-β superfamily (Massague and Like, *J. Biol. Chem.* 260:2636-2645, 1985). Cross-linked complexes are separated by electrophoresis on SDS polyacrylamide gels to look for bands labeled in the absence, but not in the presence, of excess unlabeled protein. The molecular weight of the putative receptor will be estimated by subtracting the molecular weight of the ligand. An important question that these experiments will address is whether GDF-8 and GDF-11 signal through type I and type II receptors like many other members of the TGF-β superfamily (Massague and Weis-Garcia, supra, 1996).

Once a method for detecting receptors for these molecules has been achieved, more detailed analysis will be carried out to determine the binding affinities and specificities. A Scatchard analysis will be used to determine the number of binding sites and dissociation constants. By carrying out cross-competition analyses between GDF-8 and GDF-11, it will be possible to determine whether they are capable of binding to the same receptor and their relative affinities. These studies will give an indication as to whether the molecules signal through the same or different receptors. Competition experiments using other TGF-β family members will be performed to determine specificity. Some of these ligands are available commercially, and some others are available from Genetics Institute, Inc.

For these experiments, a variety of embryonic and adult tissues and cell lines will be tested. Based on the specific expression of GDF-8 in skeletal muscle and the phenotype of GDF-8 knock-out mice, initial studies focus on embryonic and adult muscle tissue for membrane preparation and for receptor studies using frozen sections. In addition, myoblasts will be isolated and cultured from embryos at various days of gestation or satellite cells from adult muscle as described (Vivarelli and Cossu, *Devel. Biol.* 117:319-325, 1986; Cossu et al., *Cell Diff.* 9:357-368, 1980). The binding studies on these primary cells after various days in culture will be performed and binding sites localized by autoradiography so that the binding sites can be c-o-localized with various myogenic markers, such as muscle myosin (Vivarelli et al., *J. Cell Biol.* 107:2191-2197, 1988), and correlate binding with the differentiation state of the cells, such as formation of multinucleated myotubes. In addition to using primary cells, cell lines will be utilized to look for receptors. In particular, the initial focus will be on three cells lines, C2C12, L6, and P19. C2C12 and L6 myoblasts differentiate spontaneously in culture and form myotubes depending on the particular growth conditions (Yaffe and Saxel, supra, 1977; Yaffe, supra, 1968). P19 embryonal carcinoma cells can be induced to differentiate into various cell types, including skeletal muscle cells in the presence of DMSO (Rudnicki and McBumey, *Teratocarcinomas and Embryonic Stem Cells: A practical approach* (E. J. Robertson, IRL Press, Cambridge 1987). Receptor binding studies will be carried out on these cell lines under various growth conditions and at various stages of differentiation. Although the initial studies will focus on muscle cells, other tissues and cell types will be examined for the presence of GDF-8 and GDF-11 receptors.

Recombinant human GDF-8 (rhGDF-8) homodimer will be used in these binding studies. RhGDF-8 was expressed using CHO cells and purified to approximately 90% purity. The rhGDF-8 had the expected 25 kDa to 27 kDa molecular weight and, upon reduction, was reduced to the 12 kDa monomer. Using 1-125 labeled GDF-8 in a receptor-ligand binding assay, two myoblast cell lines, L6 and G-8, bound GDF-8. The binding was specific since non labeled GDF-8 effectively competed the binding of the labeled ligand. The dissociation constant ($K_d$) was 370 pM, and L6 myoblasts have a high number (5,000 receptors/cell) of cell surface binding proteins. GDF-11 (BMP-11) is highly homologous (>90%) to GDF-8. Receptor binding studies revealed that GDF-8 and GDF-11 bound to the same binding proteins on L6 myoblasts. It is important to establish whether or not GDF-8 binds to the known TGF-β receptor. TGF-β did not compete the binding of GDF-8, indicating that the GDF-8 receptor is distinct from the TGF-β receptor. The GDF-8 receptor was not expressed on all myoblast cell lines, including four myoblast cell lines, C2C12, G7, MLB13MYC c14 and BC3H1, which do not bind GDF-8.

The gene or genes encoding receptors for GDF-8 and GDF-11 can be obtained. As a first step towards understanding the mechanism by which GDF-8 and GDF-11 exert their biological effects, it is important to clone the genes encoding their receptors. From the experiments above, it will be more clear as to whether GDF-8 and GDF-11 bind to the same receptor or to different receptors. There will also be considerable information regarding the tissue and cell type distribution of these receptors. Using this information, two different approaches will be taken to clone the receptor genes.

The first approach will be to use an expression cloning strategy. In fact, this was the strategy that was originally used by Mathews and Vale (*Cell* 65:973-982, 1991) and Lin et al. (*Cell* 68:775-785, 1992) to clone the first activin and TGF-β receptors. Poly A-selected RNA from the tissue or cell type that expresses the highest relative number of high affinity binding sites will be obtained, and used to prepare a cDNA library in the mammalian expression vector pcDNA-1, which contains a CMV promoter and an SV40 origin of replication. The library will be plated, and cells from each plate will be pooled into broth and frozen. Aliquots from each pool will be grown for preparation of DNA. Each individual pool will be transiently transfected into COS cells in chamber slides, and transfected cells will be incubated with iodinated GDF-8 or GDF-11. After washing away the unbound protein, the sites of ligand binding will be visualized by autoradiography. Once a positive pool is identified, the cells from that pool will be replated at lower density, and the process will be repeated. Positive pools will then be plated, and individual colonies will be picked into grids and re-analyzed as described (Wong et al., *Science* 228:810-815, 1985).

Initially, using pool sizes of 1500 colonies will be screened. In order to be certain to identify a positive clone in a mixture of this complexity, a control experiment using TGF-β and a cloned type II receptor will be performed. The coding sequence for the TGF-β type II receptor will be cloned into the pcDNA-1 vector, and bacteria transformed with this construct will be mixed with bacteria from our library at various ratios, including 1:1500. The DNA prepared from this mixture then will be transfected into COS cells, incubated with iodinated TGF-β, and visualized by autoradiography. If positive signals are observed at a ratio of 1:1500, pools of 1500 clones will be screened. Otherwise, smaller pool sizes corresponding to ratios at which the procedure is sensitive enough to identify a positive signal in control experiments will be used.

A second parallel strategy to attempt to clone the GDF-8 and GDF-11 receptors also will be used, taking advantage of the fact that most receptors for members of the TGF-β superfamily that have been identified belong to the membrane-spanning serine/threonine kinase family (Massague and Weis-Garcia, supra, 1996). Because the cytoplasmic domains of these receptors are related in sequence, degenerate PCR probes will be used to clone members of this receptor family that are expressed in tissues that contain binding sites for GDF-8 and GDF-11. In fact, this is the approach that has been used to identify most of the members of this receptor family. The general strategy will be to design degenerate primers corresponding to conserved regions of the known receptors, to use these primers for PCR on cDNA prepared from the appropriate RNA samples (most likely from skeletal muscle), to subclone the PCR products, and finally to sequence individual subclones. As sequences are identified, they will be used as hybridization probes to eliminate duplicate clones from further analysis. The receptors that are identified then will be tested for their ability to bind purified GDF-8 and GDF-11. Because this screen will yield only small PCR products, full-length cDNA clones will be obtained for each receptor from cDNA libraries prepared from the appropriate tissue, inserted into the pcDNA-1 vector, transfected into COS cells, and the transfected cells will be assayed for their ability to bind iodinated GDF-8 or GDF-11. Ideally, every receptor that is identified in this screen will be tested for the ability to bind these ligands. However, the number of receptors that are identified can be large, and isolating all of the full-length cDNAs and testing them can require considerable effort. Almost certainly some of the receptors that are identified will correspond to known receptors, and for these, either obtaining full-length cDNA clones from other investigators or amplifying the coding sequences by PCR based on the published sequences should be straightforward. For novel sequences, the tissue distribution will be determined by northern blot analysis and the highest priority will be directed to those receptors whose expression pattern most closely resembles the distribution of GDF-8 and/or GDF-11 binding sites as determined above.

In particular, it is known that these receptors fall into two classes, type I and type II, which can be distinguished based on the sequence and which are both required for full activity. Certain ligands cannot bind type I receptors in the absence of type II receptors while others are capable of binding both receptor types (Massague and Weis-Garcia, supra, 1996). The cross-linking experiments outlined above should give some indication as to whether both type I and type II receptors are also involved in signaling GDF-8 and GDF-11. If so, it will be important to clone both of these receptor subtypes in order to fully understand how GDF-8 and GDF-11 transmit their signals. Because it cannot be predicted as to whether the type I receptor is capable of interacting with GDF-8 and GDF-11 in the absence of the type II receptor, type II receptor(s) will be cloned first. Only after at least one type II receptor has been identified for these ligands, will an attempt be made to identify the type I receptors for GDF-8 and GDF-11. The general strategy will be to cotransfect the type II receptor with each of the type I receptors that are identified in the PCR screen, then assay the transfected cells by crosslinking. If the type I receptor is part of the receptor complex for GDF-8 or GDF-11, two cross-linked receptor species should be detected in the transfected cells, one corresponding to the type I receptor and the other corresponding to the type II receptor.

The search for GDF-8 and GDF-11 receptors is further complicated by the fact that at least one member of the TGF-β superfamily, namely, GDNF, is capable of signaling through a completely different type of receptor complex involving a GPI-linked component (GDNFR-alpha) and a receptor tyrosine kinase (c-ret; Trupp et al., Nature 381:785-789, 1996; Durbec et al., Nature 381:789-793, 1996; Treanor et al., Nature 382:80-83, 1996; Jing et al., Cell 85:1113-1124, 1996). Although GDNF is the most distantly-related member of the TGF-β superfamily, it is certainly possible that other TGF-β family members can also signal through an analogous receptor system. If GDF-8 and GDF-11 do signal through a similar receptor complex, the expression screening approach should be able to identify at least the GPI-linked component (indeed GDNFR-alpha was identified using an expression screening approach) of this complex. In the case of GDNF, the similar phenotypes of GDNF- and c-ret-deficient mice suggested c-ret as a potential receptor for GDNF.

EXAMPLE 14

Preparation and Characterization of GDF-11 Knock-Out Mice

The phenotype of GDF-11 knock-out mice in several respects resembles the phenotype of mice carrying a deletion of a receptor for some members of the TGF-β superfamily, including the activin type IIB receptor (Act RIIB). To determine the biological function of GDF-11, the GDF-11 gene was disrupted by homologous targeting in embryonic stem cells.

A murine 129 SvJ genomic library was prepared in lambda FIXII according to the instructions provided by Stratagene (La Jolla, Calif.). The structure of the GDF-11 gene was deduced from restriction mapping and partial sequencing of phage clones isolated from the library. Vectors for preparing the targeting construct were kindly provided by Philip Soriano and Kirk Thomas. To ensure that the resulting mice would be null for GDF-11 function, the entire mature C-terminal region was deleted and replaced by a neo cassette. R1ES cells were transfected with the targeting construct, selected with gancyclovir (2 μM) and G418 (250 μg/ml), and analyzed by Southern blot analysis.

Homologous targeting of the GDF-11 gene was observed in 8/155 gancyclovir/G418 doubly resistant ES cell clones. Following injection of several targeted clones into C57BL/6J blastocysts, chimeras were obtained from one ES clone that produced heterozygous pups when crossed to both C57BL/6J and 129/SvJ females. Crosses of C57BL/6J/129/SvJ hybrid F1 heterozygotes produced 49 wild type (34%), 94 heterozygous (66%), and no homozygous mutant adult offspring. Similarly, there were no adult homozygous null animals seen in the 129/SvJ background (32 wild type (36%) and 56 heterozygous mutant (64%) animals).

To determine the age at which homozygous mutants were dying, litters of embryos isolated at various gestational ages from heterozygous females that had been mated to heterozygous males were genotyped. At all embryonic stages examined, homozygous mutant embryos were present at approximately the predicted frequency of 25%. Among hybrid newborn mice, the different genotypes were also represented at the expected Mendelian ratio of 1:2:1 (34+/+(28%), 61+/− (50%), and 28−/− (23%)). Homozygous mutant mice were born alive and were able to breath and nurse. All homozygous mutants died, however, within the first 24 hours after birth. The precise cause of death was unknown, but the lethality may have been related to the fact that the kidneys in homozygous mutants were either severely hypoplastic or completely absent.

Homozygous mutant animals were easily recognizable by their severely shortened or absent tails. To further characterize the tail defects in these homozygous mutant animals, their skeletons were examined to determine the degree of disruption of the caudal vertebrae. A comparison of wild type and mutant skeleton preparations of late stage embryos and newborn mice, however, revealed differences not only in the caudal region of the animals but in many other regions as well. In nearly every case where differences were noted, the abnormalities appeared to represent homeotic transformations of vertebral segments in which particular segments appeared to have a morphology typical of more anterior segments. These transformations were evident throughout the axial skeleton extending from the cervical region to the caudal region. Except for the defects seen in the axial skeleton, the rest of the skeleton, such as the cranium and limb bones, appeared normal.

Anterior transformations of the vertebrae in mutant newborn animals were most readily apparent in the thoracic region, where there was a dramatic increase in the number of thoracic (T) segments. All wild type mice examined showed the typical pattern of 13 thoracic vertebrae each with its associated pair of ribs. In contrast, homozygous mutant mice showed a striking increase in the number of thoracic vertebrae. All homozygous mutants examined had 4 to 5 extra pairs of ribs for a total of 17 to 18, although in over ⅓ of these animals, the 18th rib appeared to be rudimentary. Hence, segments that would normally correspond to lumbar (L) segments L1 to L4 or L5 appeared to have been transformed into thoracic segments in mutant animals.

Moreover, transformations within the thoracic region in which one thoracic vertebra had a morphology characteristic of another thoracic vertebra were also evident. For example, in wild type mice, the first 7 pairs of ribs attach to the sternum, and the remaining 6 are unattached or free. In homozygous mutants, there was an increase in the number of both attached and free pairs of ribs to 10-11 and 7-8, respectively. Therefore, thoracic segments T8, T9, T10, and in some cases even T11, which all have free ribs in wild type animals, were transformed in mutant animals to have a characteristic typical of more anterior thoracic segments, namely, the presence of ribs attached to the sternum. Consistent with this finding, the transitional spinous process and transitional articular processes which are normally found on T10 in wild type animals were instead found on T13 in homozygous mutants. Additional transformations within the thoracic region were also noted in certain mutant animals. For example, in wild type mice, the ribs derived from T1 normally touch the top of the sternum. However, in ⅔₃ hybrid and ⅔ 129/SvJ homozygous mutant mice examined, T2 appeared to have been transformed to have a morphology resembling that of T1; that is, in these animals, the ribs derived from T2 extended to touch the top of the sternum. In these cases, the ribs derived from T1 appeared to fuse to the second pair of ribs. Finally, in 82% of homozygous mutants, the long spinous process normally present on T2 was shifted to the position of T3. In certain other homozygous mutants, asymmetric fusion of a pair of vertebrosternal ribs was seen at other thoracic levels.

The anterior transformations were not restricted to the thoracic region. The anterior most transformation that we observed was at the level of the 6th cervical vertebra (C6). In wild type mice, C6 is readily identifiable by the presence of two anterior tuberculi on the ventral side. In several homozygous mutant mice, although one of these two anterior tuberculi was present on C6, the other was present at the position of C7 instead. Hence, in these mice, C7 appeared to have been partially transformed to have a morphology resembling that of C6. One other homozygous mutant had 2 anterior tuberculi on C7 but retained one on C6 for a complete C7 to C6 transformation but a partial C6 to C5 transformation.

Transformations of the axial skeleton also extended into the lumbar region. Whereas wild type animals normally have only 6 lumbar vertebrae, homozygous mutants had 8 to 9. At least 6 of the lumbar vertebrae in the mutants must have derived from segments that would normally have given rise to sacral and caudal vertebrae as the data described above suggest that 4 to 5 lumbar segments were transformed into thoracic segments. Hence, homozygous mutant mice had a total of 33-34 presacral vertebrae compared to 26 presacral vertebrae normally present in wild type mice. The most common presacral vertebral patterns were C7/T18/L8 and C7/T18/L9 for mutant mice compared to C7/T13/L6 for wild type mice. The presence of additional presacral vertebrae in mutant animals was obvious even without detailed examination of the skeletons as the position of the hind limbs relative to the forelimbs was displaced posteriorly by 7 to 8 segments.

Although the sacral and caudal vertebrae were also affected in homozygous mutant mice, the exact nature of each transformation was not as readily identifiable. In wild type mice, sacral segments S1 and S2 typically have broad transverse processes compared to S3 and S4. In the mutants, there did not appear to be an identifiable S1 or S2 vertebra. Instead, mutant animals had several vertebrae that appeared to have morphology similar to S3. In addition, the transverse processes of all 4 sacral vertebrae are normally fused to each other although in newborns often only fusions of the first 3 vertebrae are seen. In homozygous mutants, however, the transverse processes of the sacral vertebrae were usually unfused. In the caudal-most region, all mutant animals also had severely malformed vertebrae with extensive fusions of cartilage. Although the severity of the fusions made it difficult to count the total number of vertebrae in the caudal region, up to 15 transverse processes were counted in several animals. It could not be determined whether these represented sacral or caudal vertebrae in the mutants because morphologic criteria for distinguishing S4 from caudal vertebrae even in wild type newborn animals could not be established. Regardless of their identities, the total number of vertebrae in this region was significantly reduced from the normal number of approximately 30. Hence, although the mutants had significantly more thoracic and lumber vertebrae than wild type mice, the total number of segments was reduced in the mutants due to the truncation of the tails.

Heterozygous mice also showed abnormalities in the axial skeleton although the phenotype was much milder than in homozygous mice. The most obvious abnormality in heterozygous mice was the presence of an additional thoracic segment with an associated pair of ribs. This transformation was present in every heterozygous animal examined, and in every case, the additional pair of ribs was attached to the sternum. Hence, T8, whose associated rib normally does not touch the sternum, appeared to have been transformed to a morphology characteristic of a more anterior thoracic vertebra, and L1 appeared to have been transformed to a morphology characteristic of a posterior thoracic vertebra. Other abnormalities indicative of anterior transformations were also seen to varying degrees in heterozygous mice. These included a shift of the long spinous process characteristic of T2 by one segment to T3, a shift of the articular and spinous processes from T10 to T11, a shift of the anterior tuberculus on C6 to C7, and transformation of T2 to T1 where the rib associated with T2 touched the top of the sternum.

In order to understand the basis for the abnormalities in axial patterning seen in GDF-11 mutant mice, mutant embryos isolated at various stages of development were examined, and compared o wild type embryos. By gross morphological examination, homozygous mutant embryos isolated up to day 9.5 of gestation were not readily distinguishable from corresponding wild type embryos. In particular, the number of somites present at any given developmental age was identical between mutant and wild type embryos, suggesting that the rate of somite formation was unaltered in the mutants. By day 10.5-11.5 p.c., mutant embryos could be easily distinguished from wild type embryos by the posterior displacement of the hind limb by 7-8 somites. The abnormalities in tail development were also readily apparent at this stage. Taken together, these data suggest that the abnormalities observed in the mutant skeletons represented true transformations of segment identities rather than the insertion of additional segments, for example, by an enhanced rate of somitogenesis.

Alterations in expression of homeobox containing genes are known to cause transformations in *Drosophila* and in vertebrates. To see if the expression patterns of Hox genes (the vertebrate homeobox containing genes) were altered in GDF-11 null mutants, the expression pattern of 3 representative Hox genes, Hoxc-6, Hoxc-8 and Hoxc-11, was determined in day 12.5 p.c. wild type, heterozygous and homozygous mutant embryos by whole mount in situ hybridization. The expression pattern of Hoxc-6 in wild type embryos spanned prevertebrae 8-15 which correspond to thoracic segments T1-T8. In homozygous mutants, however, the Hoxc-6 expression pattern was shifted posteriorly and expanded to prevertebrae 9-18 (T2-T11). A similar shift was seen with the Hoxc-8 probe. In wild type embryos, Hoxc-8 was expressed in prevertebrae 13-18 (T6-T11) but, in homozygous mutant embryos, Hoxc-8 was expressed in prevertebrae 14-22 (T7-T15). Finally, Hoxc-11 expression was also shifted posteriorly in that the anterior boundary of expression changed from prevertebrae 28 tin wild type embryos to prevertebrae 36 in mutant embryos. (Note that because the position of the hind limb is also shifted posteriorly in mutant embryos, the Hoxc-11 expression patterns in wild type and mutant appeared similar relative to the hind limbs). These data provide further evidence that the skeletal abnormalities seen in mutant animals represent homeotic transformations.

The phenotype of GDF-11 mice suggested that GDF-11 acts early during embryogenesis as a global regulator of axial patterning. To begin to examine the mechanism by which GDF-11 exerts its effects, the expression pattern of GDF-11 in early mouse embryos was examined by whole mount in situ hybridization. At these stages, the primary sites of GDF-11 expression correlated precisely with the known sites at which mesodermal cells are generated. Expression of GDF-11 was first detected at day 8.25-8.5 p.c. (8-10 somites) in the primitive streak region, which is the site at which ingressing cells form the mesoderm of the developing embryo. Expression was maintained in the primitive streak at day 8.75, but by day 9.5 p.c., when the tail bud replaces the primitive streak as the source of new mesodermal cells, expression of GDF-11 shifted to the tail bud. Hence, at these early stages, GDF-11 appears to be synthesized in the region of the developing embryo where new mesodermal cells arise and presumably acquire their positional identity.

The phenotype of GDF-11 knock-out mice in several respects resembled the phenotype of mice carrying a deletion of a receptor for some members of the TGF-β superfamily, the activin type IIB receptor (Act RIIB). As in the case of GDF-11 knock-out mice, the Act RIIB knock-out mice have extra pairs of ribs and a spectrum of kidney defects ranging from hypoplastic kidneys to complete absence of kidneys. The similarity in the phenotypes of these mice raises the possibility that Act RIIB can be a receptor for GDF-11. However, Act RIIB cannot be the sole receptor for GDF-11 because the phenotype of GDF-11 knock-out mice is more severe than the phenotype of Act RIIB mice. For example, whereas the GDF-11 knock-out animals have 4-5 extra pairs of ribs and show homeotic transformations throughout the axial skeleton, the Act RIIB knock-out animals have only 3 extra pairs of ribs and do not show transformations at other axial levels. In addition, the data indicate that the kidney defects in the GDF-11 knock-out mice are also more severe than those in Act RIIB knock-out mice. The Act RIIB knock-out mice show defects in left/right axis formation, such as lung isomerism and a range of heart defects that we have not yet observed in GDF-11 knock-out mice. Act RIIB can bind the activins and certain BMPs, although none of the knock-out mice generated for these ligands show defects in left/right axis formation.

If GDF-11 does act directly on mesodermal cells to establish positional identity; the data presented here would be consistent with either short range or morphogen models for GDF-11 action. That is, GDF-11 can act on mesodermal precursors to establish patterns of Hox gene expression as these cells are being generated at the site of GDF-11 expression, or alternatively, GDF-11 produced at the posterior end of the embryo can diffuse to form a morphogen gradient. Whatever the mechanism of action of GDF-11 may be, the fact that gross anterior/posterior patterning still does occur in GDF-11 knock-out animals suggests that GDF-11 may not be the sole regulator of anterior/posterior specification. Nevertheless, it is clear that GDF-11 plays an important role as a global regulator of axial patterning and that further study of this molecule will lead to important new insights into how positional identity along the anterior/posterior axis is established in the vertebrate embryo.

Similar phenotypes are expected in GDF-8 knock-out animals. For example, GDF-8 knock-out animals are expected to have increased number of ribs, kidney defects and anatomical differences when compared to wild type.

Although the invention has been described with reference to the above examples, it will be understood that modifications and variations are encompassed within the spirit and scope of the invention. Accordingly, the invention is limited only by the following claims.

What is claimed is:

1. An isolated polynucleotide encoding a promyostatin myostatin domain, or a polynucleotide complementary to said polynucleotide, said myostatin domain having muscle growth inhibitory activity, and said myostatin domain comprising:
   amino acid residues from about 49 to 157 of SEQ ID NO:27; or
   amino acid residues from about 28 to 136 of SEQ ID NO:29.

2. A vector, comprising a polynucleotide of claim 1.

3. The vector of claim 2, wherein said vector is a viral vector.

4. An isolated host cell containing the vector of claim 2.

5. An isolated polynucleotide, comprising SEQ ID NO:26 or SEQ ID NO:28.

* * * * *